(12) United States Patent
Chen et al.

(10) Patent No.: US 9,284,330 B2
(45) Date of Patent: Mar. 15, 2016

(54) 1,4-DIHYDRO-NAPHTHYRIDINE DERIVATIVE AND PHARMACEUTICAL COMPOSITION AND USE THEREOF

(71) Applicants: Rong Chen, Jiangsu (CN); Lin Feng, Jiangsu (CN); Zhengping Zhang, Jiangsu (CN); Fang Fang, Jiangsu (CN); Qingli Dong, Jiangsu (CN); Fulong Li, Jiangsu (CN); Lei Wang, Jiangsu (CN); Yao Hua, Jiangsu (CN); Shibao Yang, Jiangsu (CN); Peng Wang, Jiangsu (CN)

(72) Inventors: Rong Chen, Jiangsu (CN); Lin Feng, Jiangsu (CN); Zhengping Zhang, Jiangsu (CN); Fang Fang, Jiangsu (CN); Qingli Dong, Jiangsu (CN); Fulong Li, Jiangsu (CN); Lei Wang, Jiangsu (CN); Yao Hua, Jiangsu (CN); Shibao Yang, Jiangsu (CN); Peng Wang, Jiangsu (CN)

(73) Assignee: Jiangsu Simovay Pharmaceutical Co., Ltd. (CN)

( * ) Notice: Subject to any disclaimer, the term of this patent is extended or adjusted under 35 U.S.C. 154(b) by 0 days.

(21) Appl. No.: 14/362,735

(22) PCT Filed: Dec. 7, 2012

(86) PCT No.: PCT/CN2012/086145
§ 371 (c)(1),
(2) Date: Jun. 4, 2014

(87) PCT Pub. No.: WO2013/083070
PCT Pub. Date: Jun. 13, 2013

(65) Prior Publication Data
US 2014/0364443 A1  Dec. 11, 2014

(30) Foreign Application Priority Data
Dec. 7, 2011 (CN) .......................... 2011 1 0405079

(51) Int. Cl.
*C07D 495/14* (2006.01)
*C07D 471/14* (2006.01)
*C07D 471/04* (2006.01)
*C07D 471/12* (2006.01)
*C07D 491/14* (2006.01)

(52) U.S. Cl.
CPC ............ *C07D 495/14* (2013.01); *C07D 471/04* (2013.01); *C07D 471/12* (2013.01); *C07D 471/14* (2013.01); *C07D 491/14* (2013.01)

(58) Field of Classification Search
CPC .. C07D 471/04; C07D 417/12; C07D 495/14; C07D 491/14

USPC ........................ 546/82, 83, 88, 70; 514/256
See application file for complete search history.

(56) References Cited

FOREIGN PATENT DOCUMENTS

WO    WO 2011/051527 A1    5/2011

OTHER PUBLICATIONS

Synthesis and Acetylcholinesterase/Butyrycholinesterase Inhibition Activity of New Tacrine-like analogs, Jose Marco et al 2001, pp. 727-732.*
Synthesis , biological evaluation and molecular modelling of diversely functionalized heterocylic derivatives as inhibitors of acetylcholinesterase/butyrylcholinesterase and modulators of Ca+ channels and nicotine receptors, Jose Marco et al, 2004 , pp. 2199-2218.*
Modelling of acetylcholinesterase inhibition by tactrine analogues using Bayesian-regularized Genetic Neural Networks and ensembele averaging., Michael Fernandez et al , 2006, 647-661.*
Quantitative structure-activity relationship (QSAR) of tacrine derivatives against acetylcholinesterase (AChE) activity using variable selections, Mankil Jung et al , 2007, 1082-1090.*
Leon et al., "New tacrine-dihydropyridine hybrids that inhibit acetylcholinesterase, calcium entry, and exhibit neuroprotection properties", Bioorganic & Medicinal Chemistry, 2008, 16, 7759-7769.
Marco-Contelles et al., "Novel Multipotent-Tacrine-Dihydropyridine Hybrids with Improved Acetylcholinesterase Inhibitory and Neuroprotective Activities as Potential Drugs for the Treatment of Alzheimer's Disease", Journal of Medicinal Chemistry, 2006, 49, 26, 7607-7610.
Marco-Contelles et al., "Tacripyrines, the First Tacrine-Dihydropyridine Hybrids, as Multitarget-Directed Ligands for the Treatment of Alzheimer's Disease", Journal of Medicinal Chemistry, 2009, 52, 2724-2732.
Chen et al., "3D-QSAR study of multi-target-directed AchE inhibitors based on autodocking", Medicinal Chemistry Research, 2012, 21, 245-256.
European Patent Application No. 12854852.6—1462/2789613: Supplementary European Search Report dated Apr. 2, 2015, 9 pages.

* cited by examiner

*Primary Examiner* — Rita Desai
(74) *Attorney, Agent, or Firm* — Baker & Hostetler LLP

(57) ABSTRACT

Disclosed are 1,4-dihydro-naphthyridine derivatives and pharmaceutical composition and uses thereof. The 1,4-dihydro-naphthyridine derivatives are a compound capable of inhibiting acetylcholinesterase activity and preventing extracellular calcium from flowing into a cell via a calcium channel, i.e., having a dual-activity, which are of potential importance as a pharmaceutical and can be used to prepare the drugs for treating cardiovascular diseases, cerebrovascular diseases and dementia.

6 Claims, 1 Drawing Sheet

1,4-DIHYDRO-NAPHTHYRIDINE DERIVATIVE AND PHARMACEUTICAL COMPOSITION AND USE THEREOF

CROSS-REFERENCE TO RELATED APPLICATIONS

This application is the National Stage of International Application No. PCT/CN2012/086145, filed Dec. 7, 2012, which claims the benefit of Chinese application number 201110405079.2, filed Dec. 7, 2011, the disclosures of which are incorporated herein by reference in their entireties.

FIELD OF THE INVENTION

The present invention relates to the field of medicinal chemistry, particularly to 1,4-dihydro-1,8-naphthyridine compounds or the pharmaceutically acceptable salts thereof, and the pharmaceutical compositions comprising the compounds or the pharmaceutically acceptable salts thereof, and to the use, particularly the use for preparing medicaments for the treatment of cardiovascular diseases, cerebrovascular disease or dementia, of the compounds or the pharmaceutically acceptable salts thereof, and the pharmaceutical compositions comprising the compounds or the pharmaceutically acceptable salts thereof as L-type calcium channel blocker or/and acetylcholinesterase inhibitor.

BACKGROUND OF THE INVENTION

Alzheimer's disease is a degenerative disease of the human central nervous system, which is mainly characterized by chronic, progressive cognitive impairment and memory damage. It is manifested by senile plaques, neurofibrillary tangles and neuronal loss, which has a strong impact on the cognition, memory, linguistic function, and living abilities, emotion and personality of the patients. At present, "cholinergic depletion theory" is well-acceptable worldwide for the pathogenesis of Alzheimer's disease. It is believed by the theory that the depletion of neurotransmitter—acetylcholine is a key factor for Alzheimer's disease.

Cholinesterase is a critical enzyme in biological nerve conduction, and in the cholinergic synapses, it is capable of degrading acetylcholine, terminating the excitation effect of neurotransmitter on the postsynaptic membrane, and ensuring normal transmission of nerve signals within an organism. However, acetylcholinesterase may result in the depletion of acetylcholine due to its capability of catalyzing the cleavage reaction of acetylcholine, further leading to the failure of signal transmission and the influence on the organism's functions such as cognition, memory etc. At present, for the purpose of treating of Alzheimer's disease, the activity of cholinesterase is usually inhibited by an acetylcholinesterase inhibitor so as to slow down the hydrolysis rate of acetylcholine and enhance the acetylcholine level in the synaptic cleft.

Vascular dementia is an acquired syndrome of intelligent damage caused by various cerebrovascular diseases, with the clinical manifestations including intellectual deterioration in memory, calculation, attention and execution etc., and it is now the most common causes for dementia behind Alzheimer's disease. It is thought by researchers that one of the damage mechanisms is cerebral infarction, ischemic and hypoxic hypoperfusion and hemorrhage pathology, which result in the reduction of the brain tissue volume, delayed neuronal death, and further lead to the intracerebral acetylcholinergic nerve damage, the decrease in acetylcholine release, and gradual appearance of dysmnesia, cognitive impairment, and declined society and daily life function. Administration of acetylcholinesterase inhibitor will improve the cognition, execution and activities of daily life of the patients.

Another mechanism of damage to the cerebral cortical neurons in the patients of vascular dementia is the increased influx of calcium into the brain, which results in the decline in the study and memory function. If the calcium channel antagonists such as nimodipine enter into the brain tissue and reversibly bind with the calcium channel related receptor, so as to suppress the influx of calcium ion into neurocytes, advantages can be achieved, such as improved tolerance to ischemia, dilation of cerebral vessels and improvement of cerebral blood supply, protection of neurons, and efficient improvement of the cognition of the patients of vascular dementia.

However, there is no compound that not only can inhibit the activity of acetylcholinesterase, but also can block the influx of extracellular calcium ions into cells through the calcium channel at present, and thus, it is of great importance to develop such type of compounds.

DESCRIPTION OF THE INVENTION

Figure 1:
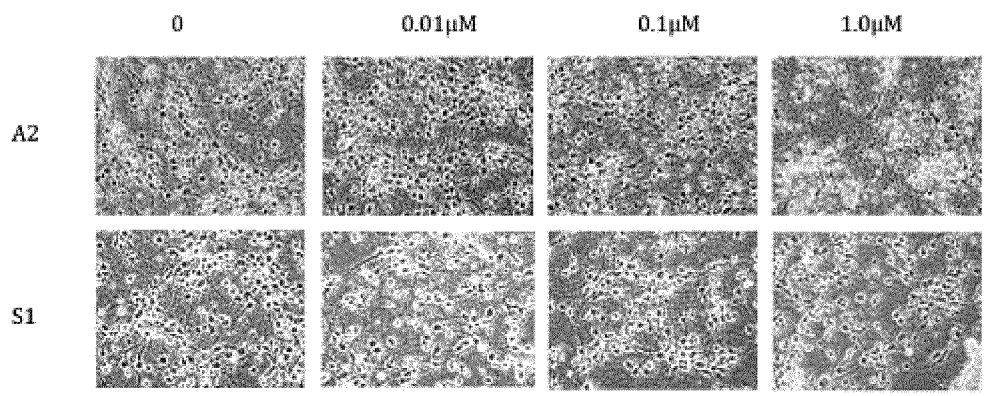
FIG. 1 depicts the effect of compounds of the disclosure on the morphology of primary neurons.

The aim of the present invention is to provide a type of compounds that not only can inhibit the activity of acetylcholinesterase, but also can block the influx of extracellular calcium ions into cells through the calcium channel, the pharmaceutical compositions comprising the same, and the use of the compounds and the pharmaceutical compositions as L-type calcium channel blocker or/and acetylcholinesterase inhibitor.

To solve the technical problems mentioned above, a technical proposal is provided herein below:

A type of compounds of formula I or the pharmaceutically acceptable salts thereof,

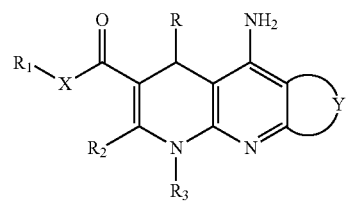

Formula I wherein, R is selected from the group consisting of aryl and heteroaryl, and said aryl or heteroaryl is optionally substituted on the ring by halogen atom, hydroxy, sulfhydryl, amino, nitro, cyano, trihaloalkyl, carboxyl, acyl, alkoxyl, aryl, heteroaryl, heteroalicyclic group, $C_1$-$C_{10}$ alkyl, $C_3$-$C_8$ cycloalkyl, $C_2$-$C_8$ alkenyl or $C_2$-$C_8$ alkynyl, wherein the substituents on two optional positions can be combined to form aliphatic ring, heterocyclic ring, aromatic ring, or heteroaromatic ring, and optional —$CH_2$— on said $C_1$-$C_{10}$ alkyl, $C_3$-$C_8$ cycloalkyl, $C_2$-$C_8$ alkenyl or $C_2$-$C_8$ alkynyl can be replaced by one or two or more of —O—, —S—, —$SO_2$—, —C(O)— or/and —NR$_6$—, and said C$_1$-C$_{10}$ alkyl, C$_3$-C$_8$ cycloalkyl, C$_2$-C$_8$ alkenyl or C$_2$-C$_8$ alkynyl can be optionally substituted by one or two or more of halogen atom, cyano, nitro, aryl, heteroaryl, aryloxy, heteroalicyclic group, amino, hydroxy and —NR$_4$R$_5$;

X is selected from the group consisting of —O— and —NR$_7$—;

R$_4$ and R$_5$ are independently selected from the group consisting of hydrogen, aryl, heteroaryl, C$_1$-C$_8$ alkyl, C$_3$-C$_8$ cycloalkyl, C$_2$-C$_8$ alkenyl and C$_2$-C$_8$ alkynyl, or R$_4$ and R$_5$ are combined to form a heteroalicyclic group;

R$_6$ and R$_7$ are independently selected from the group consisting of hydrogen, aryl, heteroaryl, C$_1$-C$_8$ alkyl, C$_3$-C$_8$ cycloalkyl and C$_2$-C$_8$ alkenyl, C$_2$-C$_8$ alkynyl;

R$_1$ is selected from the group consisting of hydrogen, hydroxy, aryl, heteroaryl, C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —SO$_2$—, —C(O)— or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom, cyano, nitro, aryl, heteroaryl, amino and —NR$_4$R$_5$;

R$_2$ is selected from the group consisting of hydrogen, halogen atom, nitro, amino, hydroxy, trihaloalkyl, C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —SO$_2$—, —C(O)— or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom, cyano, nitro, aryl, heteroaryl, amino and —NR$_4$R$_5$;

R$_3$ is selected from the group consisting of hydrogen, C$_1$-C$_8$ alkyl and C$_3$-C$_8$ cycloalkyl, and optional —CH$_2$— on said C$_1$-C$_8$ alkyl or C$_3$-C$_8$ cycloalkyl can be replaced by one or two or more of —O—, —S—, —SO$_2$—, —C(O)— or/and —NR$_6$—, and any position on said C$_1$-C$_8$ alkyl or C$_3$-C$_8$ cycloalkyl can be substituted by one or two or more of halogen atom, cyano, nitro, aryl, heteroaryl, amino and —NR$_4$R$_5$;

Y is selected from the group consisting of C$_2$-C$_8$ alkenylene, C$_2$-C$_8$ alkynylene and non-hydrogen substituted C$_2$-C$_8$ alkylene, and optional —CH$_2$— on said C$_2$-C$_8$ alkenylene, C$_2$-C$_8$ alkynylene or non-hydrogen substituted C$_2$-C$_8$ alkylene can be replaced by one or two or more of —O—, —S—, —C(O)— or/and —NR$_6$—, and any position on said replaced or unreplaced C$_2$-C$_8$ alkenylene, C$_2$-C$_8$ alkynylene or non-hydrogen substituted C$_2$-C$_8$ alkylene can be substituted by one or two or more of halogen atom, hydroxy, sulfhydryl, amino, cyano, nitro, aryl, heteroaryl, heteroalicyclic group, —NR$_4$R$_5$, C$_1$-C$_8$ alkyl, C$_3$-C$_8$ cycloalkyl, C$_2$-C$_8$ alkenyl and C$_2$-C$_8$ alkynyl, wherein substituents on two adjacent positions can be combined to form aliphatic ring, heterocyclic ring, aromatic ring or heteroaromatic ring.

Preferably, in the above compounds,

R is selected from the group consisting of aryl and heteroaryl, and said aryl or heteroaryl is substituted at optional potions on the ring by halogen atom, amino, nitro, cyano, trihaloalkyl, acyl, alkoxyl, aryl, heteroaryl, heteroalicyclic group, C$_1$-C$_8$ alkyl, C$_3$-C$_8$ cycloalkyl, C$_2$-C$_8$ alkenyl or C$_2$-C$_8$ alkynyl, wherein the substituents on two optional positions can be combined to form aliphatic ring, heterocyclic ring, aromatic ring, or heteroaromatic ring, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —SO$_2$—, —C(O)— or/and —NR$_6$—, and said C$_1$-C$_8$ alkyl, C$_3$-C$_8$ cycloalkyl, C$_2$-C$_8$ alkenyl or C$_2$-C$_8$ alkynyl can be substituted at optional positions by one or two or more of halogen atom, cyano, amino, hydroxy and —NR$_4$R$_5$;

X is selected from the group consisting of —O— and —NR$_7$—;

R$_4$ and R$_5$ are independently selected from the group consisting of hydrogen, aryl, heteroaryl, C$_1$-C$_8$ alkyl and C$_3$-C$_8$ cycloalkyl, or R$_4$ and R$_5$ are combined to form a heteroalicyclic group;

R$_6$ is selected from the group consisting of hydrogen, aryl, heteroaryl, C$_1$-C$_8$ alkyl and C$_3$-C$_8$ cycloalkyl;

R$_7$ is selected from the group consisting of hydrogen, C$_1$-C$_8$ alkyl and C$_3$-C$_8$ cycloalkyl;

R$_1$ is selected from the group consisting of C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —C(O)— or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom, cyano, nitro, aryl, heteroaryl, amino and —NR$_4$R$_5$;

R$_2$ is selected from the group consisting of halogen atom, trihaloalkyl, C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S— or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom, cyano, aryl, heteroaryl, amino and —NR$_4$R$_5$;

R$_3$ is selected from the group consisting of hydrogen, C$_1$-C$_8$ alkyl and C$_3$-C$_8$ cycloalkyl, and optional —CH$_2$— on said C$_1$-C$_8$ alkyl or C$_3$-C$_8$ cycloalkyl can be replaced by one or two or more of —O—, —S—, —C(O)— or/and —NR$_6$—, and any position on said C$_1$-C$_8$ alkyl or C$_3$-C$_8$ cycloalkyl can be substituted by one or two or more of halogen atom;

Y is selected from the group consisting of C$_2$-C$_8$ alkenylene, C$_2$-C$_8$ alkynylene and non-hydrogen substituted C$_2$-C$_8$ alkylene, and optional —CH$_2$— on said C$_2$-C$_8$ alkenylene, C$_2$-C$_8$ alkynylene or non-hydrogen substituted C$_2$-C$_8$ alkylene can be replaced by one or two or more of —O—, —S—, —C(O)— or/and —NR$_6$—, and any position on said replaced or unreplaced C$_2$-C$_8$ alkenylene, C$_2$-C$_8$ alkynylene or non-hydrogen substituted C$_2$-C$_8$ alkylene can be substituted by one or two or more of halogen atom, hydroxy, sulfhydryl, amino, cyano, nitro, heteroalicyclic group, —NR$_4$R$_5$, C$_1$-C$_8$ alkyl, C$_3$-C$_8$ cycloalkyl and C$_2$-C$_8$ alkenyl, wherein substituents on two adjacent positions can be combined to form aliphatic ring, heterocyclic ring, aromatic ring or heteroaromatic ring.

More preferably, in the above compounds,

R is selected from the group consisting of aryl and heteroaryl, and said aryl or heteroaryl is substituted at optional positions on the ring by halogen atom, nitro, cyano, trihaloalkyl, acyl, alkoxyl, heteroalicyclic group, C$_1$-C$_8$ alkyl, C$_3$-C$_8$ cycloalkyl, C$_2$-C$_8$ alkenyl or C$_2$-C$_8$ alkynyl, wherein the substituents on two optional positions can be combined to form aliphatic ring, heterocyclic ring, aromatic ring, or heteroaromatic ring, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —SO$_2$—, —C(O)— or/and —NR$_6$—, and said C$_1$-C$_8$ alkyl, C$_3$-C$_8$ cycloalkyl, C$_2$-C$_8$ alkenyl or C$_2$-C$_8$ alkynyl can be substituted at optional positions by one or two or more of halogen atom, cyano, amino and —NR$_4$R$_5$;

X is selected from the group consisting of —O— and —NR$_7$—;

R$_4$ and R$_5$ are independently selected from the group consisting of hydrogen, C$_1$-C$_8$ alkyl and C$_3$-C$_8$ cycloalkyl, or R$_4$ and R$_5$ are combined to form a heteroalicyclic group;

R$_6$ is selected from the group consisting of hydrogen, C$_1$-C$_8$ alkyl and C$_3$-C$_8$ cycloalkyl;

R$_7$ is selected from the group consisting of hydrogen and C$_1$-C$_8$ alkyl;

R$_1$ is selected from the group consisting of C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, —C(O)— or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom, aryl, heteroaryl, amino and —NR$_4$R$_5$;

R$_2$ is selected from the group consisting of trihaloalkyl, C$_1$-C$_8$ alkyl and C$_3$-C$_8$ cycloalkyl, and optional —CH$_2$— on said C$_1$-C$_8$ alkyl or C$_3$-C$_8$ cycloalkyl can be replaced by one or two or more of —O—, —S— or/and —NR$_6$—, and any position on said C$_1$-C$_8$ alkyl or C$_3$-C$_8$ cycloalkyl can be substituted by one or two or more of halogen atom, aryl, heteroaryl and —NR$_4$R$_5$;

R$_3$ is selected from the group consisting of hydrogen and C$_1$-C$_8$ alkyl;

Y is selected from the group consisting of C$_2$-C$_8$ alkenylene, C$_2$-C$_8$ alkynylene and non-hydrogen substituted C$_2$-C$_8$ alkylene, and optional —CH$_2$— on said C$_2$-C$_8$ alkenylene, C$_2$-C$_8$ alkynylene or non-hydrogen substituted C$_2$-C$_8$ alkylene can be replaced by one or two or more of —O—, —S—, —C(O)— or/and —NR$_6$—, and any position on said replaced or unreplaced C$_2$-C$_8$ alkenylene, C$_2$-C$_8$ alkynylene or non-hydrogen substituted C$_2$-C$_8$ alkylene can be substituted by one or two or more of halogen atom, cyano, nitro, heteroalicyclic group, —NR$_4$R$_5$, C$_1$-C$_8$ alkyl, C$_3$-C$_8$ cycloalkyl and C$_2$-C$_8$ alkenyl, wherein substituents on two adjacent positions can be combined to form aliphatic ring, heterocyclic ring, aromatic ring or heteroaromatic ring.

More preferably, in the above compounds,

R is selected from the group consisting of phenyl and heteroaryl, and said phenyl or heteroaryl is substituted at optional position on the ring by halogen atom, nitro, cyano, trihaloalkyl, acyl, alkoxyl, heteroalicyclic group, C$_1$-C$_8$ alkyl, C$_2$-C$_8$ alkenyl or C$_2$-C$_8$ alkynyl, wherein two adjacent substituents can be combined to form an aliphatic ring, heterocyclic ring or heteroaromatic ring, and optional —CH$_2$— on said C$_1$-C$_8$ alkyl, C$_2$-C$_8$ alkenyl or C$_2$-C$_8$ alkynyl can be replaced by one or two or more of —O—, —S— or/and —NR$_6$—;

X is —O—;

R$_4$, R$_5$ and R$_6$ are independently selected from the group consisting of hydrogen, C$_1$-C$_8$ alkyl and C$_3$-C$_8$ cycloalkyl;

R$_1$ is selected from the group consisting of C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more of halogen atom and —NR$_4$R$_5$;

R$_2$ is selected from the group consisting of trihaloalkyl and C$_1$-C$_8$ alkyl;

R$_3$ is selected from the group consisting of hydrogen and C$_1$-C$_6$ alkyl;

Y is selected from the group consisting of C$_2$-C$_8$ alkenylene, C$_2$-C$_8$ alkynylene and non-hydrogen substituted C$_2$-C$_8$ alkylene, and optional —CH$_2$— on said C$_2$-C$_8$ alkenylene, C$_2$-C$_8$ alkynylene or non-hydrogen substituted C$_2$-C$_8$ alkylene can be replaced by one or two or more of —O—, —S—, —C(O)— or/and —NR$_6$—, and any position on said replaced or unreplaced C$_2$-C$_8$ alkenylene, C$_2$-C$_8$ alkynylene or non-hydrogen substituted C$_2$-C$_8$ alkylene can be substituted by one or two or more of halogen atom, C$_1$-C$_6$ alkyl and C$_2$-C$_6$ alkenyl, wherein substituents on two adjacent positions can be combined to form an aliphatic ring, heterocyclic ring, aromatic ring or heteroaromatic ring.

More preferably, in the above compounds,

R is selected from the group consisting of phenyl and heteroaryl, and said phenyl or heteroaryl is substituted at any position on the ring by halogen atom, nitro, cyano, trihaloalkyl, acyl, alkoxyl, heteroalicyclic group, C$_1$-C$_8$ alkyl, wherein two adjacent substituents can be combined to form an aliphatic ring, heterocyclic ring, aromatic ring or heteroaromatic ring, and optional —CH$_2$— on said C$_1$-C$_8$ alkyl can be replaced by one or two or more of —O—, —S— or/and —NR$_6$—;

X is —O—;

R$_4$ and R$_5$ are independently selected from the group consisting of hydrogen and C$_1$-C$_8$ alkyl;

R$_6$ is selected from the group consisting of hydrogen and C$_1$-C$_8$ alkyl;

R$_1$ is selected from the group consisting of C$_1$-C$_8$ alkyl, C$_3$-C$_8$ cycloalkyl, C$_2$-C$_8$ alkenyl and C$_2$-C$_8$ alkynyl, and optional —CH$_2$— on said C$_1$-C$_8$ alkyl, C$_3$-C$_8$ cycloalkyl, C$_2$-C$_8$ alkenyl or C$_2$-C$_8$ alkynyl can be replaced by one or two or more of —O—, —S—, or/and —NR$_6$—, and any position on said C$_1$-C$_8$ alkyl, C$_3$-C$_8$ cycloalkyl, C$_2$-C$_8$ alkenyl or C$_2$-C$_8$ alkynyl can be substituted by one or two or more —NR$_4$R$_5$;

R$_2$ is selected from the group consisting of trihaloalkyl and C$_1$-C$_6$ alkyl;

R$_3$ is selected from the group consisting of hydrogen, methyl and ethyl;

Y is selected from the group consisting of C$_2$-C$_8$ alkenylene, C$_2$-C$_8$ alkynylene and non-hydrogen substituted C$_2$-C$_8$ alkylene, and optional —CH$_2$— on said C$_2$-C$_8$ alkenylene, C$_2$-C$_8$ alkynylene or non-hydrogen substituted C$_2$-C$_8$ alkylene can be replaced by one or two or more of —O—, —S—, —C(O)— or/and —NR$_6$—, and any position on said replaced or unreplaced C$_2$-C$_8$ alkenylene, C$_2$-C$_8$ alkynylene or non-hydrogen substituted C$_2$-C$_8$ alkylene can be substituted by one or two or more of halogen atom, methyl, ethyl and propyl, wherein substituents on two adjacent positions can be combined to form an aliphatic ring, heterocyclic ring, aromatic ring or heteroaromatic ring.

Unless otherwise indicated, the following terms used in the claims and specification have the meanings discussed below.

The expression way of carbon atom number of a group mentioned in the specification, for example C$_1$-C$_{10}$, means that the group may contain 1 carbon atom, 2 carbon atoms, 3 carbon atoms, and up to 10 carbon atoms;

Alkyl refers to a saturated aliphatic group, including straight and branched chain hydrocarbonyl, which includes, but not limited to, methyl, ethyl, propyl, isopropyl, n-butyl, isobutyl, t-butyl, n-pentyl, n-hexyl, and the like;

Alkylene refers to a bivalent alkyl;

Alkenyl refers to an unsaturated straight or branched chain hydrocarbonyl compring at least one carbon-carbon double bond, which includes, but not limited to, ethylene, propylene, isopropylene, butylene, isobutylene, t-butylene, n-pentene, isopentene, n-hexylene group and the like;

Alkenylene refers to a bivalent alkenyl;

Alkynyl refers to an unsaturated straight or branched chain hydrocarbonyl comprising one or two or more carbon-carbon triple bonds, which includes, but not limited to, acetenyl, allylene, isoallylene, butyne, isobutyne, t-butyne, pentyne, and and hexyne group;

Alkynylene refers to a bivalent alkynyl;

Cycloalkyl refers to a monocyclic or fused ring consisting of only carbon atoms (fused ring means that each ring in the system shares an adjacent pair of carbon atoms with the other ring in the system), wherein one or more of the rings may not contain a completely conjugated pi-electron system, and the examples of cycloalkyl include, but not limited to, cyclopropane, cyclobutane, cyclopentane, cyclopentene, cyclohexane, adamantane, cyclohexene, cyclohexadiene, cycloheptane, cyclooctane, cycloheptadiene, cycloheptatriene and the like;

Alkoxyl refers to an alkyl or cycloalkyl linked via oxygen bond;

Aryloxy refers to —O-aryl and —O-heteroaryl, which includes, but not limited to, phenoxy, pyridyloxy, furyloxy, thienyloxy, pyrimidinyloxy, pyrazinyloxy, and the derivatives thereof;

Substituted phenyl refers to a phenyl substituted by one or two or more substituents, wherein the substituent includes, but not limited to, $C_1$-$C_6$ alkyl, $C_2$-$C_6$ alkenyl, $C_2$-$C_6$ alkynyl, $C_1$-$C_6$ alkoxyl, $C_2$-$C_6$ alkenyloxy, phenoxy, benzyloxy, hydroxy, carboxyl, hydroperoxyl, ureido, carbamoyl, carbamino, carbonyl, amino, hydroxamino, formamido, formyl, guanyl, cyano, cyanamino, isocyano, isocyanato, diazo, azido, diazanyl, triazano, nitrilo, nitro, nitroso, isonitroso, nitrosamino, imido, nitrosimino, oxo, $C_1$-$C_6$ alkylthio, sulfoamino, sulfamoyl, sulfenyl, sulfhydryl, sulfinyl, sulfo, sulfonyl, thioalkoxyl, thiocyano, isothiocyano, thioformamido, halo-, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene and carbocyclic and heterocyclic moieties.

"Aryl" refers to a cyclic aromatic hydrocarbon moiety having one or two or more closed ring(s). Non-limited examples include phenyl, benzyl, naphthyl, anthracenyl, phenanthracenyl, biphenyl and the like. Aryl can be substituted or unsubstituted; when substituted, it is preferably substituted by one or more, more preferably by one, two or three substituents, which is independently selected from the group consisting of (but not limited to) halogen atom, nitro, cyano, trihaloalkyl, acyl, heteroalicyclic group, alkyl, cycloalkyl, alkenyl, alkynyl, monoalkyl- or dialkyl-amino, hydroxy, sulfhydryl, alkoxyl, alkylthio, and the like;

"Heteroaryl" refers to a monocylic or fused ring having 5-12 ring atoms, wherein 1, 2, 3 or 4 heteroatoms are selected from the group consisting of N, O and S with the rest of C atom, and the ring additionally contains completely conjugated pi-electron system. Unsubstituted heteroaryl includes, but not limited to, pyrrole, furan, thiofuran, imidazole, pyridine, oxazole, isoxazole, thiazyl, pyrazole, pyrimidine, quinoline, isoquinoline, purine, carbazole, benzofuran, benzothiophene, benzodiazole and the like. Heteroaryl can be substituted or unsubstituted; when substituted, it is preferably substituted by one or more, more preferably by one, two or three substituents, which is independently selected from the group consisting of (but not limited to) halogen atom, nitro, cyano, trihaloalkyl, acyl, heteroalicyclic group, alkyl, cycloalkyl, alkenyl, alkynyl, amino, monoalkyl- or dialkyl-amino, hydroxy, sulfhydryl, alkoxyl, alkylthio and the like;

Heteroalicyclic group refers to a monocylic or fused ring having 5 to 9 ring atoms in the ring, wherein 1, 2, or 3 ring atoms are heteroatoms selected from the group consisting of N, O and $S(O)_m$, wherein m is a integer from 0 to 2, and the rest are C atom. These rings may have 0, 1 or more double bonds, which does not have completely conjugated pi-electron system. Unsubstituted heteroalicyclic group includes, but not limited to, pyrrolidinyl, piperidino, piperazino, morpholino, thiomorpholino, homopiperazino and the like. Heteroalicyclic group may be substituted or unsubstituted; when substituted, the substituent is preferably one or two or more, and more preferably one or two or three, and more preferably one or two, which includes, but not limited to, lower alkyl, trihaloalkyl, halogen, hydroxy, alkoxyl, sulfhydryl, alkylthio, cyano, acyl, thioacyl, O-carbamoyl, N-carbamoyl, O-thiocarbamyl, N-thiocarbamyl, C-amido, N-amido, nitro, N-sulfonamido, S-sulfonamido. Preferably, the heteroalicyclic group is optionally substituted by one or two substituents, which includes, but not limited to, halogen, lower alkyl, trihaloalkyl, hydroxy, sulfhydryl, cyano, N-amido, monoalkyl- or dialkyl-amino, carboxyl or N-sulfonamido;

Halogen atom refers to fluorine, chlorine, bromine or iodine group;

Trihaloalkyl refers to —$CX_3$ group, wherein X is a halogen atom defined above;

Aliphatic ring refers to a ring group having 3 to 9 carbon atoms, wherein these rings may have 0, 1, or more double bonds, while do not have completely conjugated pi-electron system. The aliphatic ring can be substituted or unsubstituted, wherein the substituent is preferably one or two or more, and more preferably is one, two or three, and more preferably is one or two, which is independently selected from the group consisting of (but not limited to) halogen atom, nitro, cyano, trihaloalkyl, acyl, heteroalicyclic group, alkyl, cycloalkyl, alkenyl, alkynyl, amino, monoalkyl- or dialkyl-amino, hydroxy, sulfhydryl, alkoxyl, alkylthio and the like;

Heterocyclic ring refers to a ring having 5 to 9 ring atoms, wherein 1, 2, or 3 ring atoms are heteroatoms selected from the group consisting of N, O and $S(O)_m$, wherein m is an integer from 0 to 2, and the rest are C atoms. These rings may have 0, 1 or more double bonds, while do not have completely conjugated pi-electron system. Unsubstituted heterocyclic ring includes, but not limited to, pyrrolidine, piperidine, piperazine, morpholine, thiomorpholine, homopiperazine and the like. Heterocyclic ring may be substituted or unsubstituted; when substituted, the substituent is preferably one or two or more, and more preferably one or two or three, and more preferably one or two, which includes, but not limited to, lower alkyl, trihaloalkyl, halogen, hydroxy, alkoxyl, sulfhydryl, alkylthio, cyano, acyl, thioacyl, O-carbamoyl, N-carbamoyl, O-thiocarbamyl, N-thiocarbamyl, C-amido, N-amido, nitro, N-sulfonamido, S-sulfonamido. Preferably, the heterocyclic ring is optionally substituted by one or two substituents, which includes, but not limited to, halogen, lower alkyl, trihaloalkyl, hydroxy, sulfhydryl, cyano, N-amido, monoalkyl- or dialkyl-amino, carboxyl or N-sulfonamido;

Aromatic ring refers to a cyclic aromatic hydrocarbon moiety having one or two or more closed ring(s). Examples include, but not limited to, benzene, naphthalene, anthracene, phenanthrene and the like. Aromatic ring can be substituted or unsubstituted; when substituted, it is preferably substituted by one or more, more preferably by one, two or three substituents, which is independently selected from the group consisting of (but not limited to) halogen atom, nitro, cyano, trihaloalkyl, acyl, heteroalicyclic group, alkyl, cycloalkyl, alkenyl, alkynyl, monoalkyl- or dialkyl-amino, hydroxy, sulfhydryl, alkoxyl, alkylthio and the like;

Heteroaromatic ring refers to a monocyclic or fused ring having 5-12 ring atoms, wherein 1, 2, 3 or 4 ring atoms are hetero atoms selected from the group consisting of N, O and S, and the rest are C atoms, and the ring additionally contains completely conjugated pi-electron system. Unsubstituted heteroaromatic ring includes, but not limited to, pyrrole, furan, thiophene, imidazole, pyridine, oxazole, isoxazole, thiazyl, pyrazole, pyrimidine, quinoline, isoquinoline, purine, carbazole, benzofuran, benzothiophene, benzodiazole and the like. Heteroaromatic ring can be substituted or unsubstituted; when substituted, it is preferably substituted by one or more, more preferably by one, two or three substituents, which are independently selected from the group consisting of (but not limited to) halogen atom, nitro, cyano, trihaloalkyl, acyl, heteroalicyclic group, alkyl, cycloalkyl, alkenyl, alkynyl, amino, monoalkyl- or dialkyl-amino, hydroxy, sulfhydryl, alkoxyl, alkylthio and the like.

The compounds provided herein further comprise the pharmaceutically acceptable equivalent of the compound or a mixture thereof Preferably, the pharmaceutically acceptable equivalent of the compound provided herein may include one of the pharmaceutically acceptable salts, hydrate, solvate, metabolite, prodrug and isostere, or a mixture thereof Preferably, among the pharmaceutically acceptable equivalents of the compound provided herein, the pharmaceutically acceptable salts comprise the acid salts or basic salts of the compound provided herein. The pharmaceutically acceptable salts have pharmaceutical activity of the compound, and meet the demand in both biological and practical applications.

Among the pharmaceutically acceptable equivalents of the compound provided herein, the pharmaceutically acceptable acid salts include, but not limited to, acetate, sulphate, phosphate, formate, propionate, adipate, succinate, tartrate, alginate, aspartate, benzoate, tosylate, mesylate, benzene sulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate.

Preferably, among the pharmaceutically acceptable equivalents of the compound provided herein, the pharmaceutically acceptable basic salts may include ammonium salts, alkali metal salts such as sodium and potassium salts, alkaline earth metal salts such as calcium and magnesium salts, salts with organic bases such as dicyclohexylamine, N-methyl-D-glucamine, and salts with amino acids such as arginine and lysine. Preferably, the basic nitrogen-containing groups can be quarternized with agents including, but not limited to, lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenyl bromides.

Preferably, among the pharmaceutically acceptable equivalents of the compound provided herein, prodrug refers to a derivative of the compounds according to the present invention that undergoes biotransformation, such as metabolism, before exhibiting its pharmacological effect. The prodrug is formulated with the materials of improved chemical stability, improved patient acceptance and compliance, improved bioavailabihty, prolonged duration of action, improved organ selectivity, improved formulation (e.g., increased hydrosolubility), or decreased side effects (e.g., toxicity). The prodrug can be readily prepared from the compounds according to the present invention using conventional means, see for example BURGER'S MEDICINAL CHEMISTRY AND DRUG CHEMISTRY, Fifth Ed., Vol. 1, pp. 172-178, 949-982 (1995).

In the present invention, isostere refers to elements, functional groups, substituents, molecules or ions having different molecular formulae but exhibiting similar or identical physical properties. For example, tetrazole is an isostere of carboxylic acid because it mimics the properties of carboxylic acid even though they have different molecular formulae. Typically, two isosteric molecules have similar or identical sizes and shapes. Ideally, isosteric molecules should be isomorphic and able to co-crystallize. Other physical properties that isosteric molecules usually share include boiling point, density, viscosity and thermal conductivity. However, certain properties may be different: dipolar moments, polarity, polarization, size and shape since the external orbitals may be hybridized differently. Isosteres encompasses bioisosteres. Bioisosteres are isosteres that, in addition to their physical similarities, share some common biological properties. Typically, bioisosteres interact with the same recognition site or produce broadly similar biological effects.

In the present invention, effective amount refers to the amount required to produce a desired effect, for example: regulating calcium homeostasis, treating a disease in which dysregulation of calcium homeostasis is implicated, treating a cardiovascular disease, stroke, or dementia, or inhibiting acetylcholinesterase or L-type calcium channel.

In the present invention, metabolite refers to a substance produced by metabolism or by a metabolic process.

The present invention provides use of 1,4-dihydro-naphthyridine derivative in preparing a medicament as calcium channel inhibitor and acetylcholinesterase inhibitor.

The invention also provides use of 1,4-dihydro-naphthyridine derivative in preparing a medicament for regulating calcium homeostasis, treating a cardiovascular disease, cerebrovascular disease or treating dementia.

Among others, dementia is preferably Alzheimer's disease or vascular dementia.

In the examples of the present invention, the activity of blocking L-type $Ca^{2+}$ channel by 1,4-dihydro-naphthyridine derivatives was detected by the inventors using patch clamp technique and high content screening analysis. The results showed that strong activities of blocking L-type $Ca^{2+}$ channel were common among 1,4-dihydro-naphthyridine derivatives, and were higher than the activities of the positive control Nifedipine and Nimodipine.

In examples of the present invention, the activities of inhibiting acetylcholinesterase by 1,4-dihydro-naphthyridine derivatives were detected by the inventor. The results indicated that 1,4-dihydro-naphthyridine derivatives were capable of inhibiting the activity of acetylcholinesterase.

Based on the experimental results above, the compounds according to the present invention not only can inhibit the activity of acetylcholinesterase, but also can block the influx of extracellular calcium ions into cells through the calcium channel, i.e., has dual-activities.

Based on the examples of preparation and effect together with the knowledge in the art, it can be inferred that when the substituent R in the general formula of the present invention is an aryl or heteroaryl, and any positions in the aryl or heteroaryl is substituted by halogen atom, hydroxy, cyano, alkyl, cycloalkyl, alkenyl, alkynyl and the like, or form a ring, the resulting compounds have identical or similar effects, and can be prepared simply and readily. Among others, any position on the alkyl, cycloalkyl, alkenyl, alkynyl can be substituted by a substituent or any —$CH_2$— thereof can be replaced.

Based on the examples of preparation and effect together with the knowledge in the art, it can be inferred that when the substituent $R_1$ in the general formula of the present invention is hydrogen, hydroxy, aryl, heteroaryl, $C_1$-$C_8$ alkyl, $C_3$-$C_8$ cycloalkyl, $C_2$-$C_8$ alkenyl or $C_2$-$C_8$ alkynyl, and any position on the $C_1$-$C_8$ alkyl, $C_3$-$C_8$ cycloalkyl, $C_2$-$C_8$ alkenyl or $C_2$-$C_8$ alkynyl is substituted by a substituent or any —$CH_2$— thereof is replaced, the resulting compounds have identical or similar effects, and can be prepared simply and readily.

Based on the examples of preparation and effect together with the knowledge in the art, it can be inferred that when the substituent $R_2$ in the general formula of the present invention is hydrogen, halogen atom, nitro, amino, hydroxy, trihaloalkyl, $C_1$-$C_8$ alkyl, $C_3$-$C_8$ cycloalkyl, $C_2$-$C_8$ alkenyl or $C_2$-$C_8$ alkynyl, and any position on the $C_1$-$C_8$ alkyl, $C_3$-$C_8$ cycloalkyl, $C_2$-$C_8$ alkenyl or $C_2$-$C_8$ alkynyl is substituted by a substituent or any —$CH_2$— thereof is replaced, the resulting compounds have identical or similar effects, and can be prepared simply and readily.

Based on the examples of preparation and effect together with the knowledge in the art, it can be inferred that when the substituent $R_3$ in the general formula of the present invention is hydrogen, $C_1$-$C_8$ alkyl or $C_3$-$C_8$ cycloalkyl, and any position on the $C_1$-$C_8$ alkyl or $C_3$-$C_8$ cycloalkyl is substituted by a substituent or any —$CH_2$— thereof is replaced, the resulting compounds have identical or similar effects, and can be prepared simply and readily.

Based on the examples of preparation and effect together with the knowledge in the art, it can be inferred that when the substituent Y in the general formula of the present invention is $C_2$-$C_8$ alkenylene, $C_2$-$C_8$ alkynylene or non-hydrogen substituted $C_2$-$C_8$ alkylene, and any position on the $C_2$-$C_8$ alkenylene, $C_2$-$C_8$ alkynylene or non-hydrogen substituted $C_2$-$C_8$ alkylene is substituted by a substituent or any —$CH_2$— thereof is replaced, or any two positions form a ring the resulting compounds have identical or similar effects, and can be prepared simply and readily.

Based on the examples of preparation and effect together with the knowledge in the art, it can be inferred that when the substituent X in the present general formula of the present invention is —O— or —$NR_7$—, the resulting compounds have identical or similar effects, and can be prepared simply and readily. Among others, $R_7$ is hydrogen, aryl, heteroaryl, $C_1$-$C_8$ alkyl, $C_3$-$C_8$ cycloalkyl, $C_2$-$C_8$ alkenyl, or $C_2$-$C_8$ alkynyl.

The present invention also provides a pharmaceutical composition, comprising a 1,4-dihydro-naphthyridine derivative, pharmaceutically acceptable equivalent or a mixture thereof, and a pharmaceutically acceptable carrier.

The compounds of the general formula according to the present invention can be synthesized based on the following routes:

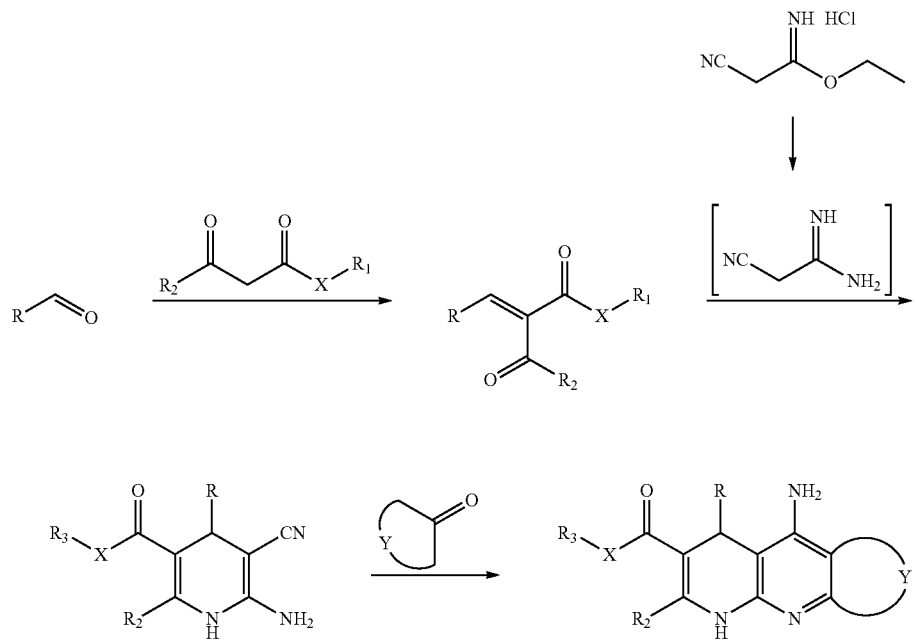

Detailed Description

In the present invention, 1,4-dihydro-naphthyridine derivative and a pharmaceutical composition thereof and use thereof are disclosed, which can be achieved through appropriate improvements to the process parameters by those skilled in the art with reference to the contents herein. Particularly, it should be noted that all similar replacements and modifications are apparent to those skilled in the art, all of which are regarded to be included in the present invention. The method of the present invention and the applications thereof will be described by preferred examples, and it is apparent that modification, or proper change and the combination thereof can be made to the method and applications described herein by those skilled in the art, without departing from the content, spirit and scope of the invention, in order to achieve and apply the techniques disclosed in the present invention.

The present invention will be further described with reference to the specific examples below, in order to make the technical solutions of the present invention better understood by those skilled in the art.

The compounds prepared in the present examples are as follows:

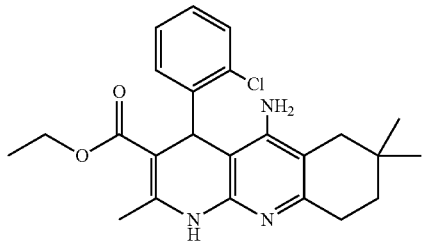

Compound 1: 5-amino-4-(2-chlorphenyl)-2,7,7-trimethyl-1,4,6,7,8,9-hexahydrobenzo[b][1,8]naphthyridine-3-carboxylic acid ethyl ester, as shown by S1

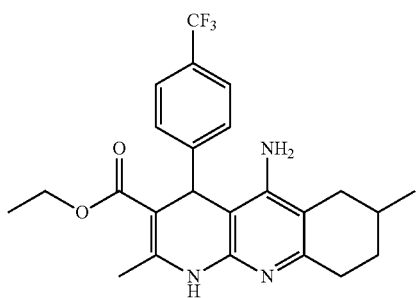

Compound 2: 5-amino-2,7-dimethyl-4-(4-trifluoromethylphenyl)-1,4,6,7,8,9-hexahydrobenzo[b][1,8]naphthyridine-3-carboxylic acid ethyl ester, as shown by S2

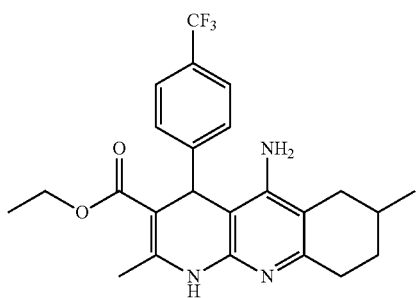

Compound 3: 5-amino-4-(3-fluorophenyl)-2,7,7-trimethyl-1,4,6,7,8,9-hexahydrobenzo[b][1,8]naphthyridine-3-carboxylic acid isopropyl ester, as shown by S3

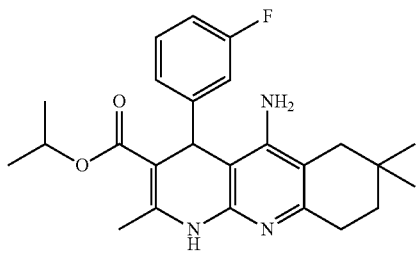

Compound 4: 5-amino-4-(3-trifluoromethylphenyl)-2,7,7-trimethyl-1,4,6,7,8,9-hexahydrobenzo[b][1,8]naphthyridine-3-carboxylic acid ethyl ester, as shown by S4

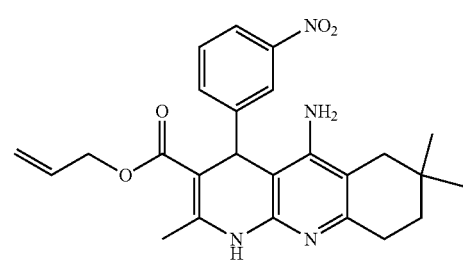

Compound 5: 5-amino-4-(3-nitrophenyl)-2,7,7-trimallyl1,4,6,7,8,9-hexahydrobenzo[b][1,8]naphthyridine-3-carboxylic acid allyl ester, as shown by S5

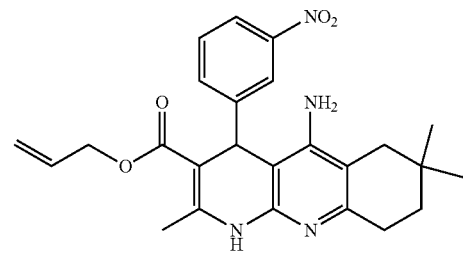

Compound 6: 5-amino-4-(3-chlorphenyl)-2,7,7-trimethyl-1,4,6,7,8,9-hexahydrobenzo[b][6,8]naphthyridine-3-carboxylic acid ethyl ester, as shown by S6

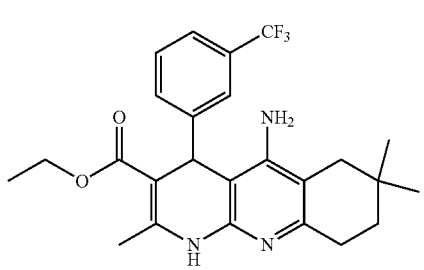

Compound 7: 5-amino-4-phenyl-2,7,7-trimethyl-1,4,6,7,8,9-hexahydrobenzo[b][1,8]naphthyridine-3-carboxylic acid methyl ester, as shown by S7

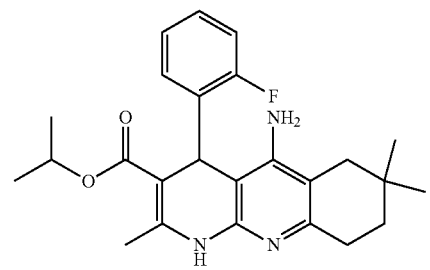

Compound 8: 5-amino-4-(2-fluorophenyl)-2,7,7-trimethyl-1,4,6,7,8,9-hexahydrobenzo[b][1,8]naphthyridine-3-carboxylic acid isopropyl ester, as shown by S8

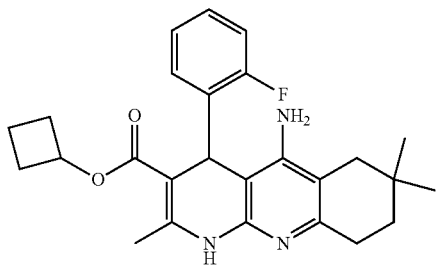

Compound 9: 5-amino-4-(2-fluorophenyl)-2,7,7-trimethyl-1,4,6,7,8,9-hexahydrobenzo[b][1,8]naphthyridine-3-carboxylic acid cyclobutyl ester, as shown by S9

Compound 10: 5-amino-4-(2-chlorphenyl)-2,7,7-trimethyl-1,4,6,7,8,9-hexahydrobenzo[b][1,8]naphthyridine-3-carboxylic acid methoxyethyl ester, as shown by S10

Compound 11: 5-amino-4-(2-chlorphenyl)-2,7,7-trimethyl-1,4,6,7,8,9-hexahydrobenzo[b][1,8]naphthyridine-3-carboxylic acid cyclopropylmethyl ester, as shown by S11

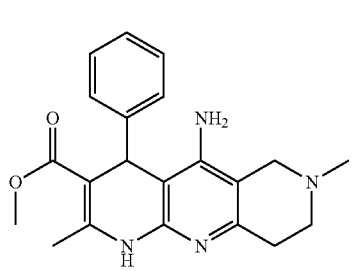

Compound 12: 5-amino-2,7-dimethyl-4-phenyl-1,4,6,7,8,9-hexahydropyrido[2,3-b][1,6]naphthyridine-3-carboxylic acid methyl ester, as shown by S12

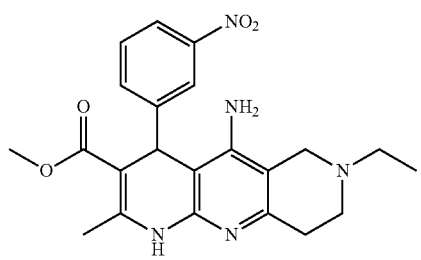

Compound 13: 5-amino-2-methyl-4-(3-nitrophenyl)-7-ethyl-1,4,6,7,8,9-hexahydropyrido[2,3-b][1,6]naphthyridine-3-carboxylic acid methyl ester, as shown by S13

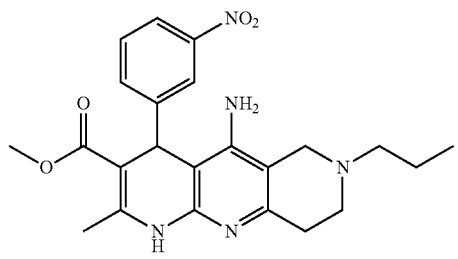

Compound 14: 5-amino-2-methyl-4-(3-nitrophenyl)-7-propyl-1,4,6,7,8,9-hexahydropyrido[2,3-b][1,6]naphthyridine-3-carboxylic acid methyl ester, as shown by S14

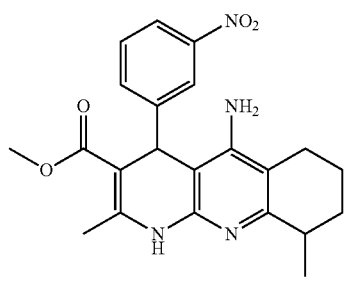

Compound 15: 5-amino-4-(3-nitrophenyl)-2,9-dimethyl-1,4,6,7,8,9-hexahydrobenzo[b][1,8]naphthyridine-3-carboxylic acid methyl ester, as shown by S15

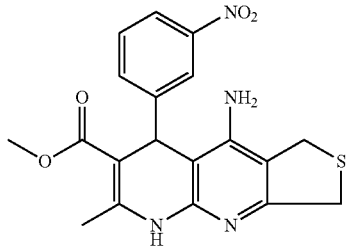

Compound 16: 5-amino-2-methyl-4-(3-nitrophenyl)-1,4,6,8-tetrahydrothieno[3,4-b][1,8]naphthyridine-3-carboxylic acid methyl ester, as shown by S16

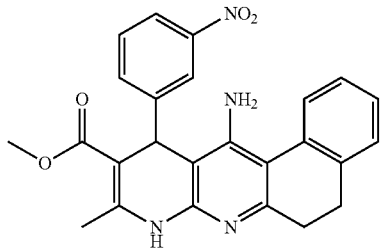

Compound 17: 12-amino-9-methyl-11-(3-nitrophenyl)-5,6,8,11-tetrahydronaphtho[2,1-b][1,8]naphthyridine-10-carboxylic acid methyl ester, as shown by S17

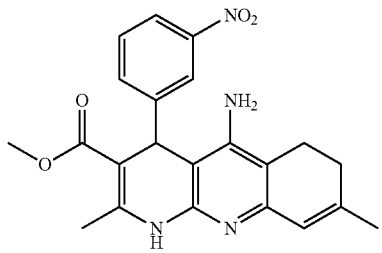

Compound 18: 5-amino-2,8-dimethyl-4-(3-nitrophenyl)-1,4,6,7-tetrahydrobenzo[b][1,8]naphthyridine-3-carboxylic acid methyl ester, as shown by S18

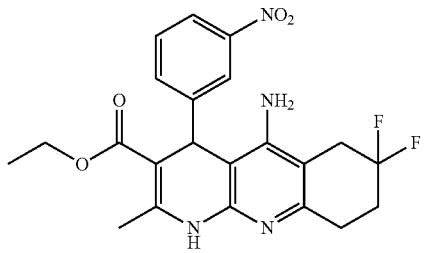

Compound 19: 5-amino-7,7-difluoro-2-methyl-4-(3-nitrophenyl)-1,4,6,7,8,9-hexahydrobenzo[b][1,8]naphthyridine-3-carboxylic acid ethyl ester, as shown by S19

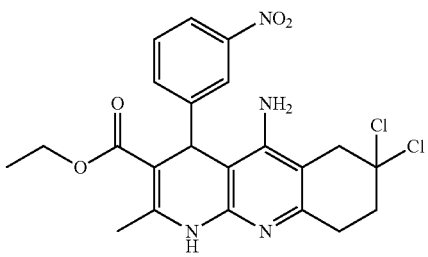

Compound 20: 5-amino-7,7-dichloro-2-methyl-4-(3-nitrophenyl)-1,4,6,7,8,9-hexahydrobenzo[b][1,8]naphthyridine-3-carboxylic acid ethyl ester, as shown by S20

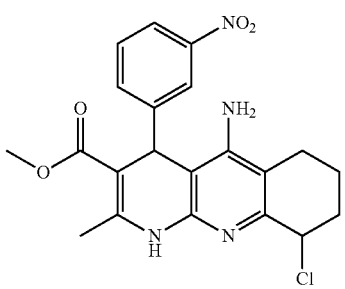

Compound 21: 5-amino-9-chloro-2-methyl-4-(3-nitrophenyl)-1,4,6,7,8,9-hexahydrobenzo[b][1,8]naphthyridine-3-carboxylic acid methyl ester, as shown by S21

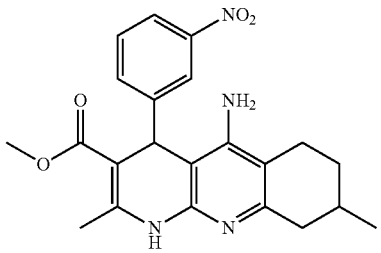

Compound 22: 5-amino-2,8-dimethyl-4-(3-nitrophenyl)-1,4,6,7,8,9-hexahydrobenzo[b][1,8]naphthyridine-3-carboxylic acid methyl ester, as shown by S22

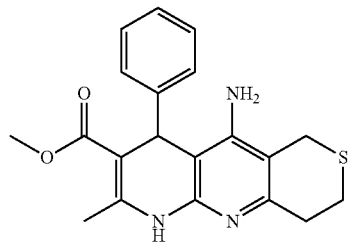

Compound 23: 5-amino-2-methyl-4-phenyl-4,6,8,9-tetrahydro-1H-thiopyrano[4,3-b][1,8]naphthyridine-3-carboxylic acid methyl ester, as shown by S23

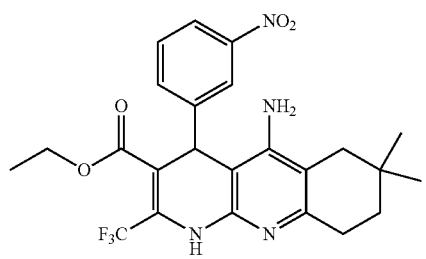

Compound 24: 5-amino-7,7-dimethyl-4-(3-nitrophenyl)-2-trifluoromethyl-1,4,6,7,8,9-hexahydrobenzo[b][1,8]naphthyridine-3-carboxylic acid ethyl ester, as shown by S24

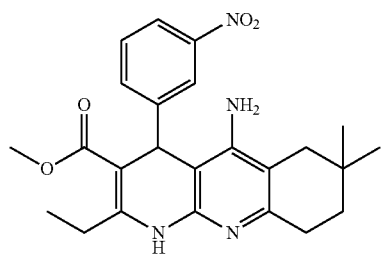

Compound 25: 5-amino-7,7-dimethyl-4-(3-nitrophenyl)-2-ethyl-1,4,6,7,8,9-hexahydrobenzo[b][1,8]naphthyridine-3-carboxylic acid methyl ester, as shown by S25

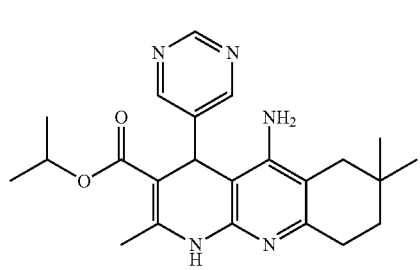

Compound 26: 5-amino-2,7,7-trimethyl-4-(pyrimidin-5-yl)-1,4,6,7,8,9-hexahydrobenzo[b][1,8]naphthyridine-3-carboxylic acid isopropyl ester, as shown by S26

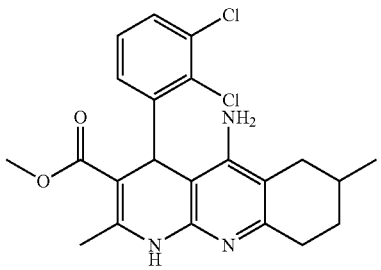

Compound 27: 5-amino-4-(2,3-dichlorophenyl)-2,7-dimethyl-1,4,6,7,8,9-hexahydrobenzo[b][1,8]naphthyridine-3-carboxylic acid methyl ester, as shown by S27

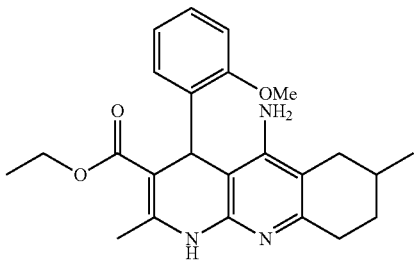

Compound 28: 5-amino-4-(2-methoxylphenyl)-2,7-dimethyl-1,4,6,7,8,9-hexahydrobenzo[b][1,8]naphthyridine-3-carboxylic acid ethyl ester, as shown by S28

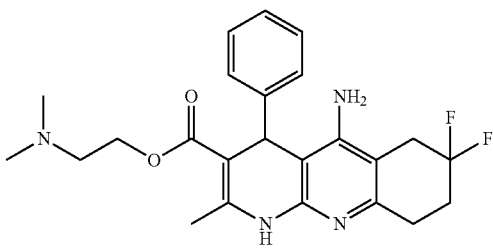

Compound 29: 5-amino-7,7-difluoro-2-methyl-4-phenyl-1,4,6,7,8,9-hexahydrobenzo[b][1,8]naphthyridine-3-carboxylic acid-2-(dimethylamino) ethyl ester, as shown by S29

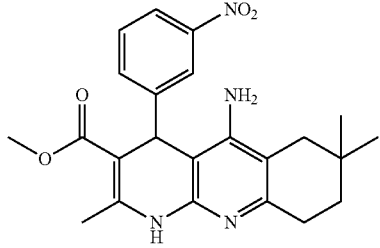

Compound 30: 5-amino-2,7,7-trimethyl-4-(3-nitrophenyl)-1,4,6,7,8,9-hexahydrobenzo[b][1,8]naphthyridine-3-carboxylic acid methyl ester, as shown by S30

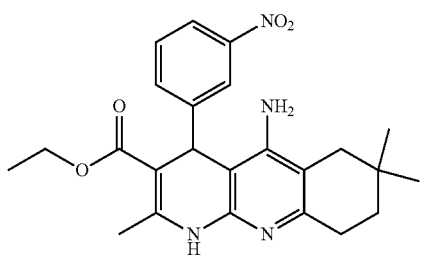

Compound 31: 5-amino-2,7,7-trimethyl-4-(3-nitrophenyl)-1,4,6,7,8,9-hexahydrobenzo[b][1,8]naphthyridine-3-carboxylic acid ethyl ester, as shown by S31

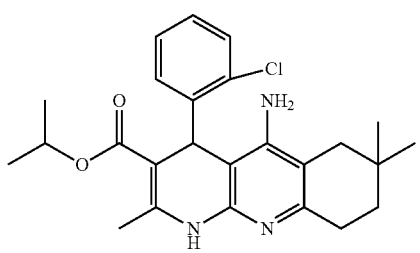

Compound 32: 5-amino-2,7,7-trimethyl-4-(2-chlorphenyl)-1,4,6,7,8,9-hexahydrobenzo[b][1,8]naphthyridine-3-carboxylic acid isopropyl ester, as shown by S32

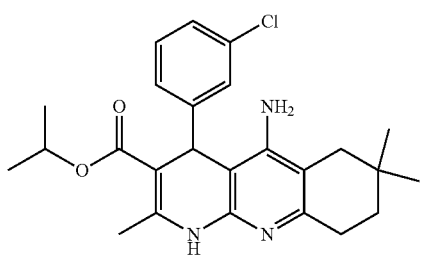

Compound 33: 5-amino-2,7,7-trimethyl-4-(3-chlorphenyl)-1,4,6,7,8,9-hexahydrobenzo[b][1,8]naphthyridine-3-carboxylic acid isopropyl ester, as shown by S33

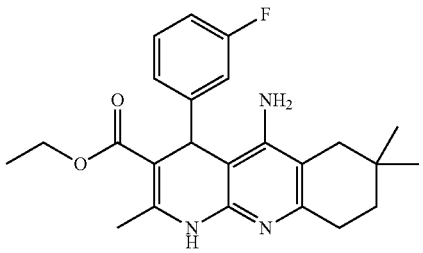

Compound 34: 5-amino-2,7,7-trimethyl-4-(3-fluorophenyl)-1,4,6,7,8,9-hexahydrobenzo[b][1,8]naphthyridine-3-carboxylic acid ethyl ester, as shown by S34

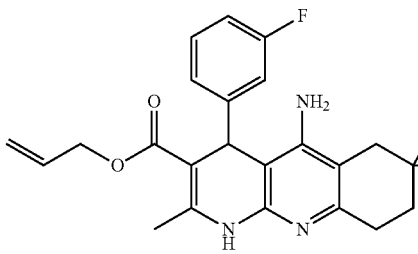

Compound 35: 5-amino-4-(3-fluorophenyl)-2,7,7-trimethyl-1,4,6,7,8,9-hexahydrobenzo[b][1,8]naphthyridine-3-carboxylic acid allyl ester, as shown by S35

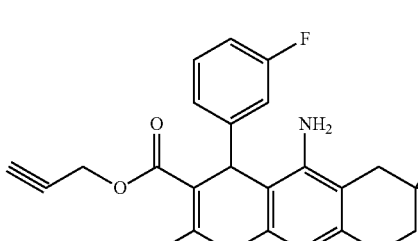

Compound 36: 5-amino-2,7,7-trimethyl-4-(3-fluorophenyl)-1,4,6,7,8,9-hexahydrobenzo[b][1,8]naphthyridine-3-carboxylic acid propargyl ester, as shown by S36

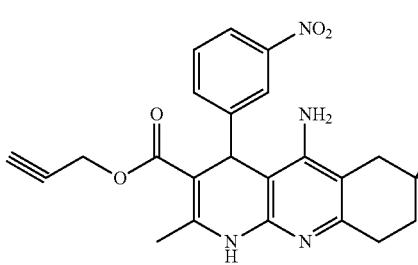

23

Compound 37: 5-amino-4-(3-nitrophenyl)-2,7,7-trimethyl-1,4,6,7,8,9-hexahydrobenzo[b][1,8]naphthyridine-3-carboxylic acid propargyl ester, as shown by S37

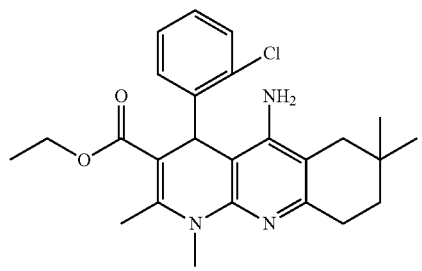

Compound 38: 5-amino-4-(2-chlorphenyl)-1,2,7,7-tetramethyl-1,4,6,7,8,9-hexahydrobenzo[b][1, 8]naphthyridine-3-carboxylic acid ethyl ester, as shown by S38

EXAMPLE 1

Synthesis of Compound S1

Synthetic Route:

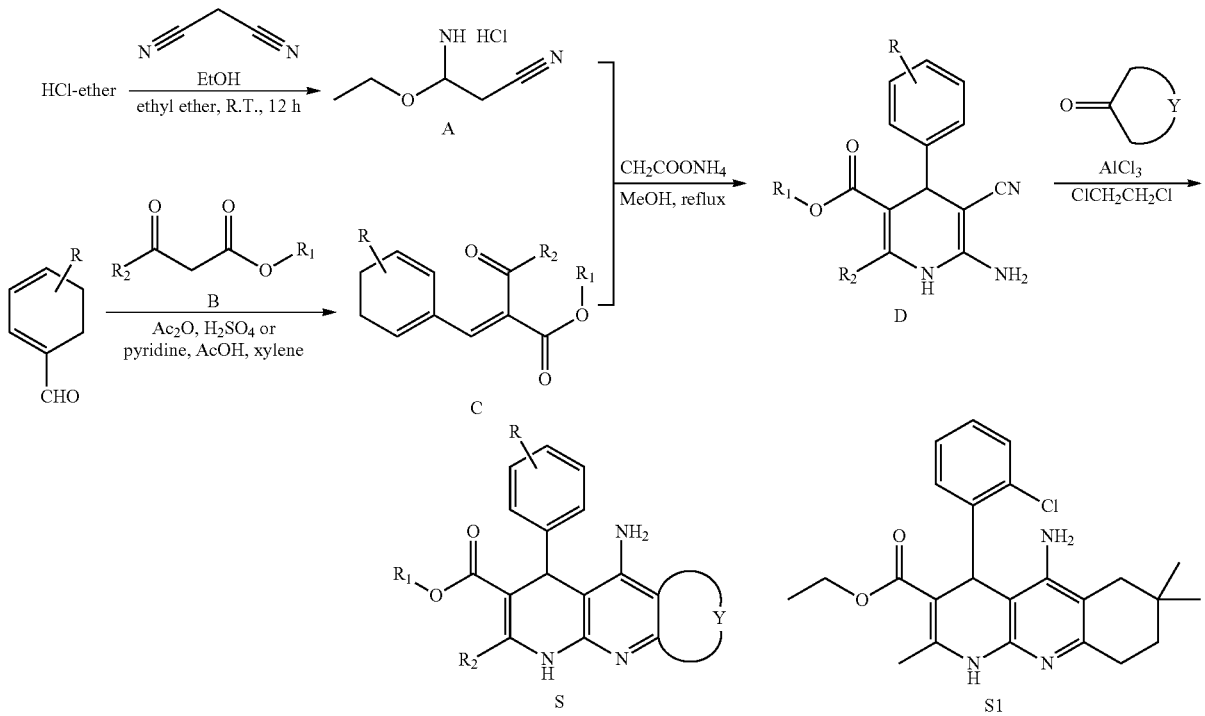

Step 1 Synthesis of Raw Material A 6.64 g malononitrile (10.06 mmol) and 4.63 g anhydrous alcohol (10.06 mmol) were mixed and homogeneously stirred at room temperature in a reaction bottle, followed by addition of hydrochloric acid solution in ethyl ether (10.39 mmol) placed in an ice bath. The mixture was warmed up to the room temperature and stirred for 3 h, resulting in a great amount of solid precipitated. Subsequently, the mixture was maintained in a refrigerator over night, and filtered, washed and dried to give A (12.1 g), with a yield of 80.4%

ESI-MS: 113.1 [M+H]$^+$;

Step 2 Synthesis of Compound C

Ethyl acetoacetate (13.0 g, 0.1 mol) and acetic anhydride (7.5 g, 0.073 mol) were mixed, and subsequently sulphuric acid (0.8 mL) was added in an ice bath while stirring. 2-chlorobenzaldehyde (14.1 g, 0.11 mol) was then added and slowly dissolved. After stirring for 1 h, the end of reaction was monitored by TLC. Then, 5 mL water was added and the mixture was extracted by dichloromethane (20 mL×3). The organic phase was combined and washed with saturated saline solution. Subsequently, it was dried by anhydrous sodium sulfate, and concentrated. The resultant was separated by chromatography using silica gel column (petroleum ether:ethyl acetate=10:1) to give a light yellow oil product C1, with a yield of 50.4%.

Step 3 Synthesis of Intermediate D

A (2.2 g, 0.015 mol), ammonium acetate (3.3 g, 0.043 mol) and 10 ml methanol were added to a reaction bottle, stirred and refluxed for 30 min. Subsequently, C1 (3.6 g, 0.014 mol) was added and the mixture continued to reflux for another 30 min. The end of reaction was detected by TLC. The resultant product was concentrated under vacuum, and the crude product was separated by chromatography using silica gel column (petroleum ether:ethyl acetate=3:1) to give yellow powder D1 (1.4 g), with a yield of 31%.

Step 4

Intermediate D1 (110 mg, 0.35 mmol) was dissolved in 10 mL 1,2-dichloroethane, to which 4,4-dimethyl cyclohexanone (80 mg, 0.63 mmol) and AlCl$_3$ (85 mg, 0.63 mmol) were added. The mixture was refluxed by heating under nitrogen atmosphere protection over night. After confirming that the raw material had been completely comsumed by TLC, the reaction heating was stopped, allowing for cooling to room temperature. Subsequently, the reaction mixture was poured into a solution of THF: $H_2O$=1:1 (15 mL), and 10% aqueous NaOH solution was added dropwise while stirring until pH>7. The mixture was extracted by dichloromethane (15 mL×3). The organic phase was combined and washed with saturated saline solution. Subsequently, it was dried by anhydrous sodium sulfate, and concentrated. The resultant product was separated by chromatography using silica gel column (petroleum ether:ethyl acetate=3:1) to give 58.6 mg yellow oil product 51, with a yield of 40%.

ESI-MS: 426.0 [M+H]$^+$;

$^1$H NMR (400 MHz, CDCl$_3$): δ7.49 (1H, td, J=1.2, 8.0), 7.27 (1H, td, J=1.2, 8.0), 7.18 (1H, dd, J=1.6, 8.0), 7.10 (1H, dd, J=1.6, 8.0), 5.44 (1H, s), 4.62 (2H, s), 4.12 (2H, q, J=7.2), 2.72 (2H, m), 2.46 (3H, s), 2.07 (2H, m), 1.57 (2H, m), 1.22 (3H, t, J=7.2), 1.00 (6H, s).

EXAMPLE 2

Synthesis of Compound S2

Synthetic Route:

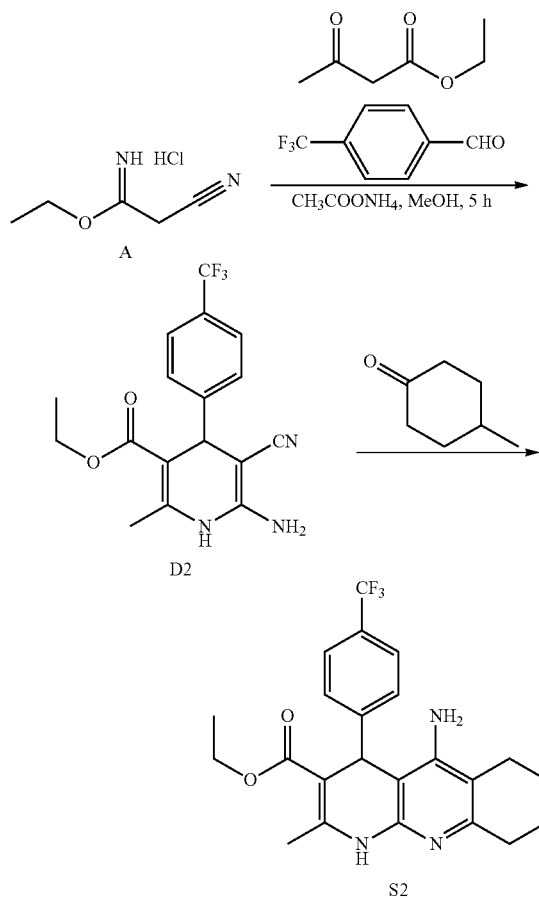

Step 1 Synthesis of Intermediate D2

P-(Trifluoromethyl)benzaldehyde (174 mg, 1.0 mmol), intermediate A (150 mg, 1.0 mmol), ethyl acetoacetate (169 mg, 1.3 mmol) and ammonium acetate (100 mg, 1.3 mmol) were precisely weighed out and placed into an 50 mL round flask, and dissolved by adding 10 mL methanol. After refluxed by heating while stirring for 5 h, the mixture was cooled to room temperature and concentrated under vacuum. The resultant product was separated by chromatography using silica gel column (petroleum ether:ethyl acetate=3:1) to give 40 mg yellow solid product C2, with a yield of 11%.

ESI-MS: 352.0 [M+H]$^+$.

Step 2

Intermediate D2 (35.1 mg, 0.1 mmol) was dissolved in 3 mL 1,2-dichloroethane, to which 4-methyl cyclohexanone (24.4 mg, 0.2 mmol) and AlCl$_3$ (26.6 mg, 0.2 mmol) were added. The mixture was refluxed by heating under the argon atmosphere over night. After confirming that the raw material had been completely comsumed by TLC, the reaction heating was stopped, allowing for cooling to room temperature. Subsequently, the reaction mixture was poured into a solution of THF: $H_2O$=1:1 (10 mL), and 10% aqueous NaOH solution was added dropwise while stirring until pH>7. The mixture was extracted by dichloromethane (10 mL×3). The organic phase was combined and washed with saturated saline solution. Subsequently, it was dried by anhydrous sodium sulfate, and concentrated. The resultant product was separated by chromatography using silica gel column (petroleum ether: ethyl acetate=3:1) to give 40 mg yellow oil product S2, with a yield of 90%.

ESI-MS: 446.0 [M+H]$^+$;

$^1$H NMR (400 MHz, CDCl$_3$): δ7.48 (4H, m), 5.09 (1H, s), 4.12 (4H, m), 2.72 (2H, m), 2.39 (3H, s), 1.89 (2H, m), 1.62 (3H, m), 1.27 (3H, m), 1.09 (3H, d, J=6.4 Hz).

EXAMPLE 3

Synthesis of Compound S3

Synthetic Route:

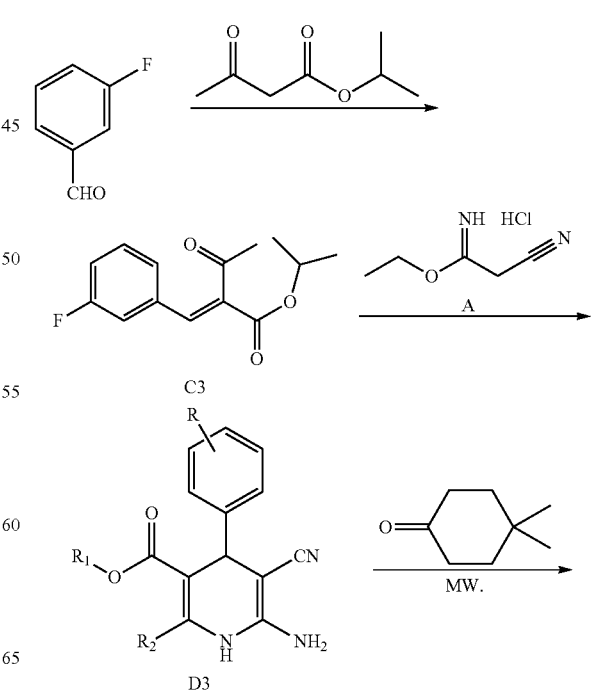

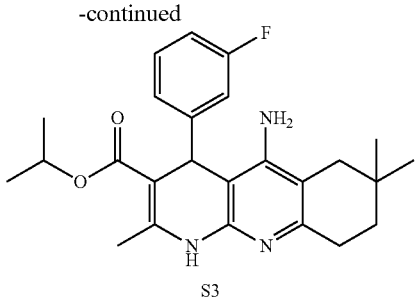

S3

Step 1

By reference to the synthesis method of D2 in Example 2, 3-fluorobenzaldehyde (1.5 g, 12.1 mmol), isopropyl acetoacetate (2.26 g, 15.7 mmol), intermediate A (1.8 g, 12.1 mmol) and ammonium acetate (1.2 g, 15.7 mmol) were reacted to give 200 mg yellow solid—target intermediate D3, with a yield of 6%.

Step 2 (Microwave-Assisted Reaction)

Intermediate D3 (80 mg, 0.254 mmol) was placed into a microwave reaction tube, and dissolved in 3 mL 1,2-dichloroethane, to which 4,4-dimethyl cyclohexanone (64 mg, 0.508 mmol) and $AlCl_3$ (67.5 mg, 0.508 mmol) were added. The mixture was reacted in a microwave reaction device with temperature T=120° C. for time t=1 h. After confirming the raw material had been comsumed by TLC, the reaction was stopped, and allowed for cooling to room temperature. Subsequently, the reaction mixture was poured into a solution of THF: $H_2O$=1:1 (10 mL), and 10% aqueous NaOH solution was added dropwise while stirring until pH>7. The mixture was extracted by dichloromethane (10 mL×3). The organic phase was combined and washed with saturated saline solution. Subsequently, it was dried by anhydrous sodium sulfate, and concentrated. The resultant product was separated by chromatography using silica gel column (petroleum ether:ethyl acetate=3:1) to give 32 mg yellow oil product S3, with a yield of 30%.

ESI-MS: 424.3 $[M+H]^+$;

$^1$H NMR (400 MHz, DMSO-$d_6$): δ9.17 (1H, s), 7.18 (2H, m), 7.10 (1H, m), 6.89 (1H, m), 5.38 (2H, br s), 5.01 (1H, s), 4.81 (1H, m), 2.56 (2H, m), 2.28 (3H, s), 2.14 (1H, d, J=16 Hz), 2.02 (1H, d, J=16 Hz), 1.48 (2H, t, J=6.6 Hz), 1.21 (3H, d, J=6.0 Hz), 1.07 (3H, d, J=6.0 Hz), 0.95 (6H, s).

EXAMPLE 4

Synthesis of Compound S4

Synthetic Route:

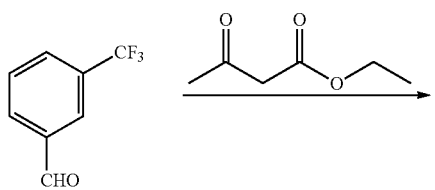

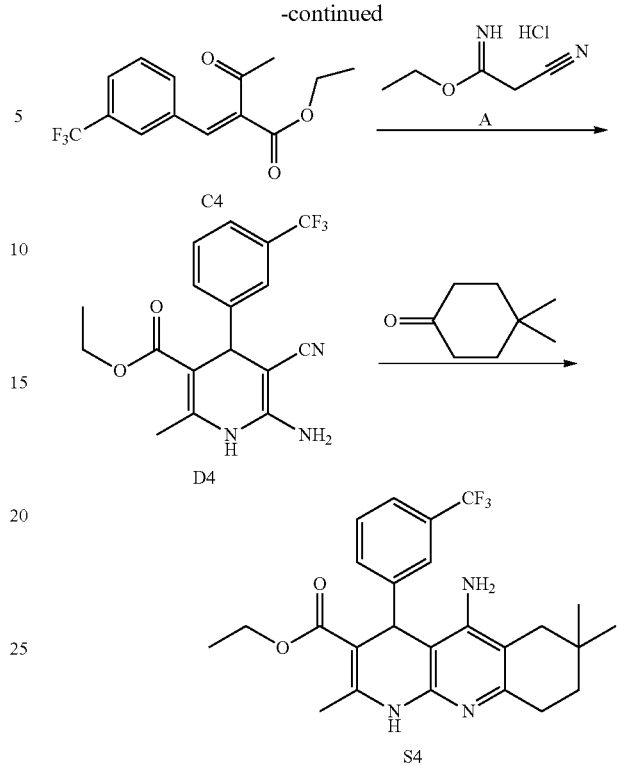

Step 1

Using the synthesis route of Example 1, ethyl acetoacetate (1.95 g, 0.015 mol) was precisely weighed out and dissolved in 30 ml toluene, to which m-trifluoromethyl benzaldehyde (2.61 g, 0.015 mol) was added. 3 drops of piperidine was slowly added dropwise while stirring, with further stirring for 2 min. Subsequently, 3 drops of acetic acid was added dropwise, and the system was stirred continuously with a great amount of white smoke generated. After the reaction was steady, the above reaction system was placed into a 95° C. oil bath for refluxed under heating. The reaction was detected by TLC. After 4 h, the reaction was stopped, cooled, and concentrated under vacuum. The crude product was separated by chromatography using silica gel column (petroleum ether: ethyl acetate=10:1) to give 3.4 g light yellow oil product C4, with a yield of 80%.

Step 2

By reference to the synthesis of intermediate D1 in Example 1, the reaction among the intermediate C4 (3.4 g, 0.012 mol), A (1.78 g, 0.012 mol) and ammonium acetate (2.77 g, 0.036 mol) was performed to give 1.39 g intermediate D4, with a yield of 33%, ESI-MS: 352.1 $[M+H]^+$.

Step 3

By reference to the synthesis of S1 in Example 1, intermediate D4 (100 mg, 0.28 mmol), 4,4-dimethyl cyclohexanone (215 mg, 1.70 mmol) and aluminium trichloride (75 mg, 0.56 mmol) were reacted to give 60 mg white solid compound S4, with a yield of 42%.

ESI-MS: 460.3 $[M+H]^+$;

$^1$H NMR (400 MHz, $CDCl_3$): δ7.33-7.61 (4H, m), 5.00 (1H, s), 4.12 (2H, m), 4.00 (2H, s), 2.71 (2H, m), 2.38 (3H, s), 2.05 (2H, m), 1.58 (2H, t, J=6.8), 1.26 (3H, m), 0.99 (6H, d, J=3.2).

EXAMPLE 5

Synthesis of Compound S5

Synthetic Route:

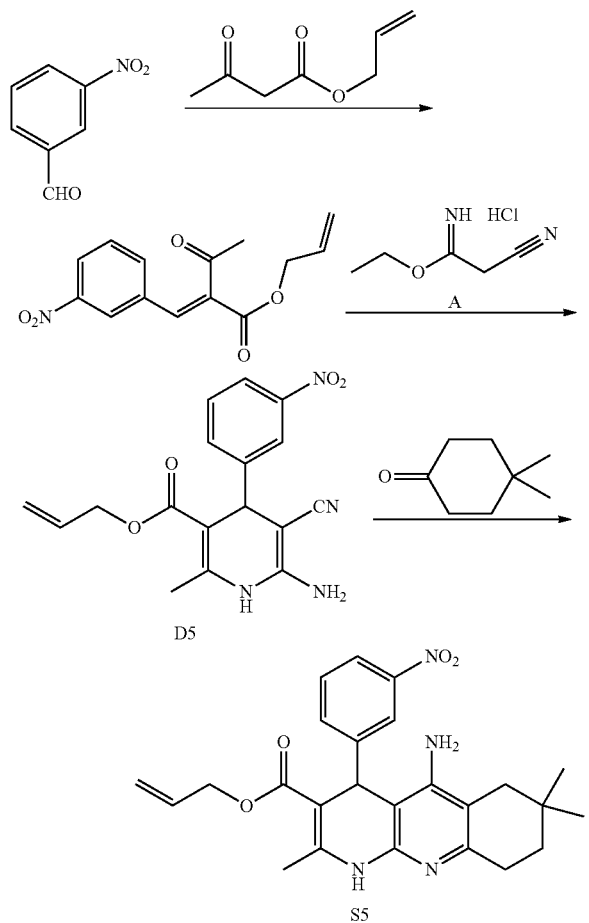

Step 1

By reference to the synthesis of compound D4 in Example 4, using the route in Example 1, a two-step reaction was carried out by using allyl acetoacetate (0.03 mol), 3-nitrobenzaldehyde (0.03 mol) and ammonium acetate (0.072 mol) and raw material A (0.026 mol) to give 2.85 g yellow solid intermediate D5, with an overall yield of 28%.

Step 2

By reference to the synthesis of S3 in Example 3, microwave-assisted reaction was carried out by using the intermediate D5 (200 mg, 0.58 mmol), 4,4-dimethyl cyclohexanone (370 mg, 2.93 mmol) and aluminium trichloride (195 mg, 1.46 mmol) to give 100 mg yellow solid compound S5, with a yield of 38%.

ESI-MS: 449.2 [M+H]$^+$; ESI-MS: 447.2 [M−H]$^-$;

$^1$H NMR (400 MHz, CDCl$_3$): δ8.02 (1H, m), 8.06 (1H, m), 7.68 (1H, d, J=8.0), 7.43 (1H, t, J=8.0), 5.94 (1H, m), 5.24 (2H, m), 5.16 (1H, s), 4.60 (2H, m), 4.14 (2H, s), 2.75 (2H, m), 2.44 (3H, s), 2.02-2.13 (2H, m), 1.60 (2H, t, J=7.2), 1.02 (6H, d, J=2.0).

EXAMPLE 6

Synthesis of Compound S6

Synthetic Route:

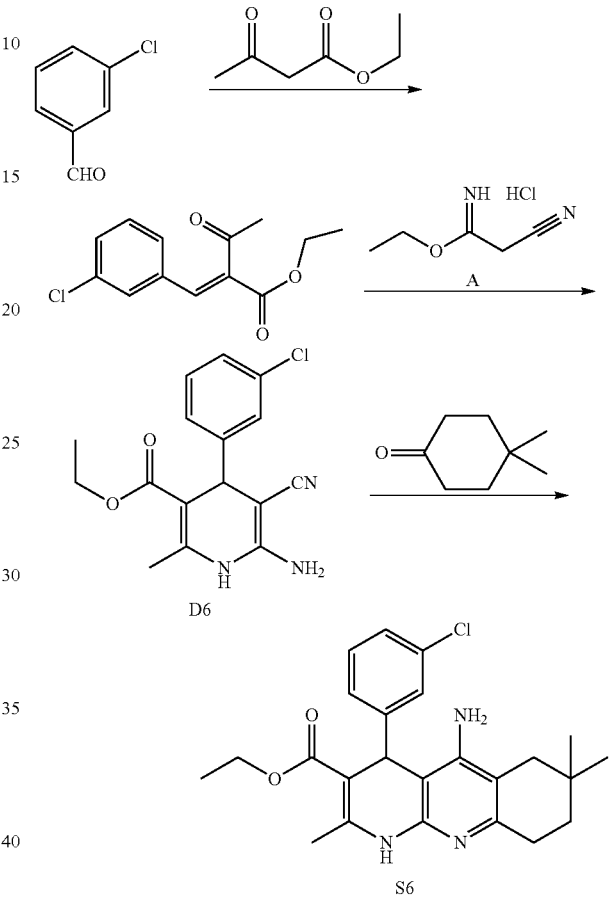

Step 1

By reference to the synthesis method of D1 in Example 1, using the route in Example 1, a two-step reaction was carried out by using ethyl acetoacetate (0.03 mol), 3-chlorobenzaldehyde (0.03 mol) and ammonium acetate (0.075 mol) and raw material A (0.025 mol) to give 2.85 g yellow solid intermediate D6, with an overall yield of 30%, ESI-MS: 316.1 [M−H]

Step 2

By reference to the synthesis of S3 in Example 3, a microwave-assisted reaction was carried out by using intermediate D6 (150 mg, 0.47 mmol), 4,4-dimethyl cyclohexanone (300 mg, 2.36 mmol) and aluminium trichloride (125 mg, 0.94 mmol) to give 73.3 mg yellow solid compound S6, with a yield of 40%.

ESI-MS: 391.2 [M+H]$^+$;

$^1$H NMR (400 MHz, CDCl$_3$): δ7.34 (1H, t, J=1.6), 7.25 (1H, dt, J=1.6, 7.2), 7.18 (1H, m), 7.15 (1H, m), 6.70 (1H, s), 5.01 (1H, s), 4.51 (2H, m), 4.02 (2H, s), 2.73 (2H, m), 2.39 (3H, s), 2.07 (2H, m), 1.61 (2H, m), 1.01 (3H, s), 1.03 (3H, s), 1.30 (3H, m).

EXAMPLE 7

Synthesis of Compound S7

Synthetic Route:

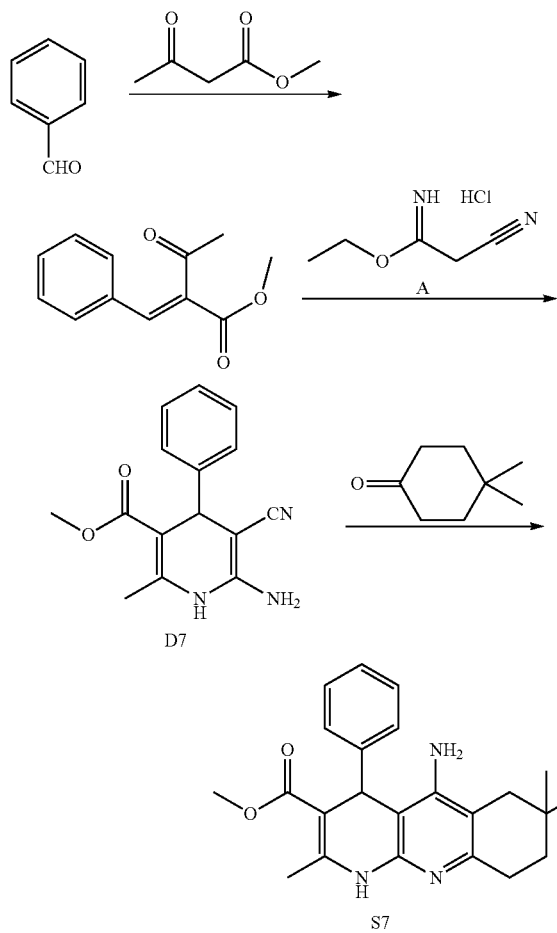

Step 1

By reference to the synthesis method of D1 in Example 1, using the route in Example 1, a two-step reaction was carried out by using methyl acetoacetate (0.03 mol), benzaldehyde (0.03 mol), ammonium acetate (0.069 mol) and raw material A (0.023 mol) to give 3.06 g yellow solid intermediate D7, with an overall yield of 38%, ESI-MS: 268.1 [M−H]⁻.

Step 2

By reference to the synthesis of S1 in Example 1, intermediate D7 (150 mg, 0.56 mmol), 4,4-dimethyl cyclohexanone (427 mg, 3.36 mmol) and aluminium trichloride (136 mg, 1.02 mmol) were reacted to give 95.0 mg yellow solid compound S7, with a yield of 45%.

ESI-MS: 378.2 $[M+H]^+$;

$^1$H NMR (400 MHz, CDCl$_3$): δ9.67 (1H, s), 7.25-7.34 (5H, m), 5.00 (1H, s), 4.73 (2H, s), 3.69 (3H,$), 2.85-2.92 (2H, m), 2.46 (3H, s), 2.09 (1H, d, J=15.6 Hz), 1.99 (1H, d, J=15.6 Hz), 1.59-1.64 (2H, m), 1.03 (6H, s).

EXAMPLE 8

Synthesis of Compound S8

Synthetic Route:

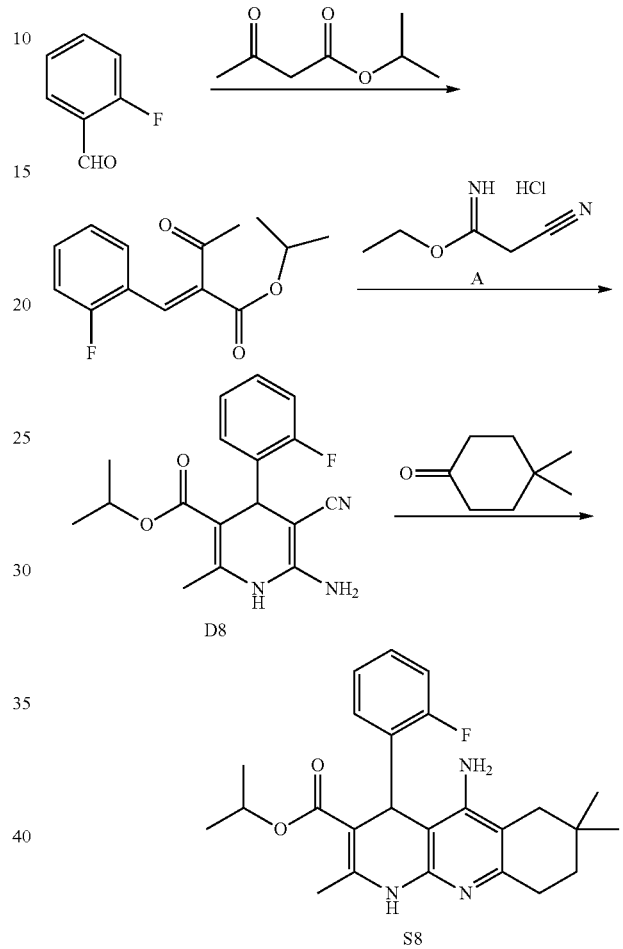

Step 1

By reference to the synthesis of intermediate D4 in Example 4, using the route in Example 1, a two-step reaction was carried out by using isopropyl acetoacetate (0.03 mol), 2-fluorobenzaldehyde (0.03 mol), ammonium acetate (0.06 mol) and raw material A (0.02 mol) to give 3.40 g yellow solid intermediate D8, with an overall yield of 36%, ESI-MS: 316.3 $[M+H]^+$; ESI-MS: 313.9 [M−H]

Step 2

By reference to the synthesis of S1 in Example 1, intermediate D8 (150 mg, 0.48 mmol), 4,4-dimethyl cyclohexanone (363 mg, 2.86 mmol) and aluminium trichloride (127 mg, 0.96 mmol) were reacted to give 178 mg yellow solid compound S8, with a yield of 88%.

ESI-MS: 424.3 $[M+H]^+$;

$^1$H NMR (400 MHz, DMSO-d6): δ9.27 (1H, s), 7.01-7.36 (4H, m), 5.16 (1H, s), 5.04 (2H, s), 4.74-4.77 (1H, m), 2.50-2.52 (2H, m), 2.33 (3H, s), 1.98-2.18 (2H, m), 1.48-1.51 (2H, m), 1.18 (3H, m), 0.94 (9H, m).

EXAMPLE 9

Synthesis of Compound S9

Synthetic Route:

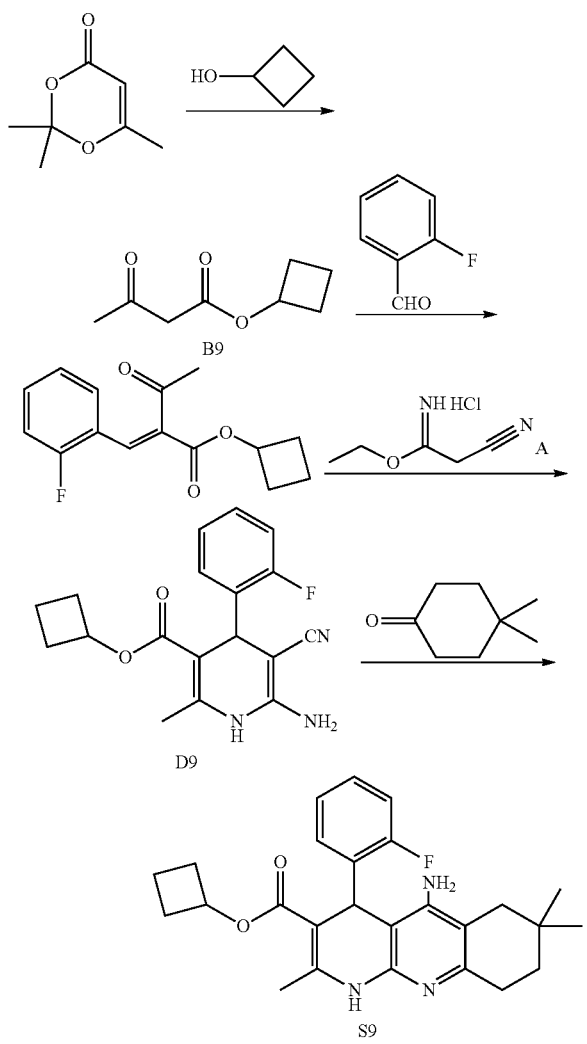

Step 1 Synthesis of Intermediate B9

2,2,6-trimethyl-1,3-dioxin-4-one (1.97 g, 13.9 mmol) and cyclobutanol (1 g, 13.9 mmol) were dissolved in dimethylbenzene (30 mL), heated to 125° C. and stirred over night. After the reaction was completed, the resultant product was concentrated under vacuum. The crude product was separated by chromatography using silica gel column (petroleum ether: ethyl acetate=40:1) to give 1.5 g colorless liquid product B9, with a yield of 69%.

Step 2

By reference to the synthesis of intermediate D4 in Example 4, using the route in Example 1, a two-step reaction was carried out by using cyclobutyl acetoacetate (0.03 mol), 2-fluorobenzaldehyde (0.03 mol), ammonium acetate (0.06 mol) and raw material A (0.02 mol) to give 3.40 g yellow solid intermediate D9, with an overall yield of 36%, ESI-MS: 328.2 [M+H]+; ESI-MS: 325.9 [M−H]−.

Step 3

By reference to the synthesis of S1 in Example 1, intermediate D9 (150 mg, 0.46 mmol), 4,4-dimethyl cyclohexanone (116 mg, 0.92 mmol) and aluminium trichloride (122 mg, 0.92 mmol) were reacted to give 168 mg yellow solid compound S9, with a yield of 88%.

ESI-MS: 434.3 [M+H]+;
$^1$H NMR (400 MHz, DMSO-d6): δ9.32 (1H, s), 7.01-7.37 (4H, m), 5.19 (1H, s), 5.07 (2H, s), 4.79-4.83 (1H, m), 2.50-2.56 (2H, m), 2.32 (3H, s), 2.00-2.28 (4H, m), 1.62-1.72 (2H, m), 1.44-1.55 (4H, m), 0.94 (6H, m).

EXAMPLE 10

Synthesis of Compound S10

Synthetic Route:

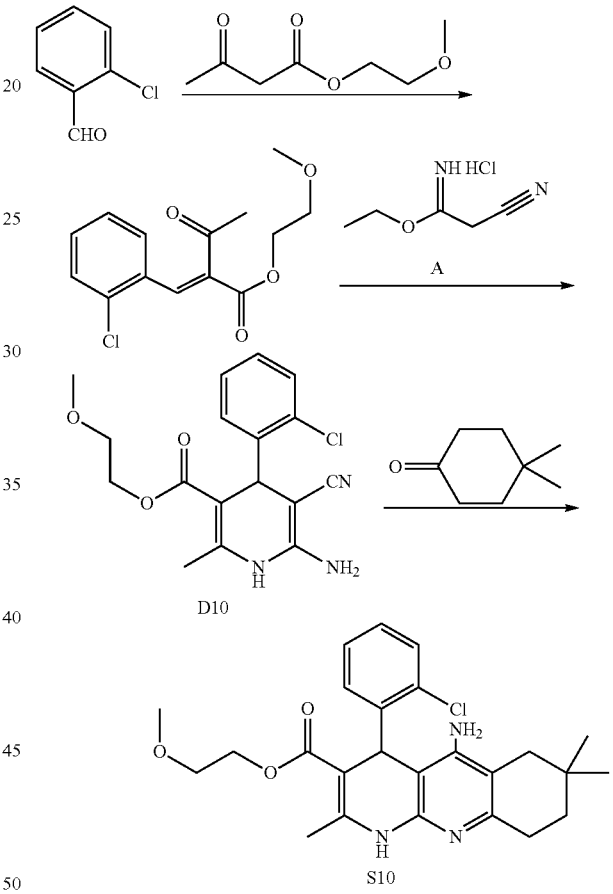

Step 1

By reference to the synthesis of intermediate D4 in Example 4, using the route in Example 1, a two-step reaction was carried out by using methoxyl ethyl acetoacetate (0.03 mol), 2-chlorobenzaldehyde (0.03 mol), ammonium acetate (0.078 mol) and raw material A (0.026 mol) to give 5.51 g yellow solid intermediate D10, with an overall yield of 53%, ESI-MS: 346.1 [M−H]−.

Step 2

By reference to the synthesis of S1 in Example 1, intermediate D10 (150 mg, 0.43 mmol), 4,4-dimethyl cyclohexanone (164 mg, 1.29 mmol) and aluminium trichloride (114 mg, 0.86 mmol) were reacted to give 147 mg yellow solid compound S10, with a yield of 75%.

ESI-MS: 456.3 [M+H]+;

¹H NMR (400 MHz, CDCl₃): δ7.07-7.51 (4H, m), 6.92 (1H, s), 5.45 (1H, s), 4.52 (2H, s), 4.17-4.23 (2H, m), 3.56-3.61 (2H, m), 3.33 (3H, s), 2.61-2.78 (2H, m), 2.44 (3H, s), 1.92-2.18 (2H, m), 1.50-1.51 (2H, m), 0.99 (6H, m).

EXAMPLE 11

Synthesis of Compound S11

Synthetic Route:

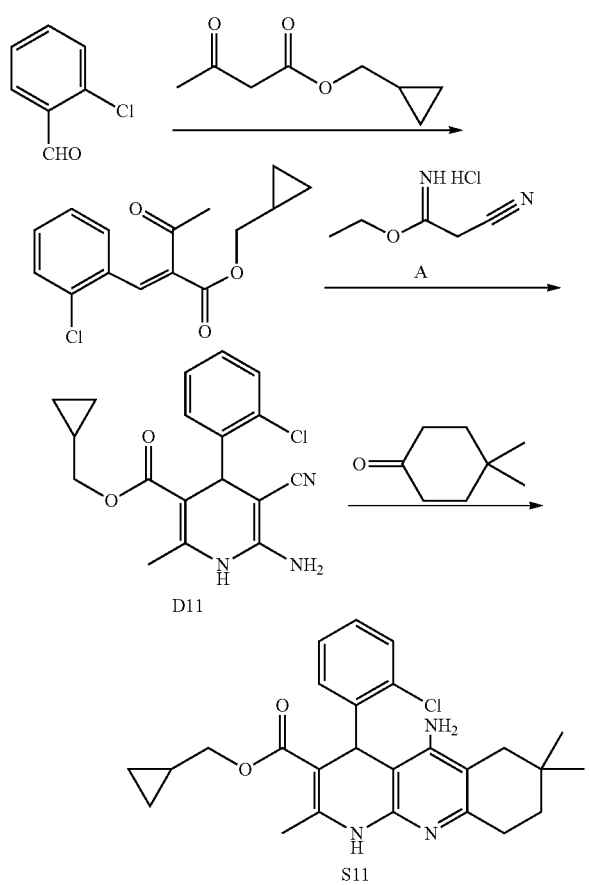

Step 1

By reference to the synthesis of intermediate D4 in Example 4, using the route in Example 1, a two-step reaction was carried out by using cyclopropyl methyl acetoacetate (0.03 mol), 2-chlorobenzaldehyde (0.03 mol), ammonium acetate (0.069 mol) and raw material A (0.023 mol) to give 2.78 g yellow solid intermediate D11, with an overall yield of 27%, ESI-MS: 342.1 [M−H]⁻.

Step 2

By reference to the synthesis of S1 in Example 1, intermediate D11 (150 mg, 0.44 mmol), 4,4-dimethyl cyclohexanone (168 mg, 1.32 mmol) and aluminium trichloride (116 mg, 0.88 mmol) were reacted to give 109 mg yellow solid compound S11, with a yield of 55%.

ESI-MS [M+H]⁺=452.3;

¹H NMR (400 MHz, CDCl₃): δ10.74 (1H, s), 7.43-7.18 (4H, m), 5.45-5.41 (2H, m), 3.91-3.86 (1H, m), 2.89-2.87 (1H, m), 2.53 (3H, s), 2.10-1.95 (2H, m), 1.62-1.60 (8H, m), 1.03 (6H, m), 0.52-0.49 (1H, m).

EXAMPLE 12

Synthesis of Compound S12

Synthetic Route:

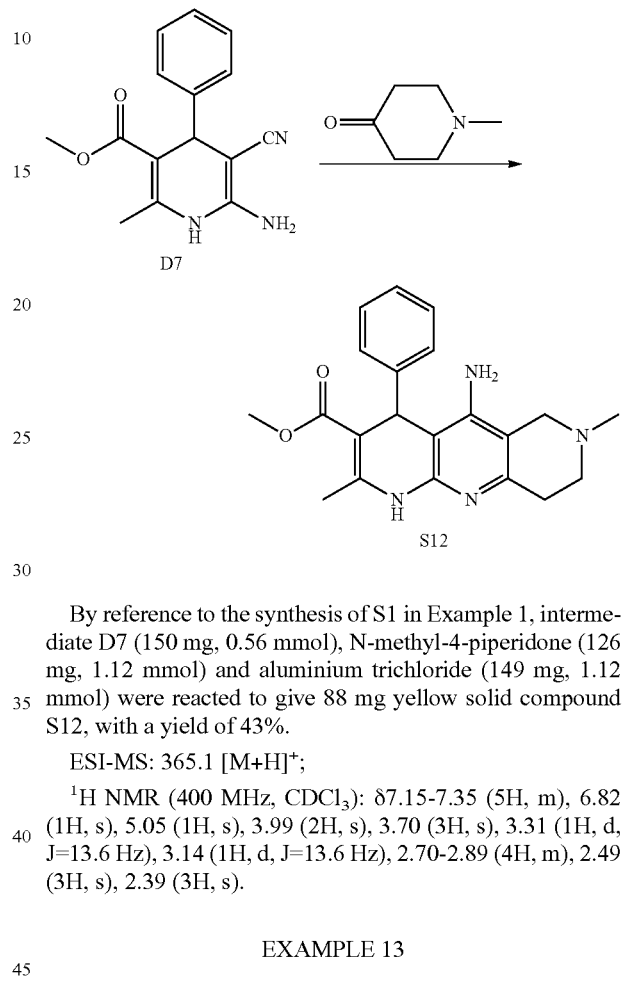

By reference to the synthesis of S1 in Example 1, intermediate D7 (150 mg, 0.56 mmol), N-methyl-4-piperidone (126 mg, 1.12 mmol) and aluminium trichloride (149 mg, 1.12 mmol) were reacted to give 88 mg yellow solid compound S12, with a yield of 43%.

ESI-MS: 365.1 [M+H]⁺;

¹H NMR (400 MHz, CDCl₃): δ7.15-7.35 (5H, m), 6.82 (1H, s), 5.05 (1H, s), 3.99 (2H, s), 3.70 (3H, s), 3.31 (1H, d, J=13.6 Hz), 3.14 (1H, d, J=13.6 Hz), 2.70-2.89 (4H, m), 2.49 (3H, s), 2.39 (3H, s).

EXAMPLE 13

Synthesis of Compound S13

Synthetic Route:

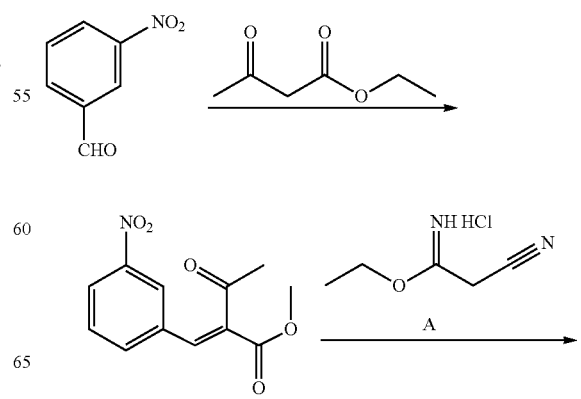

-continued

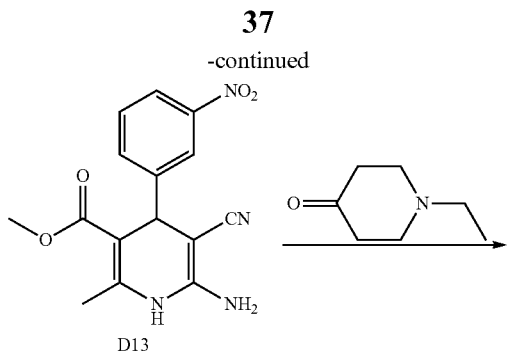

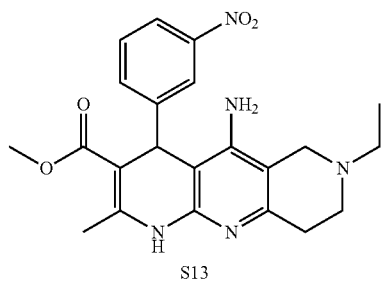

Step 1

By reference to the synthesis of intermediate D1 in Example 1, using the route in Example 1, a two-step reaction was carried out by using methyl acetoacetate (0.03 mol), 3-nitrobenzaldehyde (0.03 mol), ammonium acetate (0.045 mol) and raw material A (0.015 mol) to give 1.03 g yellow solid intermediate D13, with an overall yield of 11%, ESI-MS: 313.1 [M−H]⁻.

Step 2

By reference to the synthesis of S1 in Example 1, intermediate D13 (150 mg, 0.48 mmol), N-ethyl-4-piperidone (122 mg, 0.96 mmol) and aluminium trichloride (127 mg, 0.96 mmol) were reacted to give 52.7 mg yellow solid compound S13, with a yield of 26%.

ESI-MS: 424.1 [M+H]⁺;

$^1$H NMR (400 MHz, CDCl$_3$): δ8.19 (1H, t, J=1.6), 8.04 (1H, dt, J=1.6, 8.0), 7.64 (1H, t, J=8.0), 7.41 (1H, d, J=8.0), 5.16 (1H, s), 4.13 (2H, s), 3.69 (3H, s), 3.15 (2H, m), 2.85 (2H, m), 2.72 (2H, m), 2.39 (3H, s), 1.26 (2H, m), 1.17 (3H, m).

EXAMPLE 14

Synthesis of Compound S14

Synthetic Route:

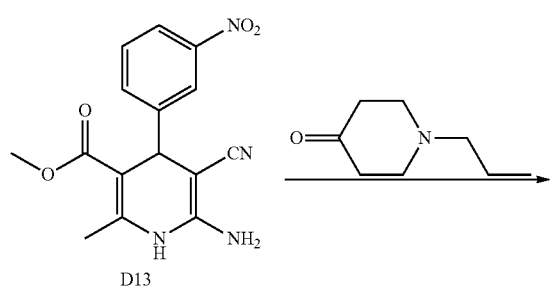

-continued

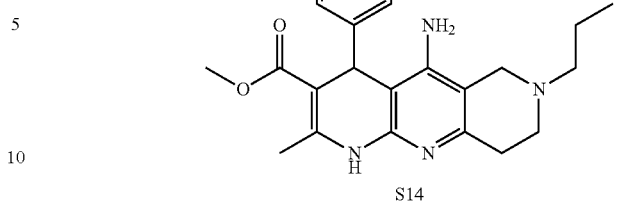

By reference to the synthesis of S1 in Example 1, intermediate D13 (150 mg, 0.48 mmol), N-propyl-4-piperidone (135 mg, 0.96 mmol) and aluminium trichloride (127 mg, 0.96 mmol) were reacted to give 21 mg yellow solid compound 514, with a yield of 10%.

ESI-MS: 438.2 [M+H]⁺;

$^1$H NMR (400 MHz, CDCl$_3$): δ8.19 (1H, t, J=1.6), 8.04 (1H, dt, J=1.6, 8.0), 7.64 (1H, t, J=8.0), 7.41 (1H, d, J=8.0), 5.16 (1H, s), 4.13 (2H, s), 3.69 (3H, s), 3.30 (2H, m), 2.78 (4H, m), 2.53 (2H, m), 2.36 (3H, s), 1.61 (2H, m), 0.92 (3H, m).

EXAMPLE 15

Synthesis of Compound S15

Synthetic Route:

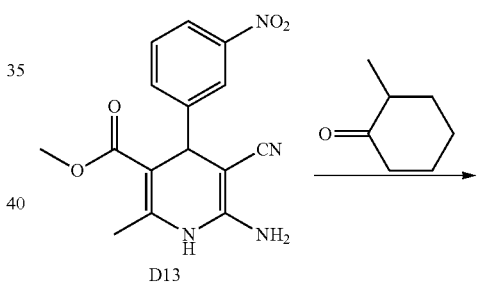

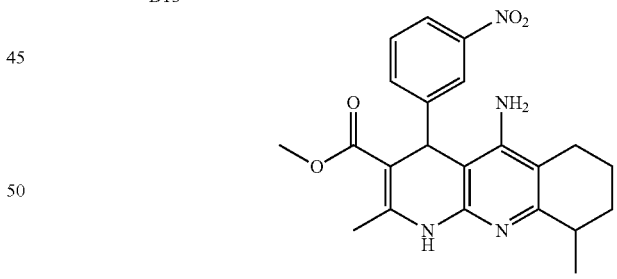

By reference to the synthesis of S1 in Example 1, intermediate D13 (150 mg, 0.48 mmol), 2-methyl cyclohexanone (107 mg, 0.96 mmol) and aluminium trichloride (127 mg, 0.96 mmol) were reacted to give 41 mg yellow solid compound S15, with a yield of 21%.

ESI-MS: 409.2 [M+H]⁺;

$^1$H NMR (400 MHz, CDCl$_3$): δ8.20 (1H, t, J=2.0), 8.04 (1H, dt, J=1.2, 7.4), 7.68 (1H, d, J=8.0), 7.42 (1H, t, J=8.0), 7.13 (1H, s), 5.15 (1H, s), 4.09 (2H, s), 3.68 (3H, s), 2.79 (1H, m), 2.41 (3H, s), 2.33 (1H, m), 2.25 (1H, m), 1.92 (2H, m), 1.76 (1H, m), 1.58 (1H, m), 0.89 (3H, s).

Example 16

Synthesis of Compound S16

Synthetic Route:

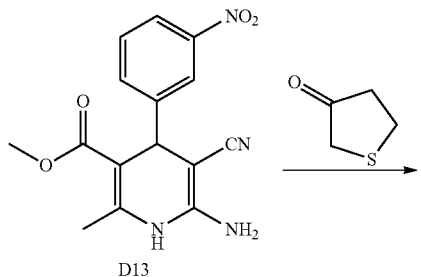

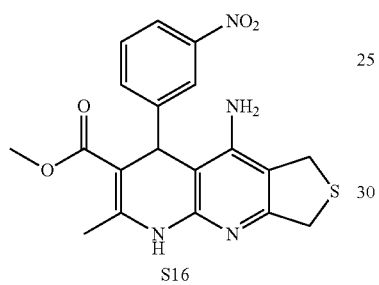

By reference to the synthesis of S1 in Example 1, intermediate D13 (150 mg, 0.48 mmol), tetrahydrothiophen-3-one (98 mg, 0.96 mmol) and aluminium trichloride (127 mg, 0.96 mmol) were reacted to give 23 mg yellow solid compound 516, with a yield of 12%.

ESI-MS: 399.1 [M+H]+;

$^1$H NMR (400 MHz, CDCl$_3$): δ8.18 (1H, d, J=1.4), 8.06 (1H, dd, J=1.4, 8.0), 7.67 (1H, d, J=8.0), 7.44 (1H, t, J=8.0), 7.10 (1H, s), 5.18 (1H, s), 4.04 (2H, s), 3.70 (3H, s), 3.41 (2H, m), 3.27 (2H, m), 2.42 (3H, s).

EXAMPLE 17

Synthesis of Compound S17

Synthetic Route:

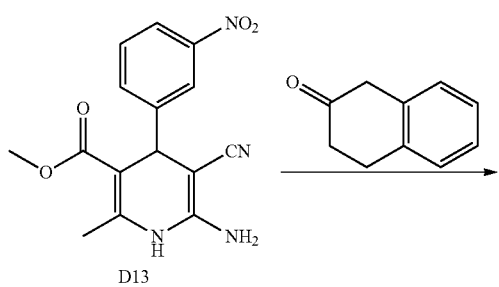

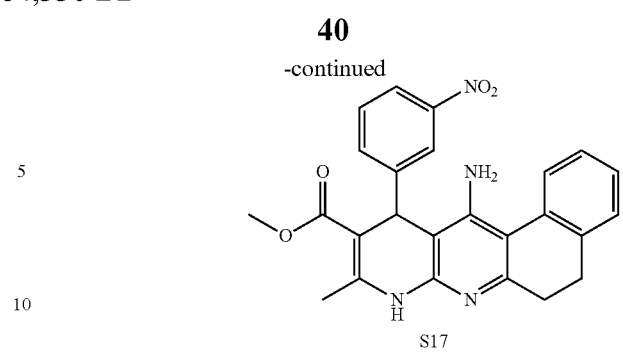

By reference to the synthesis of S1 in Example 1, intermediate D13 (150 mg, 0.48 mmol), 2-tetralone (140 mg, 0.96 mmol) and aluminium trichloride (127 mg, 0.96 mmol) were reacted to give 46.7 mg yellow solid compound S17, with a yield of 22%.

ESI-MS: 443.1 [M+H]+;

$^1$H NMR (400 MHz, CDCl$_3$): δ8.29 (1H, t, J=1.0), 8.00 (1H, dt, J=1.0, 8.0), 7.78 (1H, d, J=8.0), 7.69 (1H, d, J=8.0), 7.54 (1H, t, J=8.0), 7.27 (1H, d, J=6.8), 7.21 (1H, t, J=7.6), 7.11 (1H, d, J=7.6), 5.86 (2H, s), 5.42 (1H, s), 3.58 (3H, s), 2.72 (2H, m), 2.62 (2H, m), 2.35 (3H, s).

EXAMPLE 18

Synthesis of Compound S18

Synthetic Route:

By reference to the synthesis of S1 in Example 1, intermediate D13 (150 mg, 0.48 mmol), 3-methyl-2-cyclohexenone (106 mg, 0.96 mmol) and aluminium trichloride (127 mg, 0.96 mmol) were reacted to give 76.0 mg yellow solid compound 518, with a yield of 39%.

ESI-MS: 407.2 [M+H]+;

$^1$H NMR (400 MHz, CDCl$_3$): δ8.22 (1H, s), 8.04 (1H, d, J=7.6), 7.68 (1H, d, J=7.2), 7.42 (1H, t, J=7.6), 7.25 (1H, s), 6.15 (1H, s), 5.18 (1H, s), 4.05 (2H, s), 3.70 (3H, s), 2.56 (2H, m), 2.39 (3H, s), 2.32 (2H, m), 1.94 (3H, s).

EXAMPLE 19

Synthesis of Compound S19

Synthetic Route:

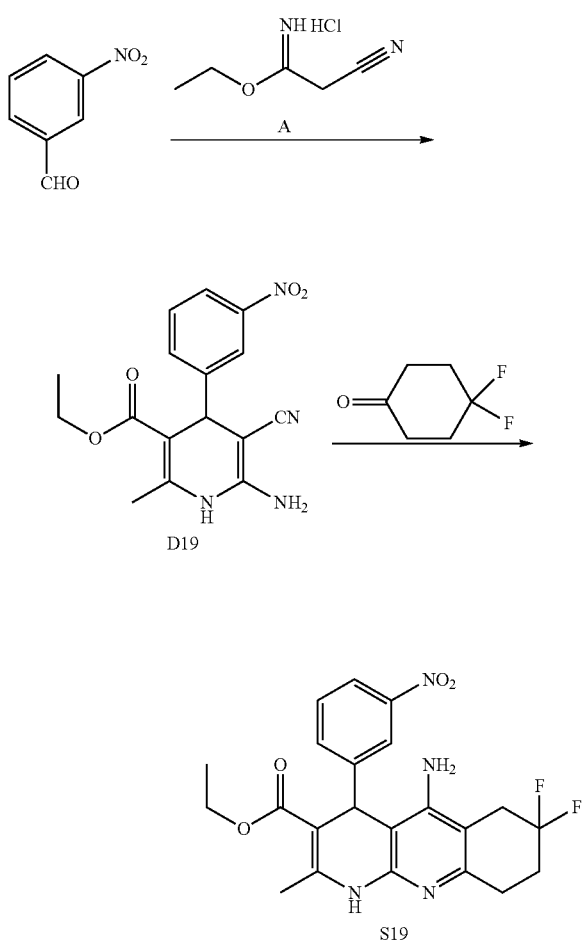

Step 1

By reference to the synthesis of intermediate D2 in Example 2, using the route in Example 2, benzaldehyde (0.03 mol), raw material A (0.03 mol), methyl acetoacetate (0.039 mol) and ammonium acetate (0.039 mol) were reacted to give 2.75 g yellow solid intermediate D19, with an overall yield of 28%, ESI-MS: 327.2 [M−H]⁻.

Step 2

By reference to the synthesis of S1 in Example 1, intermediate D19 (150 mg, 0.46 mmol), 4,4-difluorocyclohexanone (123 mg, 0.92 mmol) and aluminium trichloride (149 mg, 0.92 mmol) were reacted to give 127 mg yellow solid compound S19, with a yield of 62%.

ESI-MS: 445.2 [M+H]⁺;

$^1$H NMR (400 MHz, CDCl$_3$): δ8.21 (1H, t, J=2.0), 8.08 (1H, dt, J=2.0, 8.0), 7.67 (1H, dt, J=1.2, 8.0), 7.44 (1H, t, J=8.0), 5.16 (1H, s), 4.15 (2H, m), 4.07 (2H, s), 2.97 (2H, m), 2.78 (2H, m), 2.43 (3H, s), 2.27 (2H, m), 1.31 (3H, m).

EXAMPLE 20

Synthesis of Compound S20

Synthetic Route:

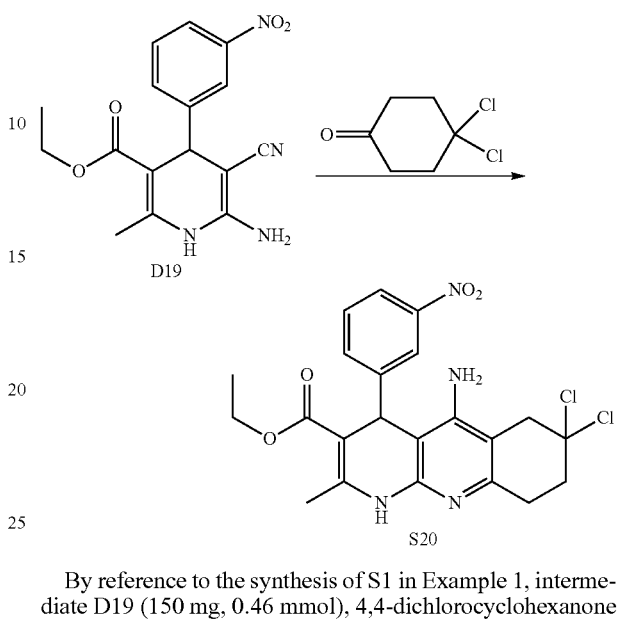

By reference to the synthesis of S1 in Example 1, intermediate D19 (150 mg, 0.46 mmol), 4,4-dichlorocyclohexanone (153 mg, 0.92 mmol) and aluminium trichloride (149 mg, 0.92 mmol) were reacted to give 114 mg yellow solid compound S20, with a yield of 52%.

ESI-MS: 477.2 [M+H]⁺;

$^1$H NMR (400 MHz, CDCl$_3$): δ8.21 (1H, t, J=2.0), 8.04 (1H, dt, J=1.2, 8.0), 7.67 (1H, dt, J=1.2, 8.0), 7.42 (1H, t, J=8.0), 7.08 (1H, s), 5.16 (1H, s), 4.13 (2H, m), 4.08 (2H, s), 3.30 (2H, m), 3.00 (2H, m), 2.63 (2H, m), 2.39 (3H, s), 1.28 (3H, m).

EXAMPLE 21

Synthesis of Compound S21

Synthetic Route:

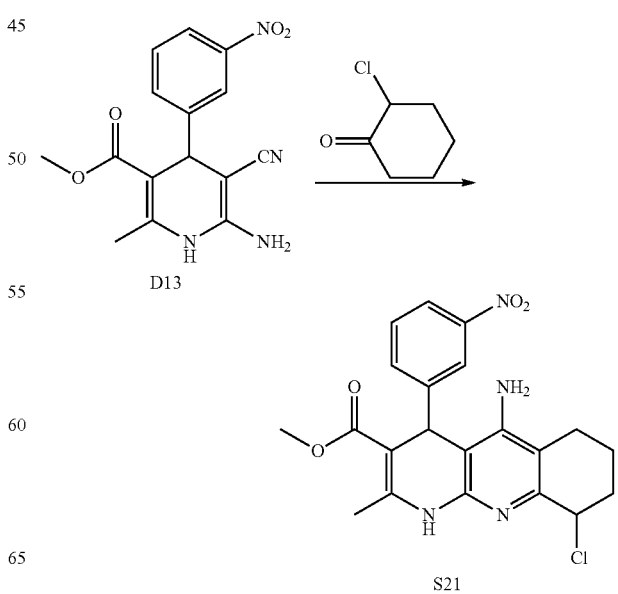

By reference to the synthesis of S1 in Example 1, intermediate D13 (150 mg, 0.48 mmol), 2-chlorocyclohexanone (127 mg, 0.96 mmol) and aluminium trichloride (127 mg, 0.96 mmol) were reacted to give 81.6 mg yellow solid compound S21, with a yield of 39%.

ESI-MS: 429.1 [M+H]$^+$;

$^1$H NMR (400 MHz, CDCl$_3$): δ8.22 (1H, t, J=1.6), 8.03 (1H, d, J=8.0), 7.68 (1H, d, J=8.0), 7.43 (1H, t, J=8.0), 5.15 (1H, s), 4.31 (2H, s), 3.67 (3H, s), 3.30 (2H, m), 3.01 (2H, m), 1.74 (2H, m), 2.42 (3H, s), 1.46 (2H, m).

EXAMPLE 22

Synthesis of Compound S22

Synthetic Route:

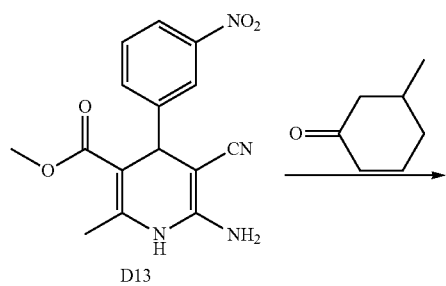

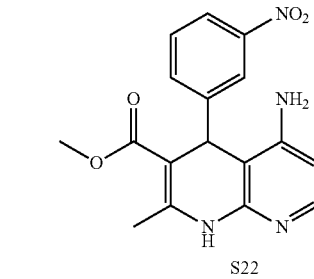

By reference to the synthesis of S1 in Example 1, intermediate D13 (150 mg, 0.48 mmol), 3-methylcyclohexanone (107 mg, 0.96 mmol) and aluminium trichloride (127 mg, 0.96 mmol) were reacted to give 152.7 mg yellow solid compound S22, with a yield of 78%.

ESI-MS: 409.2 [M+H]$^+$;

$^1$H NMR (400 MHz, CDCl$_3$): δ8.20 (1H, d, J=1.6), 8.05 (1H, dt, J=1.6, 8.0), 7.67 (1H, dd, J=1.6, J=8.0), 7.43 (1H, t, J=8.0), 5.15 (1H, s), 4.18 (2H, s), 3.70 (3H, s), 2.74 (1H, m), 2.42 (3H, s), 2.38 (4H, m), 1.37 (2H, m), 1.09 (3H, s).

EXAMPLE 23

Synthesis of Compound S23

Synthetic Route:

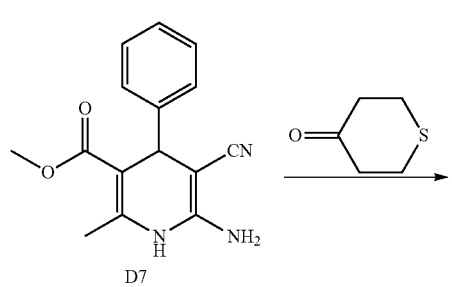

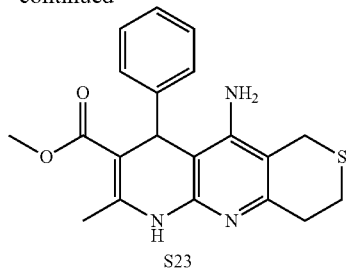

By reference to the synthesis of S1 in Example 1, intermediate D7 (150 mg, 0.56 mmol), tetrahydrothiapyran-4-one (130 mg, 1.12 mmol) and aluminium trichloride (149 mg, 1.12 mmol) were reacted to give 108.9 mg yellow solid compound S23, with a yield of 53%.

ESI-MS: 368.2 [M+H]$^+$;

$^1$H NMR (400 MHz, CDCl$_3$): 7.17-7.36 (5H, m), 6.88 (1H, s), 5.03 (1H, s), 4.15 (2H, s), 3.69 (3H, s), 3.45 (1H, d, J=15.2 Hz), 3.36 (1H, d, J=15.2 Hz), 3.04 (2H, t, J=6.0 Hz), 2.89 (2H, t, J=6.0 Hz), 2.40 (3H, s).

EXAMPLE 24

Synthesis of Compound S24

Synthetic Route:

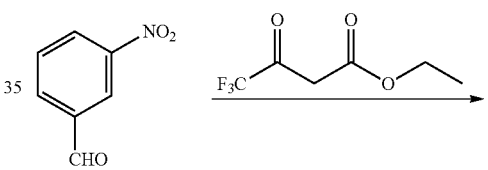

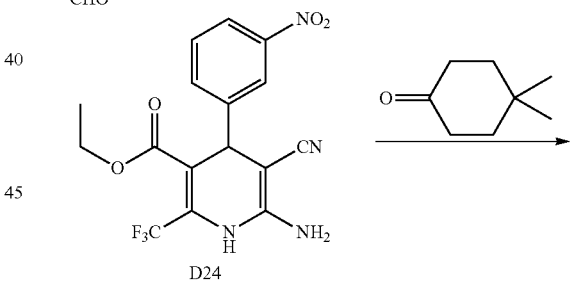

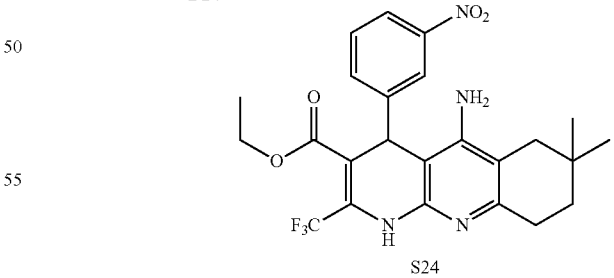

Step 1

By reference to the synthesis method of D2 in Example 2, using the route in Example 2,3-nitrobenzaldehyde (1.51 g, 0.01 mol), ethyl trifluoroacetoacetate (2.4 g, 0.013 mol), intermediate A (1.5 g, 0.01 mol) and ammonium acetate (0.92 g, 0.012 mol) were reacted to give 760 mg yellow solid target intermediate D24, with a yield of 20%.

Step 2

Intermediate D24 (120 mg, 0.314 mmol) was placed into a microwave reaction tube, and dissolved in 3 mL 1,2-dichloroethane, to which 4,4-dimethyl cyclohexanone (237 mg, 1.88 mmol) and aluminium trichloride (84 mg, 0.628 mmol) were added. The mixture was reacted in a microwave reaction device with temperature T=120° C. for time t=1 h. After confirming the raw material had been completely comsumed by TLC, the reaction was stopped, and allowed for cooling to room temperature. Subsequently, the reaction mixture was poured into a solution of THF: $H_2O$=1:1 (10 mL), and 10% aqueous NaOH solution was added dropwise while stirring until pH>7. The mixture was extracted by dichloromethane (10 mL×3). The organic phase was combined and washed with saturated saline solution. Subsequently, it was dried by anhydrous sodium sulfate, and concentrated. The resultant product was separated by chromatography using silica gel column (petroleum ether:ethyl acetate=3:1) to give 60 mg yellow oil product S24, with a yield of 40%.

ESI-MS: 491.2 $[M+H]^+$;

$^1$H NMR (400 MHz, DMSO-d6): δ8.32 (1H, s), 8.02 (1H, d, J=8.0 Hz), 7.68 (1H, d, J=7.2 Hz), 7.55 (1H, t, J=8.0 Hz), 5.99 (2H, br s), 5.32 (1H, s), 4.04 (2H, q, J=7.0 Hz), 2.62-2.58 (2H, m), 2.18 (1H, d, J=16.4 Hz), 1.97 (1H, d, J=16.0 Hz), 1.51-1.48 (2H, m), 1.18 (3H, t, J=7.2 Hz), 0.95-0.94 (6H, m).

EXAMPLE 25

Synthesis of Compound S25

Synthetic Route:

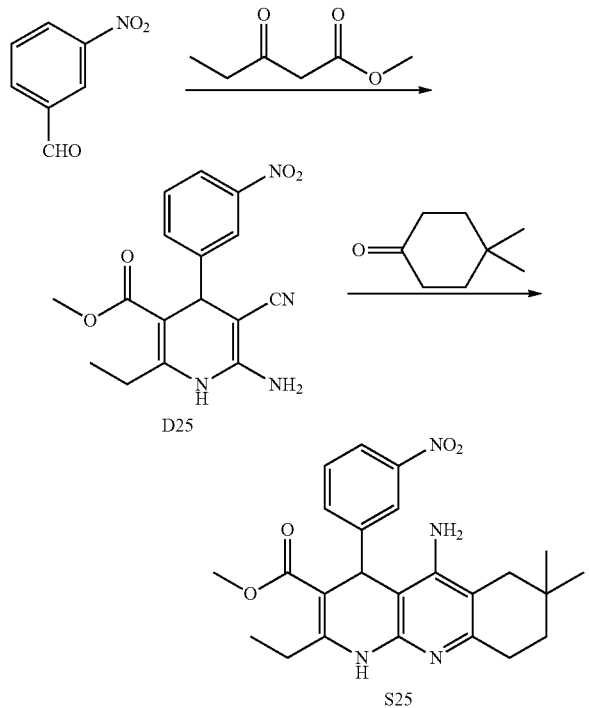

Step 1

By reference to the synthesis method of D2 in Example 2, using the route in Example 2,3-nitrobenzaldehyde (1.51 g, 10 mmol), methyl propionylacetate (1.69 g, 13 mmol), intermediate A (1.5 g, 10 mmol) and ammonium acetate (0.92 g, 12 mmol) were reacted to give 760 mg yellow solid target intermediate D25, with a yield of 23%.

Step 2

By reference to the synthesis method of S3 in Example 3, a microwave-assisted reaction was carried out by using intermediate C8 (120 mg, 0.366 mmol), 4,4-dimethyl cyclohexanone (277 mg, 2.196 mmol) and aluminium trichloride (97 mg, 0.732 mmol) to give 30 mg yellow solid target product S25, with a yield of 19%.

ESI-MS: 437.2 $[M+H]^+$;

$^1$H NMR (400 MHz, DMSO-d6): δ9.37 (1H, s), 8.28 (1H, s), 7.96 (1H, d, J=8.0 Hz), 7.76 (1H, d, J=7.6 Hz), 7.50 (1H, t, J=8.0 Hz), 5.59 (2H, br s), 5.25 (1H, s), 3.54 (3H, s), 2.82-2.70 (2H, m), 2.61-2.55 (2H, m), 2.20-1.95 (2H, m), 1.50-1.47 (2H, m), 1.12 (3H, t, J=7.2 Hz), 0.95-0.94 (6H, m).

EXAMPLE 26

Synthesis of Compound S26

Synthetic Route:

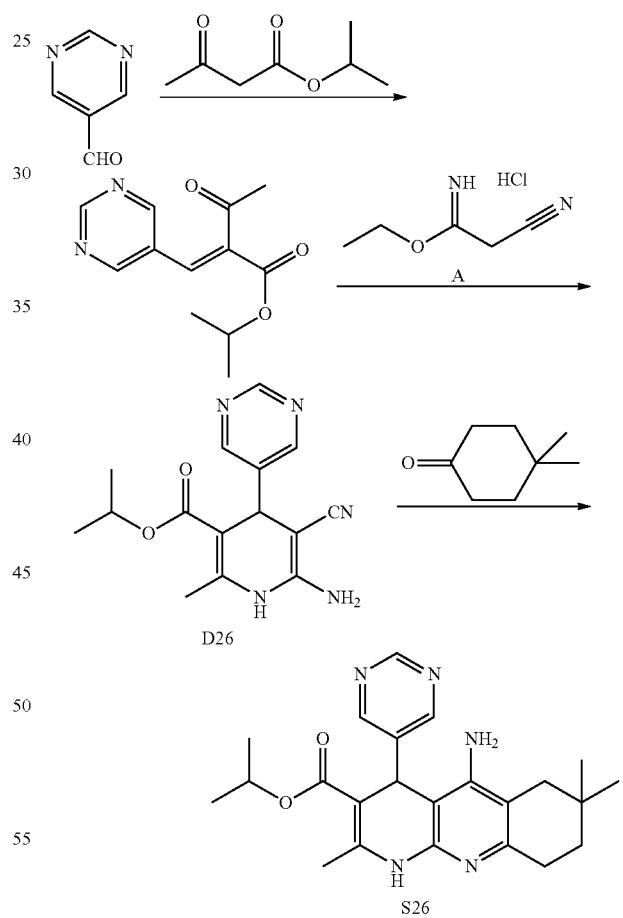

Step 1

By reference to the synthesis of intermediate D1 in Example 1, using the route in Example 1, a two-step reaction was carried out by using isopropyl acetoacetate (0.03 mol), 5-pyrimidine formaldehyde (0.03 mol), ammonium acetate (0.045 mol) and raw material A (0.02 mol) to give 2.87 g yellow solid intermediate D26, with an overall yield of 32%, ESI-MS: 297.9 $[M-H]^-$.

Step 2

By reference to the synthesis of S1 in Example 1, intermediate D26 (125 mg, 0.42 mmol), 4,4-dimethyl cyclohexanone (53 mg, 0.42 mmol) and AlCl$_3$ (84 mg, 0.63 mmol) were reacted to give 34 mg yellow solid compound S26, with a yield of 29.4%.

ESI-MS: 408.3 [M+H]$^+$;

$^1$H NMR (400 MHz, DMSO-d6): δ9.36 (1H, s), 8.91 (1H, s), 8.71 (2H, s), 5.61 (2H, s), 5.06 (1H, s), 4.82 (1H, m), 2.57 (2H, m), 2.32 (3H, s), 1.49 (2H, t, J=6.4 Hz), 1.22 (3H, d, J=6.0 Hz), 1.05 (3H, d, J=6.0 Hz), 0.95 (6H, s), 0.88 (2H, m).

EXAMPLE 27

Synthesis of Compound S27

Synthetic Route:

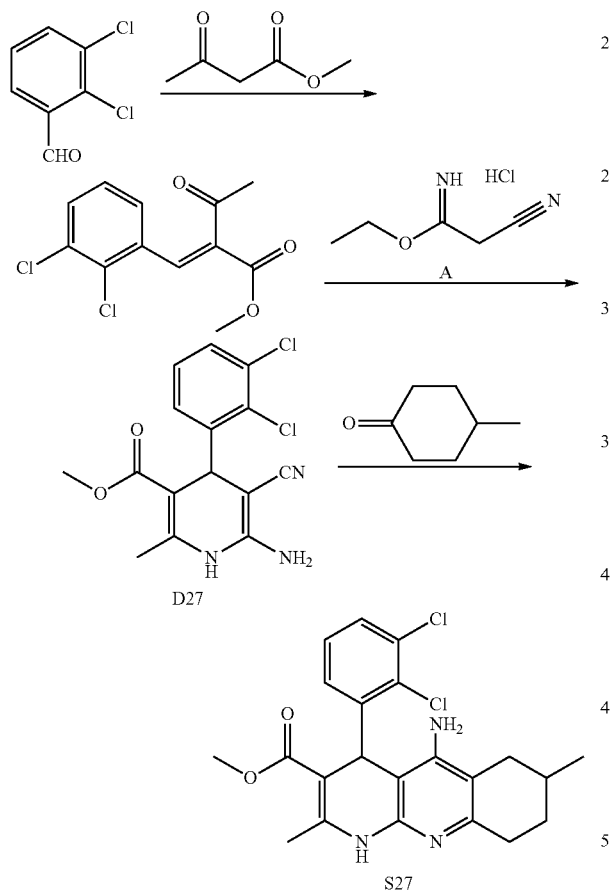

Step 1

By reference to the synthesis of intermediate D1 in Example 1, using the route in Example 1, a two-step reaction was carried out by using methyl acetoacetate (0.03 mol), 2,3-dichlorobenzaldehyde (0.03 mol), ammonium acetate (0.045 mol) and raw material A (0.02 mol) to give 3.04 g yellow solid intermediate D27, with an overall yield of 30%, ESI-MS: 337.9 [M−H]

Step 2

By reference to the synthesis of S1 in Example 1, intermediate D27 (150 mg, 0.44 mmol), 4-methylcyclohexanone (98 mg, 0.88 mmol) and AlCl$_3$ (117 mg, 0.88 mmol) were reacted to give 152 mg yellow solid compound S26, with a yield of 80%.

ESI-MS: 432.0 [M+H]$^+$;

$^1$H NMR (400 MHz, CDCl$_3$): 7.41-7.30 (2H, m), 7.12 (1H, t, J=8.0 Hz), 6.93 (1H, s), 5.48 (1H, s), 4.58 (2H, br s), 3.65 (3H, s), 2.74-2.69 (2H, m), 2.45 (3H, s), 1.82-1.60 (5H, m), 1.11-1.05 (3H, m).

EXAMPLE 28

Synthesis of Compound S28

Synthetic Route:

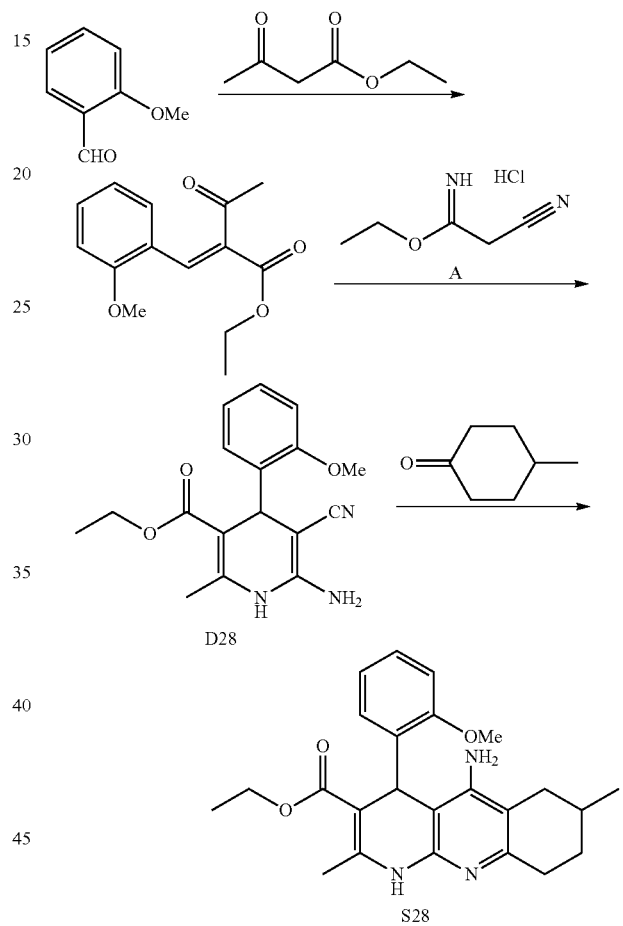

Step 1

By reference to the synthesis of intermediate D1 in Example 1, using the route in Example 1, a two-step reaction was carried out by using ethyl acetoacetate (0.03 mol), 2-methoxybenzaldehyde (0.03 mol), ammonium acetate (0.06 mol) and raw material A (0.02 mol) to give 3.74 g yellow solid intermediate D28, with an overall yield of 39%, ESI-MS: 312.0 [M−H]$^−$.

Step 2

By reference to the synthesis of S1 in Example 1, intermediate D28 (150 mg, 0.48 mmol), 4-methylcyclohexanone (98 mg, 0.88 mmol) and AlCl$_3$ (117 mg, 0.88 mmol) were reacted to give 127 mg yellow solid compound S28, with a yield of 65%.

ESI-MS: 408.2 [M+H]$^+$;

$^1$H NMR (400 MHz, CDCl$_3$): δ7.21 (1H, dd, J=1.6, 8.0), 7.16 (1H, t, J=8.0), 7.10 (1H, d, J=8.0), 6.88 (1H, d, J=8.0), 5.30 (1H, s), 3.88 (3H, s), 3.86 (2H, m), 2.64 (2H, m), 2.36 (3H, s), 1.98 (1H, m), 1.78 (2H, m), 1.32 (2H, m), 1.03 (6H, m).

EXAMPLE 29

Synthesis of Compound S29

Synthetic Route:

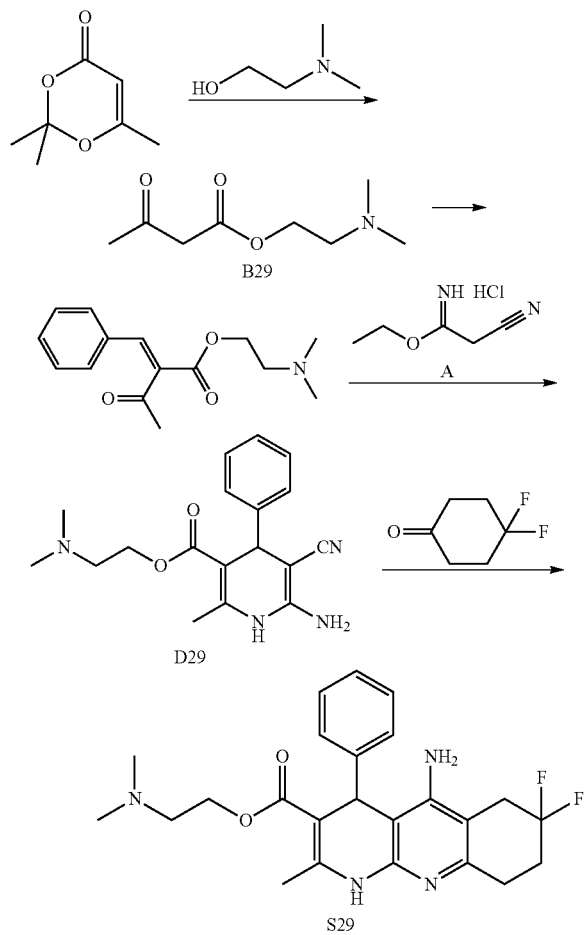

Step 1

2,2,6-trimethyl-1,3-dioxin-4-one (1.97 g, 13.9 mmol) and N,N-dimethyl ethanol (1.23 g, 13.9 mmol) were dissolved in xylene (30 mL), heated to 125° C. and stirred over night. After the reaction was completed, the resultant product was concentrated under vacuum. The crude product was separated by chromatography using silica gel column (petroleum ether: ethyl acetate=40:1) to give 1.99 g colorless liquid product B29, with a yield of 83%.

Step 2

By reference to the synthesis of intermediate D1 in Example 1, a two-step reaction was carried out by using B29 (0.03 mol), benzaldehyde (0.03 mol), ammonium acetate (0.06 mol) and raw material A (0.02 mol) to give 6.3 g yellow solid intermediate D29, with an overall yield of 65%, ESI-MS: 327.2[M+H]$^+$; ESI-MS: 325.2 [M−H]$^-$.

Step 3

By reference to the synthesis of S1 in Example 1, intermediate D29 (150 mg, 0.46 mmol), 4,4-difluorocyclohexanone (98 mg, 0.88 mmol) and AlCl$_3$ (117 mg, 0.88 mmol) were reacted to give 104 mg yellow solid compound S29, with a yield of 51%.

ESI-MS: 443.2 [M+H]$^+$;

$^1$H NMR (400 MHz, CDCl$_3$): 7.16-7.39 (5H, m), 6.93 (1H, s), 5.10 (1H, s), 4.19-4.25 (4H, m), 2.57-2.96 (6H, m), 2.43 (3H, s), 2.31 (6H, s), 2.17-2.33 (2H, m).

EXAMPLE 30

Synthesis of Compound S30

Synthetic Route:

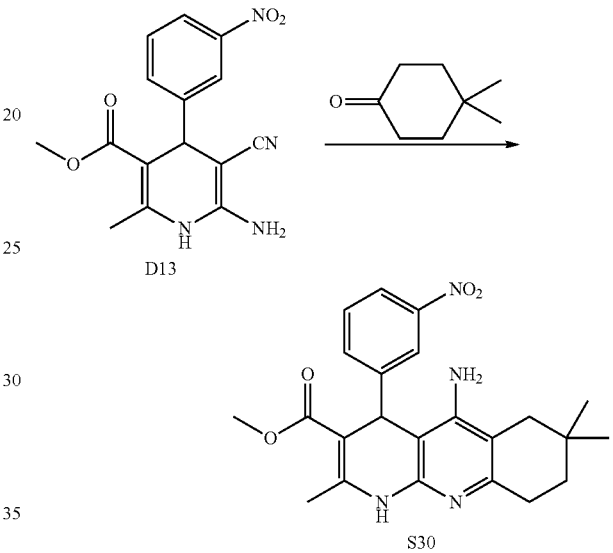

By reference to the synthesis of S1 in Example 1, intermediate D13 (314 mg, 1.0 mmol), 4,4-dimethylcyclohexanone (252 mg, 2.0 mmol) and aluminium trichloride (264 mg, 2.0 mmol) were reacted to give 223.6 mg yellow solid compound S30, with a yield of 53%.

ESI-MS: 423.2 [M+H]$^+$;

$^1$H NMR (400 MHz, CDCl$_3$): δ9.04 (1H, s), 8.20 (1H, s), 8.03 (1H, d, J=7.6), 7.67 (1H, d, J=7.6), 7.42 (1H, t, J=7.6), 5.15 (1H, s), 4.38 (2H, s), 3.68 (3H, s), 2.62-2.75 (2H, m), 2.42 (3H, s), 1.94-2.13 (2H, m), 1.55-1.62 (2H, m), 0.99 (6H, s).

EXAMPLE 31

Synthesis of Compound S31

Synthetic Route:

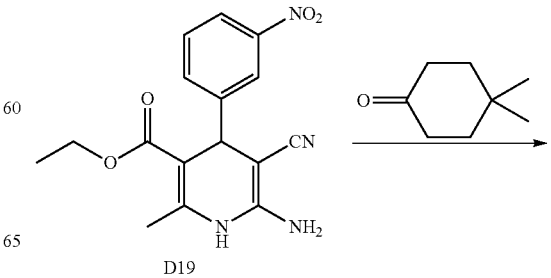

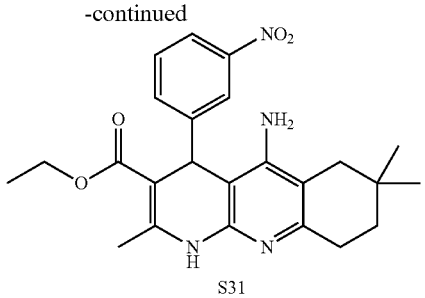

By reference to the synthesis of S1 in Example 1, intermediate D19 (177 mg, 0.54 mmol), 4,4-dimethylcyclohexanone (136.1 mg, 1.08 mmol) and aluminium trichloride (143 mg, 1.08 mmol) were reacted to give 108.3 mg yellow solid compound S31, with a yield of 46%.

ESI-MS: 437.2 [M+H]$^+$;

$^1$H NMR (400 MHz, CDCl$_3$): δ8.23 (1H, m), 8.05 (1H, d, J=7.6), 7.68 (1H, d, J=7.6), 7.43 (1H, t, J=7.6), 6.78 (1H, s), 5.15 (1H, s), 4.15 (2H, m), 4.04 (2H, s), 2.71-2.78 (2H, m), 2.42 (3H, s), 2.01-2.13 (2H, m), 1.59-1.62 (2H, m), 1.31 (1H, t, J=7.1), 1.02 (6H, s).

EXAMPLE 32

Synthesis of Compound S32

Synthetic Route:

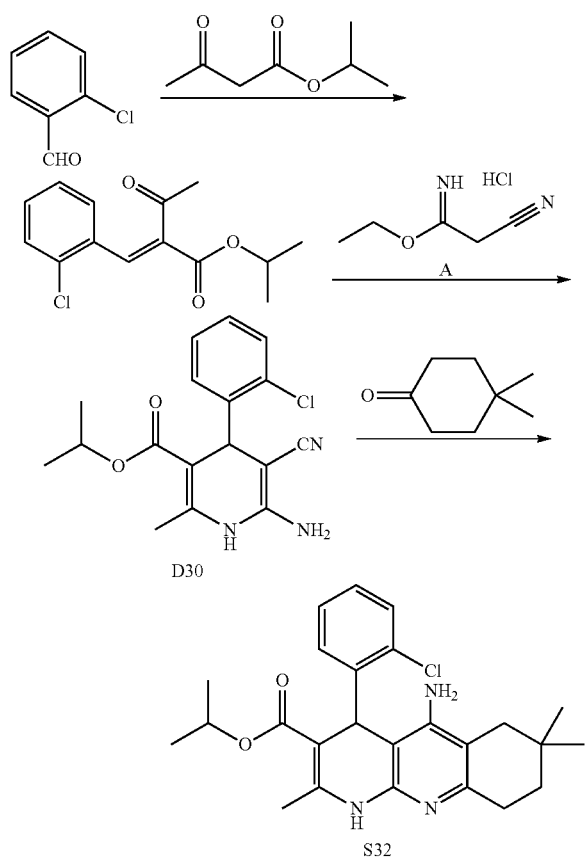

Step 1

By reference to the synthesis of intermediate D4 in Example 4, using the route in Example 1, a two-step reaction was carried out by using isopropyl acetoacetate (0.05 mol), 2-chlorobenzaldehyde (0.05 mol), ammonium acetate (0.10 mol) and raw material A (0.03 mol) to give 3.09 g yellow solid intermediate D30, with an overall yield of 28%, ESI-MS: 332.1 [M+H]$^+$; ESI-MS: 330.9 [M−H]$^−$.

Step 2

By reference to the synthesis of S1 in Example 1, intermediate D30 (331 mg, 1.0 mmol), 4,4-dimethylcyclohexanone (252 mg, 2.0 mmol) and aluminium trichloride (264 mg, 2.0 mmol) were reacted to give 276.6 mg yellow solid compound S32, with a yield of 63%.

ESI-MS: 424.3 [M+H]$^+$;

$^1$H NMR (400 MHz, DMSO-d6): δ9.65 (1H, s), 7.15-7.36 (4H, m), 5.18 (1H, s), 5.01 (2H, s), 4.79-4.84 (1H, m), 2.50-2.52 (2H, m), 2.30 (3H, s), 1.96-2.17 (2H, m), 1.49-1.52 (2H, m), 1.20 (3H, m), 0.94 (9H, m).

EXAMPLE 33

Synthesis of Compound S33

Synthetic Route:

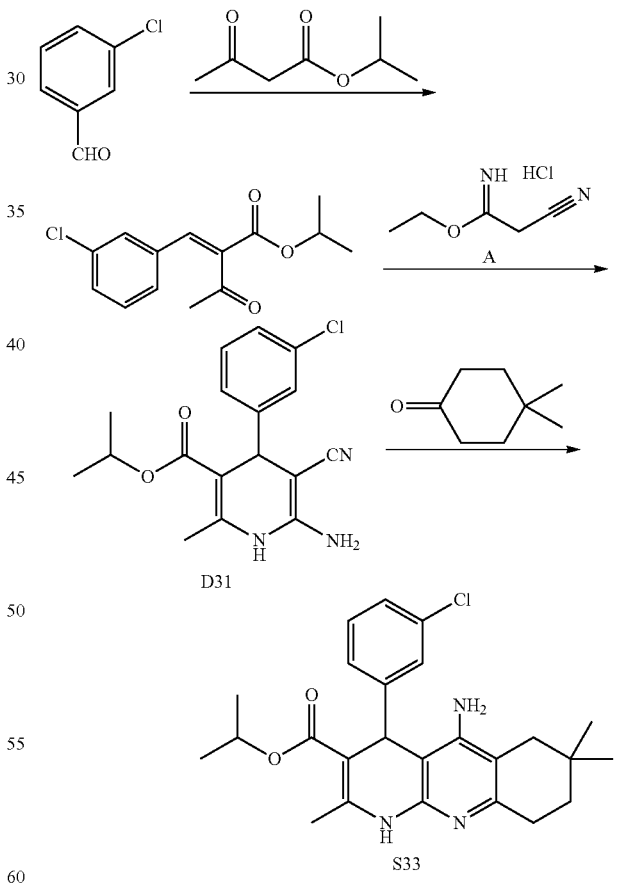

Step 1

By reference to the synthesis of intermediate D4 in Example 4, using the route in Example 1, a two-step reaction was carried out by using isopropyl acetoacetate (0.03 mol), 3-chlorobenzaldehyde (0.03 mol), ammonium acetate (0.06 mol) and raw material A (0.02 mol) to give 2.12 g yellow solid intermediate D30, with an overall yield of 32%. ESI-MS: 332.1 [M+H]⁺; ESI-MS: 330.9 [M−H]⁻.
Step 2
By reference to the synthesis of S1 in Example 1, intermediate D31 (331 mg, 1.0 mmol), 4,4-dimethylcyclohexanone (252 mg, 2.0 mmol) and aluminium trichloride (264 mg, 2.0 mmol) were reacted to give 258.0 mg yellow solid compound S33, with a yield of 61%.

ESI-MS: 424.3 [M+H]⁺;
¹H NMR (400 MHz, DMSO-d6): δ9.74 (1H, s), 7.47 (1H, s), 7.11-7.22 (3H, m), 5.40 (2H, s), 5.01 (1H, s), 4.79-4.84 (1H, m), 2.55-2.58 (2H, m), 2.28 (3H, s), 2.16 (1H, d, 16.4), 1.98 (1H, d, 16.4), 1.46-1.50 (2H, m), 1.22 (3H, d, 6.4), 1.09 (3H, d, 6.0), 0.94 (6H, m).

EXAMPLE 34

Synthesis of Compound S34

Synthetic Route:

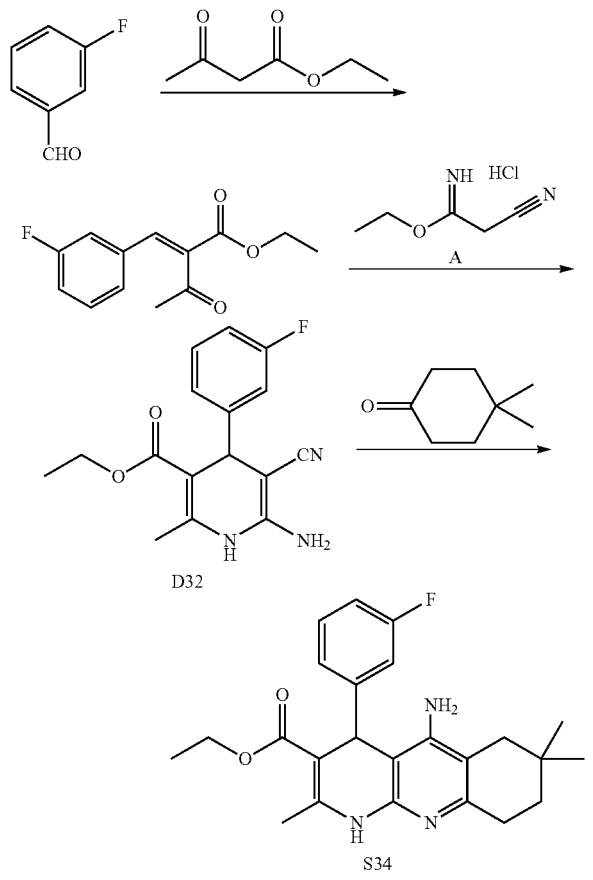

Step 1
By reference to the synthesis of intermediate D4 in Example 4, using the route in Example 1, a two-step reaction was carried out by using ethyl acetoacetate (0.03 mol), 3-fluorobenzaldehyde (0.03 mol), ammonium acetate (0.06 mol) and raw material A (0.02 mol) to give 2.17 g yellow solid intermediate D32, with an overall yield of 36%, ESI-MS: 302.1 [M+H]⁺; ESI-MS: 300.4 [M−H]⁻.
Step 2
By reference to the synthesis of S1 in Example 1, intermediate D32 (150.5 mg, 0.5 mmol), 4,4-dimethylcyclohexanone (126 mg, 1.0 mmol) and aluminium trichloride (132 mg, 1.0 mmol) were reacted to give 147.2 mg yellow solid compound S34, with a yield of 72%.

ESI-MS: 410.3 [M+H]⁺;
¹H NMR (400 MHz, CDCl₃): δ7.22-7.31 (1H, m), 7.14 (1H, d, 6.0), 7.09 (1H, m), 6.88 (1H, m), 5.05 (1H, s), 4.10-4.23 (2H, m), 4.05 (2H, s), 2.68-2.73 (2H, m), 2.40 (3H, s), 2.01-2.15 (2H, m), 1.61 (2H, t, 6.8), 1.28 (3H, t, 7.2), 1.03 (3H, 6, 7.2).

EXAMPLE 35

Synthesis of Compound S35

Synthetic Route:

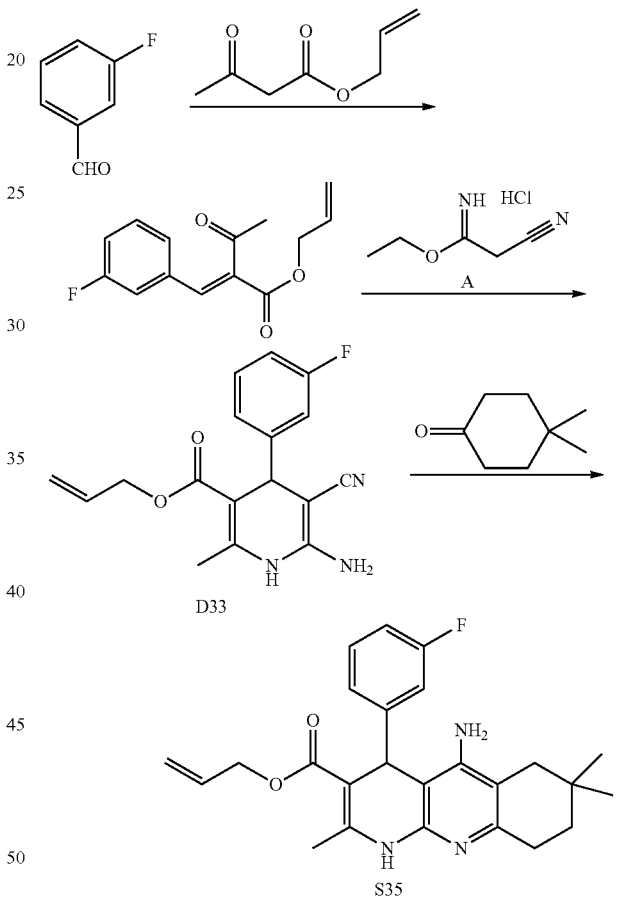

Step 1
By reference to the synthesis of compound D4 in Example 4, using the route in Example 1, a two-step reaction was carried out by using allyl acetoacetate (0.03 mol), 3-fluorobenzaldehyde (0.03 mol), ammonium acetate (0.072 mol) and raw material A (0.026 mol) to give 1.87 g yellow solid intermediate D33, with an overall yield of 23%.
Step 2
By reference to the synthesis of S1 in Example 1, intermediate D33 (313 mg, 1 mmol), 4,4-dimethylcyclohexanone (252 mg, 2.0 mmol) and aluminium trichloride (264 mg, 2.0 mmol) were reacted to give 138.9 mg yellow solid compound S35, with a yield of 33%.

ESI-MS: 422.2 [M+H]⁺; ESI-MS: 420.2 [M−H]⁻;

¹H NMR (400 MHz, CDCl₃): δ7.18-7.29 (1H, m), 7.15 (1H, m), 7.05 (1H, d, J=10.0), 6.95 (1H, s), 6.87 (1H, t, J=8.0), 5.90-6.01 (1H, m), 5.22-5.29 (2H, m), 5.07 (1H, s), 4.61 (2H, m), 4.05 (2H, s), 2.71-2.76 (2H, m), 2.41 (3H, s), 2.01-2.14 (2H, m), 1.61 (2H, t, J=6.4), 1.03 (6H, d, J=6.8).

EXAMPLE 36

Synthesis of Compound S36

Synthetic Route:

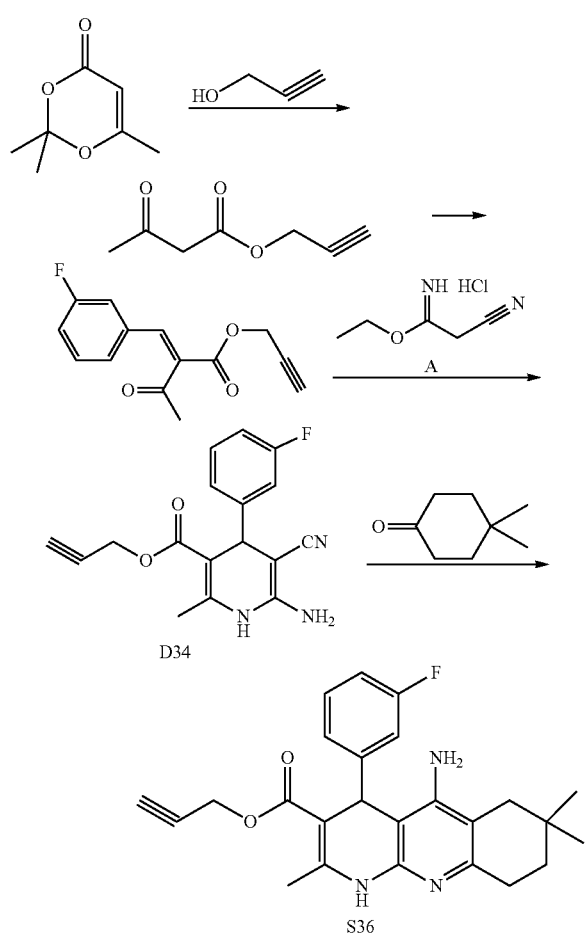

Step 1

By reference to the synthesis of compound D29 in Example 29, using the route in Example 29, a two-step reaction was carried out by using 2,2,6-trimethyl-1,3-dioxin-4-one (0.05 mol), propargyl alcohol (0.05 mol), 3-fluorobenzaldehyde (0.045 mol) and ammonium acetate (0.08 mol) and raw material A (0.035 mol) to give 2.29 g yellow solid intermediate D34, with an overall yield of 21%.

Step 2

By reference to the synthesis of S1 in Example 1, intermediate D34 (311 mg, 1 mmol), 4,4-dimethyl cyclohexanone (252 mg, 2.0 mmol) and aluminium trichloride (264 mg, 2.0 mmol) were reacted to give 108.9 mg yellow solid compound S36, with a yield of 26%.

ESI-MS: 420.2 [M+H]⁺;

¹H NMR (400 MHz, CDCl₃): δ7.16-7.28 (2H, m), 7.09 (1H, d, J=10.0), 6.93 (1H, s), 6.89 (1H, t, J=10.0), 5.06 (1H, s), 4.69-4.72 (2H, m), 4.04 (2H, s), 2.71-2.74 (2H, m), 2.40-2.43 (1H, m), 2.42 (3H, s), 2.01-2.14 (2H, m), 1.61 (2H, t, J=6.4), 1.03 (6H, d, J=6.4).

EXAMPLE 37

Synthesis of Compound S37

Synthetic Route:

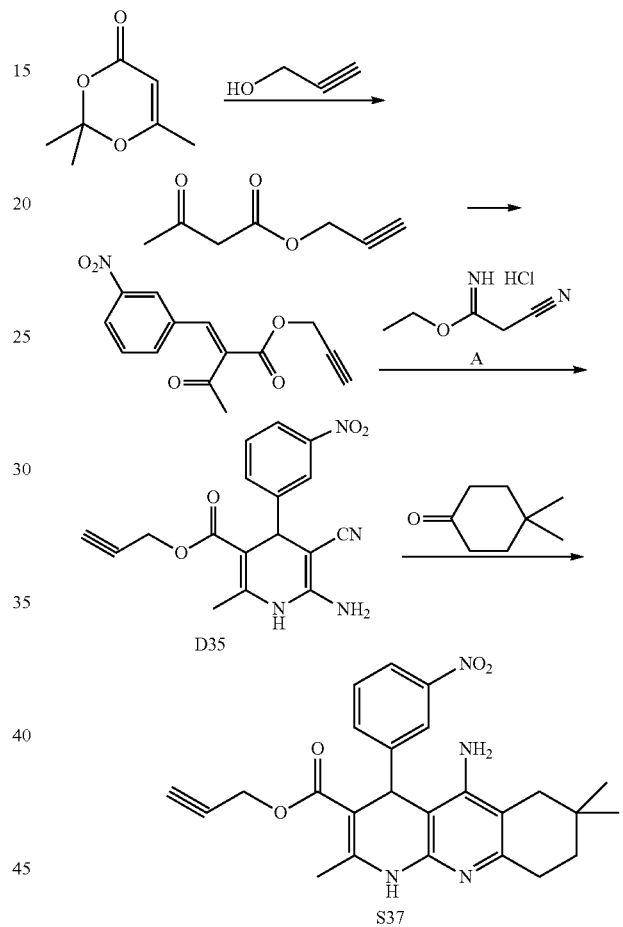

Step 1

By reference to the synthesis of compound D29 in Example 29, using the route in Example 29, a two-step reaction was carried out by using 2,2,6-trimethyl-1,3-dioxin-4-one (0.05 mol), propargyl alcohol (0.05 mol), 3-nitrobenzaldehyde (0.045 mol), ammonium acetate (0.08 mol) and raw material A (0.035 mol) to give 2.25 g yellow solid intermediate D35, with an overall yield of 19%.

Step 2

By reference to the synthesis of S1 in Example 1, intermediate D35 (338 mg, 1 mmol), 4,4-dimethylcyclohexanone (252 mg, 2.0 mmol) and aluminium trichloride (264 mg, 2.0 mmol) were reacted to give 138.3 mg yellow solid compound S37, with a yield of 31%.

ESI-MS: 447.3 [M+H]⁺;

¹H NMR (400 MHz, CDCl₃): δ8.23 (1H, s), 8.04-8.07 (1H, m), 7.71 (1H, d,

J=10.0), 7.43 (1H, t, J=10.0), 7.02 (1H, s), 5.16 (1H, s), 4.73-4.77 (2H, m), 4.06 (2H, s), 2.72-2.77 (2H, m), 2.14-2.48 (1H, m), 2.47 (3H, s), 2.00-2.15 (2H, m), 1.61 (2H, t, J=6.4), 1.03 (6H, d, J=1.6).

EXAMPLE 38

Synthesis of Compound S38

Synthetic Route:

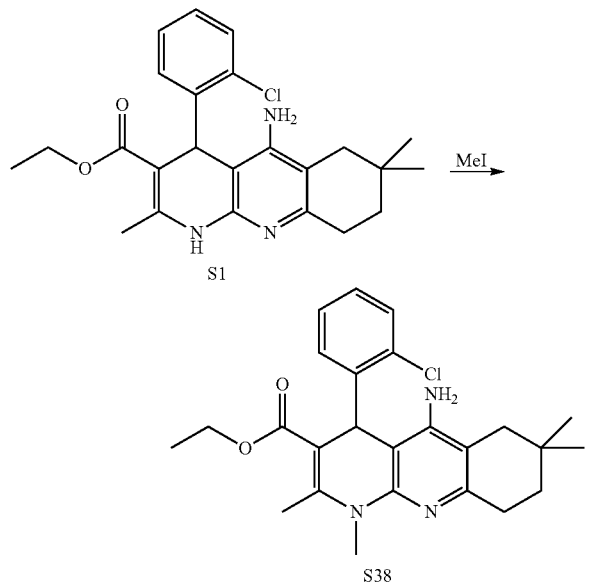

S1 (425 mg, 1.0 mmol), KOH (112 mg, 2.0 mmol) were precisely weighed out and dissolved in 10 ml dichloromethane/acetonitrile (2:1). Subsequently, iodomethane (170 mg, 1.2 mmol) was slowly added dropwise and stirred at room temperature over night. The end of reaction was monitored by TLC. Then 5 mL water was added and the mixture was extracted by dichloromethane (20 mL×3). The organic phase was combined and washed with saturated saline solution. Subsequently, it was dried by anhydrous sodium sulfate, and concentrated. The resultant product is separated by chromatography using silica gel column (petroleum ether:ethyl acetate=4:1) to give 122.9 mg light yellow oil product S38, with a yield of 28%.

ESI-MS: 440.1 [M+H]$^+$;

$^1$H NMR (400 MHz, DMSO-d6): δ7.36 (1H, dd, J=1.6, 7.6), 7.31 (1H, dd, J=1.6, 8.0), 7.14-7.21 (2H, m), 5.29 (1H, s), 5.18 (2H, s), 3.98-4.02 (2H, m), 3.49 (3H, s), 2.57-2.63 (2H, m), 2.58 (3H, s), 1.99-2.15 (2H, m), 1.49 (2H, t, 6.4), 1.14 (3H, t, J=6.8), 0.93 (6H, s).

EXAMPLE 39

Activity of Blocking L-Type $Ca^{2+}$ Channel of the Compounds Detected by Patch Clamp Technique Based on the patch clamp technique, the calcium electric current in the dorsal root ganglion cells of rats were measured in accordance with the following method, and thereby the inhibition activities to the L-type calcium channel of some compounds in examples 1-38 of the present invention were measured.

Experimental Methods:

Culture of Dorsal Root Ganglion Cells:

Reagents: D-MEM/F-12 Medium, Gibco; fetal bovine serum (i.e., FBS), Gibco; collagenase, Sigma; poly L-lysine, Sigma; trypsin, Invitrogen; trypsin inhibitor, Sigma; Culture solution for dorsal root ganglion cells: 90% D-MEM/F-12, 10% FBS, P/S 100 U/Ml; digest solution, freshly prepared before experiment: 5 Ml D-MEM/F-12, 5 mg collagenase, 2.5 mg trypsin.

Instruments: Multiclamp 700B amplifier, Molecular Devices, America; DigiData1440 A/D D/A converter, MDC, America; Pclamp10 software, Molecular Devices, America; inverted microscope, Nikon Ti-S, Japan; program controlled micro-pipette maker DMZ-Universal Puller, Germany; program controlled micro-pipette maker DMZ-Universal Puller, Germany.

Method for preparation of the rat dorsal root ganglion cells: 2 Wister rats (body weight 140 g) were decapitated under pentobarbital anaesthesia. The lumbar L4-L6 dorsal root ganglia were separated from the spine quickly, and placed in PBS dissection solution. The connective tissue and septa were removed from the ganglia, which were subsequently cut into several pieces. The ganglia pieces were treated in the digest solution at 37° C., 5% $CO_2$ for 25-30 min before trypsin inhibitor was added to stop the digestion. After digestion, the cell suspension was centrifuged at 1000 rpm for 2 min. The supernatant was removed and the culture solution was added. After treatment by homogeneously mixing, the mixture was centrifuged again at 1000 rpm for 2 min. The supernatant was removed and the culture solution was added. The cells were then transferred to a 35 mm culture dish coated with 25 μg/Ml poly L-lysine. After incubation for 2 h, the dorsal root ganglion cells were prepared for patch clamp experiment.

100 mmol/L and 1000 mmol/L solutions were prepared by weighing out 10 mmol and 100 mmol 51, S19, S27, S29, respectively, and then dissolved in DMSO at a concentration of 100%. Final test solutions were obtained by diluting the above DMSO solutions in a ratio of 1:1000.

The test solutions for patch clamp experiment were divided into extracellular solution and pipette solution, the composition of which can be seen in table 1 and 2.

TABLE 1

Composition for extracellular solution

| Extracellular solution | mmol/L |
|---|---|
| CsCl | 139 |
| $BaCl_2$ | 5.0 |
| Hydroxyethyl piperazine ethanesulfonic acid (HEPES) | 10 |
| $MgCl_2$ | 1.0 |
| Glucose | 10 |
| Tetraethylammonium chloride (TEA) | 30 |
| 4-aminopyrine (4-AP) | 5 |
| Tetrodotoxin | 0.002 |

PH adjusted to 7.4 by CsOH; Osmotic pressure of 305-310 milliosmolarity.

TABLE 2

Composition for pipette solution

| Pipette solution | mmol/L |
|---|---|
| Cesium methanesulfonate | 126.5 |
| $MgCl_2$ | 2.0 |
| Ethyleneglycol bis(2-aminoethylether) tetraacetic acid (EGTA) | 11 |

TABLE 2-continued

Composition for pipette solution

| Pipette solution | mmol/L |
|---|---|
| Mg-ATP | 8 |
| HEPES | 10 | pH adjusted to 7.3 by CsOH; Osmotic pressure of 290-295 milliosmolarity. Pipette solution was divided into several aliquots and stored at −20° C. before use.

Patch clamp test: the test was carried out at room temperature by whole cell patch clamp technique using Multiclamp 700B amplifier, DigiData1440 A/D D/A converter and 1 kHz filter under the control of Pclamp10 software. The test cells continuously moved through the perfusion system—fast biological solution converter, RSC-160, at a perfusion rate of 1-2 Ml washing solution/min. This process was carried out under an inverted microscope, with the perfusion site inserted manually. Borosilicate glass capillary (BF150-86-10, Sutter Instrument Co.) was pulled out using the program controlled micro-pipette maker. The resistance at the end of the pipette ranged from 2 to 4 MΩ. The voltage control procedure was as follows: from the holding potential of −60 Mv to 0 Mv within 300 ms, then back to −60 Mv within 60 ms. During the test process, the voltage control procedure was repeated every 10 s. During the initial recording, when the peak current was stabilized (i.e., <5% change) for 5-10 recording points, the compounds to be tested were added at low concentration until the peak current was stabilized again for 5 recording points. If on change occurred to the peak current, then wait for 5 min. If necessary, the compounds to be tested were added at high concentration. Each compound was tested for 2 cells.

Data were analyzed and fitted using Clampfit (V10.2, Molecular Devices), Excel 2003 (Microsoft) and SigmaPlot. The inhibition rates were tested for the compounds, and calculated based on the following equation:

[(the electric current of the control−the residual current after adding the compound)/the electric current of the control]×100%

The inhibitory effects of 100 nmol/L and 1 μmol/L compound were listed in table 3:

TABLE 3

Activities of blocking the L-type $Ca^{2+}$ channel of the compounds provided herein

| Compounds provided herein | 100 nmol/L | 1000 nmol/L |
|---|---|---|
| S1 | 38.14% | 61.76% |
| S19 | 4.12% | 26.29% |
| S27 | 39.68% | 65.54% |
| S29 | 11.64% | 23.76% |
| Nifedipine | 22.48% | 36.15% |

The results showed significant activities of the compounds provided herein to block the L-type $Ca^{2+}$ channel, some of which are better than that of the positive control Nifedipine.

EXAMPLE 40

Activity for Blocking L-Type $Ca^{2+}$ Channel of the Compounds Detected by High Content Screening Analyzer The inhibitory activities to the calcium channel of some compounds prepared in Examples 1-38 were evaluated by the inhibitory activity to SH-SY5Y cellular voltage-gated calcium ion influx induced by KCl of the compounds (@10 Mm, @50 Mm) detected by real-time fluorescence method on the high content screening analyzer (HCS) platform.

In the experiment, Fluo-4-AM calcium ion probe was loaded to SH-SY5Y cells under physiological condition. Subsequently, the fluorescent signal was generated by the binding between the fluorescent probe and the calcium ion which flowed into the cells through the cell membrane calcium channel after the opening of the voltage-gated calcium channel induced by KCl. At the same time, high content recording of the real-time intracellular fluorescent signal was performed, which reflected the intensity of the calcium ion influx. Fluorescent can not be generated from Fluo-4-AM itself after excitation. However, when enters the cell, it will be cleaved into Fluo-4 by esterases inside the cytoplasm, which, after binding with calcium ion, will give strong green fluorescent after excitation at 488 nm. KCl is used as an agonist for the voltage-gated calcium channel: when K+ reaches a certain concentration, the voltage-gated calcium channel will open, and thus calcium ions will flow into cells and bind to the dye to give fluorescent. If the calcium channel is inhibited by the compound, the number of calcium ions flowing into the cells will decrease, and the fluorescence intensity reduce thereby. The degree of the reduction is correlated to the inhibition on the calcium channel by the compound. L-type calcium channel belongs to voltage-gated calcium channel. In this experiment, SH-SY5Y cell was used, whose voltage-gated calcium channels on the surface of cell membrane are mainly L-type. Thus, most of the calcium flux signal induced by KCl is L-type calcium channel signal.

Materials and Instruments:

1640+10% FBS+1% P/S Culture solution, and trypsin were all purchased from Gibico.

SH-SY5Y cells were from the cell biology laboratory, Nanjing Medical University.

Fluo-4 Direct™ Calcium Assay Kits: Invitrogen, catalog no. F10471.

High content screening analyzer (HCS): Molecular Devices Company, model: Imagexpress.

96-well black plate: Corning 3603.

Inorganic agent KCl (analytical grade) was purchased from Sigma, which was prepared as 1 M stock solution and diluted to 250 Mm for application.

Experimental Procedure

Preparation of the Dye:

The dye solution was prepared completely according to the instruction of Fluo-4 Direct™ Calcium Assay Kits (Invitrogen, catalog no. F10471). Briefly, a bottle of component A (solid dye) was dissolved in 10 Ml component C (buffer solution), and a tube of component B (Probenecid) was added to 1 Ml component C (buffer solution). Subsequently, to the dissolved component A solution, 200 μL component B was added, resulting in 2×Fluo-4-AM application solution. 100 μL dye solution was then added to each well of a new 96 well plates (Corning 3599) corresponding to the cell wells, and the 96 well plates was placed in HCS for further detection.

Formulation of 2×Compound Solution:

In this experiment, the inhibition rates to the calcium channel of all compounds were detected at both high concentration 50 μM and low concentration 10 μM. Specific preparation methods for both solutions were as follows: all compounds were initially prepared into a 0.01 M stock solution in DMSO, and then the stock solution for each compound was diluted to 5000 μM and 1000 μM using DMSO. For each concentration, 2×compound solution was obtained by 50-fold dilution using 1640 complete culture solution (DMSO was used as the pure solvent control).

Cell Manipulation Procedure:

SH-SY5Y cells at confluence of around 90% were digested by trypsin. 20000 cells were placed per well in the 96-well black plate. After 24 h culture, the culture solution was removed and 45 μL 2×compound solutions motioned above (DMSO was used as the pure solvent control) were added at various concentrations. For each concentration, experiments were performed in quadruplicate. Specific arrangement of the wells in the 96-well plate was shown in table 4:

TABLE 4

Arrangement of wells in the 96-well plate

| DMSO | 100 | 50 | 100 | 50 | 100 | 50 | 100 | 50 | 100 | 50 | DMSO |
|---|---|---|---|---|---|---|---|---|---|---|---|
| DMSO | 100 | 50 | 100 | 50 | 100 | 50 | 100 | 50 | 100 | 50 | DMSO |
| DMSO | 100 | 50 | 100 | 50 | 100 | 50 | 100 | 50 | 100 | 50 | DMSO |
| DMSO | 100 | 50 | 100 | 50 | 100 | 50 | 100 | 50 | 100 | 50 | DMSO |
| DMSO | 100 | 50 | 100 | 50 | 100 | 50 | 100 | 50 | 100 | 50 | DMSO |
| DMSO group | Compound 1/μM | | Compound 2/μM | | Compound 3/μM | | Compound 4/μM | | Compound 5/μM | | DMSO group |

Based on the program set for automatic sample addition by HCS, 45 μL 2×Fluo-4-AM solutions prepared according to the instruction were sequentially added into each well automatically. For each well, the time for dye addition and the time required by detection were maintained the same by parameter setting; meanwhile, the time required for finishing the dye addition and the time for dye incubation were also maintained the same for all wells (in the experiments, the time required for dye incubation was 30 min)

HCS program was set. 250 Mm of 30 μL KCl solution was sequentially added to each well based on the sequence for dye addition (make sure the incubation time for each well was the same). The change of fluorescence intensity was real-time scanned for each well. The fluorescence intensities for 10 time points, F1, F2, F3, . . . , F10, were scanned before KCl addition; the fluorescence intensities for 40 time points, F11, F12, F13, . . . , F50, were also scanned after KCl addition.

The results were listed in table 5.

The average F0 of F1, F2, . . . , F10 was calculated, and the maximal value among F11, F12, F13, . . . , F50 was selected. Δ=Fmax−F0 was recorded.

Inhibition rate=100%*(Δcontrol group−Δadministration group)/Δcontrol group

TABLE 5

Activities of blocking the L-type $Ca^{2+}$ channel of the compounds provided herein

| Compounds provided herein | 10 μM | 50 μM |
|---|---|---|
| S1 | 29.29% | 63.60% |
| S2 | 38.79% | 94.01% |
| S3 | 81.33% | 86.82% |
| S4 | 64.82% | 85.17% |
| S5 | 14.40% | 62.43% |
| S6 | 11.30% | 95.51% |
| S7 | 1.01% | 72.98% |
| S8 | 61.63% | 93.28% |
| S9 | 5.22% | 85.01% |
| S10 | 49.97% | 83.29% |
| S11 | 54.69% | 75.06% |
| S12 | 34.59% | 52.61% |
| S20 | 46.88% | 99.27% |
| S22 | 45.06% | 82.60% |
| S25 | 1.02% | 63.52% |
| S26 | 30.18% | 41.41% |

TABLE 5-continued

Activities of blocking the L-type $Ca^{2+}$ channel of the compounds provided herein

| Compounds provided herein | 10 μM | 50 μM |
|---|---|---|
| S29 | 17.93% | 57.19% |
| S30 | 29.44% | 80.73% |

TABLE 5-continued

Activities of blocking the L-type $Ca^{2+}$ channel of the compounds provided herein

| Compounds provided herein | 10 μM | 50 μM |
|---|---|---|
| S31 | 19.10% | 93.34% |
| S32 | 29.49% | 91.10% |
| S34 | 39.53% | 88.96% |
| S38 | 17.97% | 51.19% |

The results showed that there were significant activities of blocking the L-type $Ca^{2+}$ channel of the compounds provided herein, some of which are better than that of the positive control Nimodipine.

EXAMPLE 41

Detection of the Acetylcholinesterase Inhibition Activities of the Compounds

Samples: Some Compounds Prepared in Examples 1-38

Materials and instruments: AmplexR Red Acetylcholine/Acetylcholinesterase Assay Kit, A12217, invitrogen; 96-well black plate, Costar #3925; Infinite M200 plate reader, Tecan Company.

Formulation of Stock Solution for the Kit:

A tube of Amplex Red reagent, Component A, was added to 200 Ml DMSO, Component B, stored at −20° C. and protected from light; 5×buffer, Component E, diluted to 1× (i.e., 1×Reaction Buffer) using deionized water according to desired volume; a tube of hrp, Component C, added to 1 Ml 1×Reaction Buffer and divided into aliquots, and stored at −20° C.; 5 M13.3% $H_2O_2$, Component D, added to 234.1 Ml deionized water to give 20 mmol/L $H_2O_2$ working solution, which was freshly prepared before use; a tube of Choline Oxidase, added to 600 Ml 1×Reaction Buffer and divided into aliquots, and stored at −20° C.; 5 mg Ach-cl, Component G, added to 275 Ml deionized water to give 100 mmol/L Ach application solution, which was freshly prepared before use; a tube of AchE, added to 600 Ml 1×Reaction Buffer and divided into aliquots, and stored at −20° C.

Formulation of compounds: 0.01 mol/L stock solutions of the compounds were prepared using DMSO based on their qualities and molecular weights. Preparation of 100×Compound: the stock solutions of the compounds were diluted into a concentration gradient using DMSO, including 1000 μmol/L, 200 μmol/L, 40 μmol/L, 8 μmol/L, 1.6 μmol/L, 0.32 μmol/L and 0.064 μmol/L.

Formulation of 4×AchE application solution: a volume of AchE stock solution was diluted with 1×Reaction Buffer in a ratio of 1:250, as desired.

Formulation of 2×working solution: 2×working solution was prepared by mixing each stock solution in a ratio of 200 μL Amplex Red reagent: 100 Ml Horseradish peroxidas: 100 Ml Choline Oxidase: 10 Ml Ach: 9590 Ml 1×Reaction Buffer, as desired.

Procedure: 48 Ml 1×Reaction Buffer was initially added to each compound test well in the 96-well black plate arranged, followed by addition of 2 Ml 100×compound solution; the test for each concentration was performed in duplicate. To the positive control well, 2 Ml DMSO+48 Ml 1×Reaction Buffer were added; while 100 Ml 20 Mm $H_2O_2$ working solution was directly added to the positive validation well. To the negative control well, 2 Ml DMSO+98 Ml 1×Reaction Buffer were added, and each test was performed in duplicate. 50 Ml 4×AchE application solution was added to each of the compound test wells and the positive control wells. 100 Ml 2×working solution was added to each of all the wells and mixed until homogenous. The enzymatic reaction was started with the volume of the overall reaction system reaching 200 Ml, which resulted in the final concentrations of the compound solution of 10 μmol/L, 2 μmol/L, 0.4 μmol/L, 0.08 μmol/L, 0.016 μmol/L, 0.0032 μmol/L and 0.00064 μmol/l. The system was incubated at room temperature for 30-45 min.

Detection of fluorescent: the fluorescent value for each well was detected at the excitation wavelength of 540 nm and the emission wavelength of 590 nm by Infinite M200 plate reader, in which the gain value was set at optimal.

Data analysis: average values were calculated for all administration groups and control groups, and the inhibition rate was calculated according to the following equation:

$$\text{Inhibition rate} = 1 - \left( \frac{\text{average } OD \text{ value of the administration group} - \text{average } OD \text{ value of the negative control group}}{\text{average } OD \text{ value of the positive control group} - \text{average } OD \text{ value of the negative control group}} \right) \times 100\%$$

Log 10 values for the administration concentrations were calculated and set as the X axis, and the inhibition rates were set as the Y axis. The data were plotted in origin 6.0, and fitted to an S curve for pharmacological dose-effect relationship, by which the concentration corresponding to 50% inhibition rate was calculated, i.e., IC50 value of such compound for acetylcholinesterase inhibition activity. The results of the acetylcholinesterase inhibition activity by the compounds were listed in table 6.

TABLE 6

The results of the acetylcholinesterase inhibition activity by the present compounds.

| Compounds provided herein | Inhibition activity IC$_{50}$ (nmol/L) |
|---|---|
| S1 | 768 |
| S2 | 558 |
| S3 | 1125 |
| S4 | 1055 |
| S5 | 770 |
| S6 | 893 |
| S7 | 1377 |
| S8 | 757 |
| S9 | 919 |
| S10 | 971 |
| S15 | 729 |
| S18 | 504 |
| S19 | 333 |
| S20 | 732 |
| S21 | 1107 |
| S22 | 450 |
| S23 | 540 |
| S25 | 842 |
| S27 | 178 |
| S28 | 136 |
| S29 | 45 |
| S30 | 5960 |
| S31 | 3030 |
| S32 | 6918 |
| S33 | 1836 |
| S34 | 1780 |
| S35 | 1792 |
| S36 | 1928 |
| S37 | 1860 |

The results indicated that 1,4-dihydro-naphthyridine derivatives are capable of inhibiting the activity of acetylcholinesterase.

EXAMPLE 42

Effect of the Compounds on Primary Neuron Toxicity, Morphology of the Neurons and Tau Protein Phosphorylation Experiment Reagents:
Complete neuron medium: Neurobasal medium+B27 (2%)+L-Glutamine (0.5 mM)+P/S (1%)

| Name | Source (Company/Catolog No./Lot No.) | Concentration used in the experiment |
|---|---|---|
| Primary cortical neuron cells | Prepared in the Lab | N/A |
| Tau Antibody (Ab-396) | GenScript/A00389/R50391203 | 1:1000 |
| P-Tau (S396) pAb Reagent | Bioworld/360779 | 1:1000 |
| β-Actin (ACTBD11B7) | Santa Cruz/G1311 | 1:1000 |
| Anti-Mouse IgG | Sigma/A2554 | 1:2000 |
| Anti-Rabbit IgG | Sigma/A0545 | 1:2000 |
| Neurobasal | Gibco/21103/1042202 | N/A |
| B27 | Gibco/17504-044/1094171 | 1:50 |
| L-Glutamine | Beyotime/C0212 | 1:400 |
| double-antibody (P/S) | Gibco/15140 | 1:100 |
| CellTiter-Glo | Promega/G7571 | N/A |

Instruments:
Gel imager (Fluor Chem™): Alpha Innotech
Plate reader (PHERAstar FS): BMG LABTECH
Plate: 12-well plate, Costa #3513
Microscope: Olmpus IX70
Experimental Methods:
Preparation of Primary Cortical Neuron Cell 18-day pregnant SD rats were sacrificed by cervical vertebra dislocation. The cerebral cortex was separated from the E18 fetal rat, cut into particles<1 mm³, and washed by pre-cooled DMEM. The mixture was centrifuged at 1000 rpm for 5 min, and the supernatant was discarded. The pellet was digested by pre-warmed trypsin at 37° C. The digestion was stopped by 20% FBS. The digest suspension was centrifuged at 1000 rpm for 5 min, and the supernatant was discarded. The pellet was re-suspended in complete neuron medium, centrifuged at 1000 rpm for 5 min, and the supernatant was discarded. The pellet was re-suspended in complete neuron medium and passed through 200 mesh cell strainer. The cell suspension through the cell strainer was diluted with complete neuron medium to 2×105 cells/mL. 1 mL cell suspension was inoculated to the 12-well plate pre-coated by PDL. A half of the medium was replaced the next day, which was repeated every other day thereafter. The in vitro culture was maintained until it differentiated to mature neurons, and this material was ready for experiment.

Comparative Compounds:

The synthesis methods of known compounds A1, A2, A3, and A4 can be found in *J. Med. Chem.* 2009, 52, 2724-2732

A1

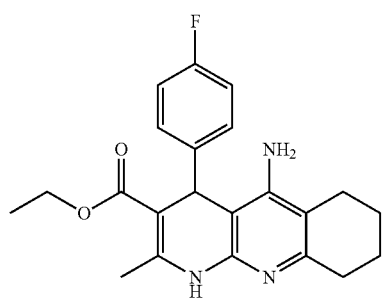

A2

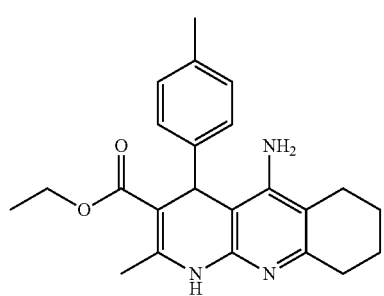

A3

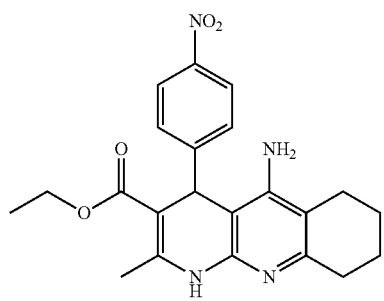

A4

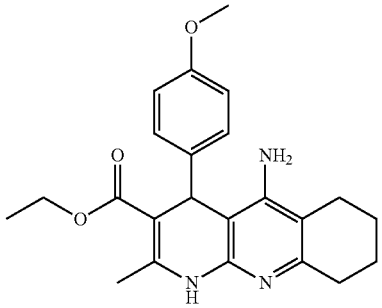

Formulation of the Compounds

The compounds were dissolved in DMSO to prepare the stock solution at concentration of 0.01 M, and it was then stored at −20° C. The stock solution was initially diluted to an appropriate concentration using DMSO before use, and subsequently it was diluted by the complete neuron medium to concentrations including 0.01, 0.1 and 1 μM (DMSO content: 0.1%).

Effect of the Compounds on the Morphology of Neurons

After 7-day in vitro culture of neurons, the culture solution was discarded and 1 mL/well compound solution prepared as mentioned above was added (12-well plate). The plate was then incubated for 24 h (a DMSO control group was also performed at the same time). The morphology of neurons were examined under a microscope and photographed.

Neuron Toxicity Test

After incubation with the compounds for 24 h, 100 μL reagent/well was added according to the instruction of cellti-ter-Glo. Subsequently, the plate was shaken for 10 min, and the chemiluminescence values of the compounds were read by a PHERAstar FS plate reader. The relative neuron activity was calculated based on the following equation:

Relative neuron activity (%)=(The activity of the administration group−The activity of the background group)/(The activity of the DMSO group−The activity of the background group)× 100%

Sample Preparation for Western Blot and Detection

After incubation with the compounds for 24 h, the culture medium was discarded. Subsequently, it was washed by pre-cooled PBS once, followed by cell lysis. After SDS loading buffer was added, it was boiled in water for 10 min and centrifuged for future use. SDS-PAGE electrophoresis was performed to the above collected samples which were subsequently transferred to NC membrane and blocked by 5% defatted milk at room temperature for 1 h. The membrane was washed by TBST for 3 times for 5 min each time. It was then incubated with the primary antibody (1:1000) overnight, and was washed by TBST for 3 times for 5 min each time. Subsequently, it was incubated with the secondary antibody (1:5000) overnight, and was washed by TBST for 3 times for 5 min each time. Finally, the gel was imaged with ECL by Alpha gel imaging system (Fluor Chem™)

Results:

Toxicity of the Compounds to Neurons

It can be seen from table 7 that compound S15 had minor toxicity to primary neurons, which merely exhibited cytotoxicity at 1 μM; no significant toxicity was observed for S1, S3, S6, S8 and S32 at concentrations tested; A1, A2, A3 and A4 had stronger toxicity, in which A2, A3 and A4 already exhibited very strong neuron toxicity even at the concentration of 0.01 μM.

TABLE 7

Effect of the compounds on primary neuron activity
Relative neuron activity (average)

| No. | 0.01 μM | 0.1 μM | 1 μM |
|---|---|---|---|
| S1 | 110.6% | 113.9% | 97.9% |
| S3 | 107.7% | 102.4% | 98.8% |
| S6 | 107.1% | 105.3% | 99.0% |
| S8 | 114.7% | 101.7% | 97.7% |
| S10 | 120.7% | 96.3% | 70.3% |
| S15 | 111.9% | 105.8% | 65.9% |
| S20 | 103.9% | 98.5% | 47.5% |
| S27 | 123.7% | 102.9% | 43.0% |
| S32 | 115.5% | 106.5% | 98.6% |
| A1 | 100.2% | 87.4% | 25.5% |
| A2 | 51.4% | 21.2% | 9.9% |
| A3 | 40.5% | 18.2% | 0% |
| A4 | 67.3% | 23.5% | 2.0% |

Effect of the Compounds on the Morphology of Neurons

It can be seen from FIG. 1, the compounds (such as S1) with no neuron cytotoxicity had no effect on the morphology of neurons at the concentrations ranged from 0.01 to 1 μM; while for the compounds (such as A2) with stronger cytotoxicity, at concentrations of 0.1 and 1 μM, neuron axon/dendrite was broken up and the cells was crimpled 24 h after administration; and at the concentration of 1 μM, no morphology of neurons was observed.

Effect of the Compounds on Intracellular Tau Phosphorylation of Neurons

Figure 2:
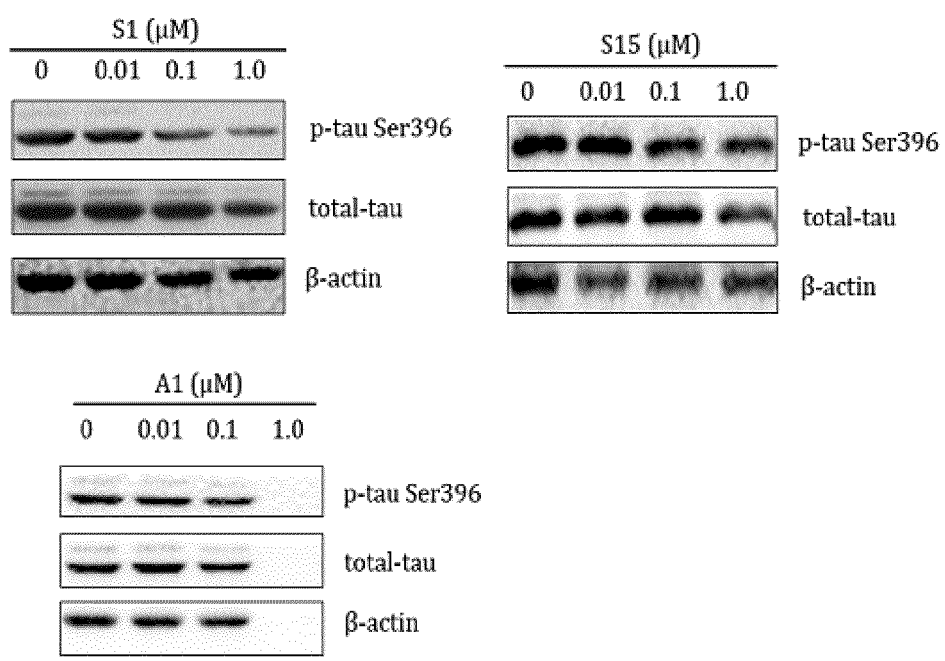
FIG. 2 depicts the regulation effect of compounds of the disclosure (S1, S15, and A1) on the intracellular tau protein phosphorylation of primary neurons of compounds.

It was suggested by the results of Western Blot that intracellular tau protein phosphorylation of neurons can be reduced by the compounds with on neuron cytotoxicity, such as S1, S3, S6, S8, S15 (except that minor toxicity at the concentration of 1 μM was exhibited, see table 1) and S32 (See FIGS. 2, S1 and S15). For the compounds with very strong toxicity such as A2, A3 and A4, most cells died at the concentration of 1 μM with sharply decreased intracellular proteins due to the very strong toxicity to neurons (See FIG. 2-A1).

CONCLUSIONS based on the experimental results above, the compounds of the present invention not only can inhibit the activity of acetylcholinesterase, but also can block the influx of extracellular calcium ions into cells through the calcium channel, i.e., has dual-activities. The compounds of the present invention have significant advantages over the compounds that are already known in the aspect of primary neuron toxicity, and have significant down-regulation of Tau protein phosphorylation—an importance biomarker for senile dementia. Thus, the compounds of the present invention are of great value as a potential therapeutic agent.

The content described above is only the preferable embodiments of the present invention, and it should be noted that several improvements and modifications can be made by the person of ordinary skill in the art without departing from the principles of the present invention. These improvements and modifications should also be regarded as in the scope of the present invention.

What is claimed is:

1. A compound of formula I or a pharmaceutically acceptable salt thereof:

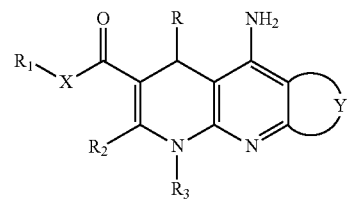

Formula I wherein

R is phenyl, and said phenyl is substituted at any position on the ring by halogen atom or nitro;

X is —O—;

$R_1$ is;

$R_2$ is $C_1$ alkyl;

$R_3$ is hydrogen;

Y is substituted $C_4$ alkylene, and any position on said substituted $C_4$ alkylene is substituted by one or two or more substituents selected from the group consisting of halogen atom and $C_1$-$C_6$ alkyl.

2. The compound or pharmaceutically acceptable salt according to claim 1 wherein Y is substituted $C_4$ alkylene, and any position on said substituted $C_4$ alkylene is by two substituents selected from the group consisting of methyl, ethyl, and propyl.

3. A compound or pharmaceutically acceptable salt thereof, selected from the group consisting of:

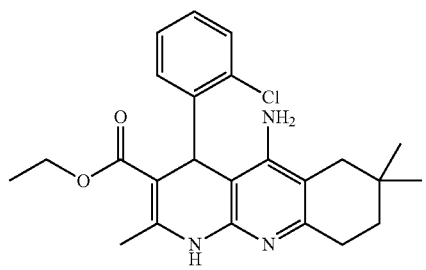

Compound 1: 5-amino-4-(2-chlorphenyl)-2,7,7-trimethyl-1,4,6,7,8,9-hexahydrobenzo[b][1,8]naphthyridine-3-carboxylic acid ethyl ester, as shown by S1;

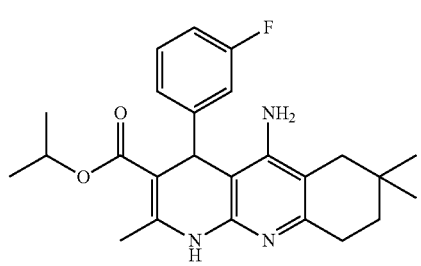

Compound 3: 5-amino-4-(3-fluorophenyl)-2,7,7-trimethyl-1,4,6,7,8,9-hexahydrobenzo[b][1,8]naphthyridine-3-carboxylic acid isopropyl ester, as shown by S3;

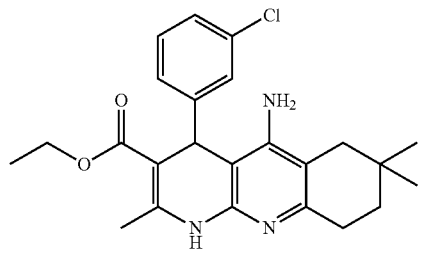

Compound 6: 5-amino-4-(3-chlorphenyl)-2,7,7-trimethyl-1,4,6,7,8,9-hexahydrobenzo[b][1,8]naphthyridine-3-carboxylic acid ethyl ester, as shown by S6;

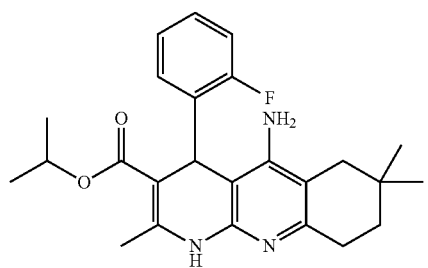

Compound 8: 5-amino-4-(2-fluorophenyl)-2,7,7-trimethyl-1,4,6,7,8,9-hexahydrobenzo[b][1,8]naphthyridine-3-carboxylic acid isopropyl ester, as shown by S8;

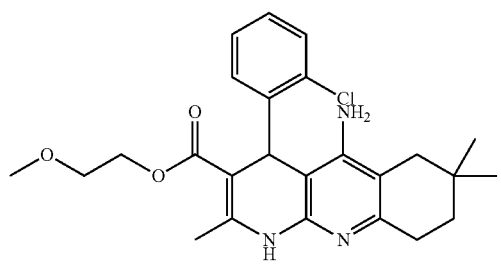

Compound 10: 5-amino-4-(2-chlorphenyl)-2,7,7-trimethyl-1,4,6,7,8,9-hexahydrobenzo[b][1,8]naphthyridine-3-carboxylic acid methoxylethyl ester, as shown by S10;

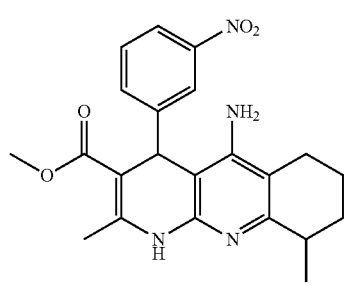

Compound 15: 5-amino-4-(3-nitrophenyl)-2,9-dimethyl-1,4,6,7,8,9-hexahydrobenzo[b][1,8]naphthyridine-3-carboxylic acid methyl ester, as shown by S15;

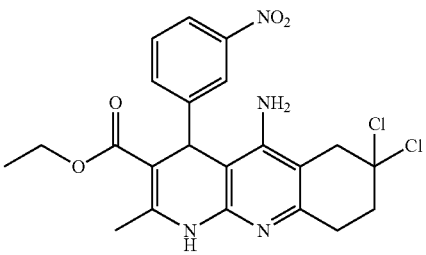

Compound 20: 5-amino-7,7-dichloro-2-methyl-4-(3-nitrophenyl)-1,4,6,7,8,9-hexahydrobenzo[b][1,8]naphthyridine-3-carboxylic acid ethyl ester, as shown by S20;

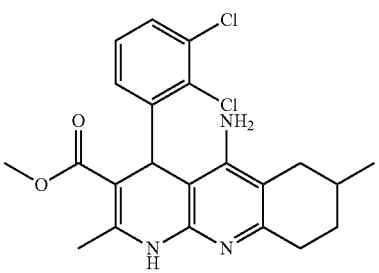

Compound 27: 5-amino-4-(2,3-dichlorophenyl)-2,7-dimethyl-1,4,6,7,8,9-hexahydrobenzo[b][1,8]naphthyridine-3-carboxylic acid methyl ester, as shown by S27;

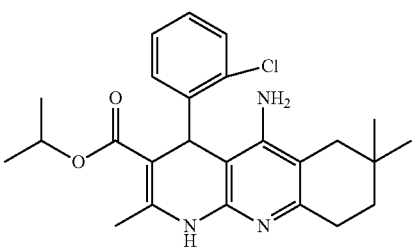

Compound 32: 5-amino-2,7,7-trimethyl-4-(2-chlorphenyl)-1,4,6,7,8,9-hexahydrobenzo[b][1,8]naphthyridine-3-carboxylic acid isopropyl ester, as shown by S32.

4. A method for inhibiting calcium channels in a subject, comprising administering to the subject a compound or pharmaceutically acceptable salt thereof according to claim 1.

5. A method for inhibiting acetylcholinesterase in a subject, comprising administering to the subject a compound or pharmaceutically acceptable salt thereof according to claim 1.

6. A pharmaceutical composition comprising a compound or pharmaceutically acceptable salt thereof according to claim 1 and a pharmaceutically acceptable carrier.

* * * * *